US007838661B2

(12) United States Patent
Tuschl et al.

(10) Patent No.: US 7,838,661 B2
(45) Date of Patent: Nov. 23, 2010

(54) MICRORNA MOLECULES

(75) Inventors: Thomas Tuschl, New York, NY (US); Mariana Lagos-Quintana, New York, NY (US); Winfried Lendeckel, Hohengandern (DE); Jutta Meyer, Bispingen (DE); Reinhard Rauhut, Goettingen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 12/550,586

(22) Filed: Aug. 31, 2009

(65) Prior Publication Data
US 2010/0087513 A1 Apr. 8, 2010

Related U.S. Application Data

(62) Division of application No. 11/747,409, filed on May 11, 2007, now Pat. No. 7,723,510, which is a division of application No. 10/490,955, filed as application No. PCT/EP2002/010881 on Sep. 27, 2002, now Pat. No. 7,232,806.

(30) Foreign Application Priority Data

Sep. 28, 2001 (EP) .................................. 01123453
Mar. 22, 2002 (EP) .................................. 02006712
Jul. 26, 2002 (EP) .................................. 02016772

(51) Int. Cl.
*C07H 21/04* (2006.01)
*C07H 21/02* (2006.01)
*A61K 48/00* (2006.01)

(52) U.S. Cl. .................. 536/24.5; 536/23.1; 536/24.31; 536/24.33; 514/44

(58) Field of Classification Search ........................ None
See application file for complete search history.

(56) References Cited

U.S. PATENT DOCUMENTS

| 5,801,154 A | * | 9/1998 | Baracchini et al. | ............. 514/44 |
| 5,861,310 A | * | 1/1999 | Freeman et al. | ............. 435/325 |
| 6,506,559 B1 | * | 1/2003 | Fire et al. | ....................... 435/6 |
| 6,821,724 B1 | * | 11/2004 | Mittman et al. | ................. 435/6 |
| 6,905,827 B2 | * | 6/2005 | Wohlgemuth et al. | .......... 435/6 |

OTHER PUBLICATIONS

Lee et al., An Extensive Class of Small RNAs in Caenorhabditis elegans, 2001, Science, vol. 294, pp. 862-864.*
Elbashir et al., Functional anatomy of siRNAs for mediating efficient RNAi in Drosophila melanogaster embryo lysate, 2001, The EMBO Journal, vol. 20, No. 23, pp. 6877-6888.*

Wahlestedt et al., Potent and nontoxic antisense oligonucleotides containing locked nucleic acids, 2000, PNAS, vol. 97, No. 10, pp. 5633-5638.*
Krutzfeldt et al., Strategies to determine the biological function of microRNAs, 2006, Nature Genetics, vol. 38, S14-S19.*
Cullen, RNAi the natural way, 2005, Nature Genetics, vol. 37, No. 11, pp. 1163-1165.*
Lee et al., The C. elegans Heterochronic Gene lin-4 Encodes Small RNAs with Antisense Complementarity to lin-14, 1993, Cell, vol. 75, pp. 843-854.*
Marra et al., AA209594, EST Feb. 18, 1997, see search result labeled "20090122_121332_us-11-747-409-88.rst", result #3 in SCORE (enclosed in office action).*
Lee et al., "An Extensive Class of Small RNAs in Caenorhabditis elegans", SCIENCE, vol. 294, Oct. 26, 2001, pp. 862-864.
Elbashir et al., "Functional anatomy of siRNAs for mediating efficient RNAi in Drosophila melanogaster embryo lystae", The EMBO Journal, vol. 20, No. 23, pp. 6877-6888, 2001.
Dropsophila melanogaster sequence (P1 DS08416(D52)), complete sequence; retrieved from Database EMBL Accession No. AC 002442 (Mar. 3, 2000)
Pasquinelli Amy F. et al., "Conservation of the sequence and temporal expression of let-7 heterochronic regulatory RNA", Nature, vol. 408, No. 6808, 2000, pp. 86-89.
Reinhart Brenda J. et al., "The 21-nucleotide let-7 RNA regulates developmental timing in Caenorhabditis elegans.", Nature, vol. 403, No. 6772, Feb. 24, 2000, pp. 901-906.
Moss Eric G. et al., "The cold shock domain protein LIN-28 controls developmental timing in C. elegans is regulated by the lin-4 RNA"., Cell, vol. 88, No. 5, 1997, pp. 637-646.
GenBank accession No. AE014298.
GenBank accession No. AC101777.
GenBank accession No. AL392165.
GenBank accession No. AL355858.
Quintana et al., "Identification of Novel Genes Coding for Small Expressed RNAs", Science, vol. 294, Oct. 26, 2001, pp. 853-858.
Elbashir et al., "RNA interference is mediated by 21-and 22-nucleotide RNAs", Genes & Development, 15: 2001, pp. 188-200.

* cited by examiner

*Primary Examiner*—Amy Bowman
(74) *Attorney, Agent, or Firm*—Rothwell, Figg, Ernst & Manbeck, P.C.

(57) ABSTRACT

In *Caenorhabditis elegans*, lin-4 and let-7 enclode 22- and 21-nucleotide RNAs, respectively, that function as key regulators of developmental timing. Because the appearance of these short RNAs is regulated during development, they are also referred to as "small temporal RNAs" (stRNAs). We show that many more 21- and 22-nt expressed RNAs, termed microRNAs, (miRNAs), exist in invertebrates and vertebrates, and that some of these novel RNAs, similar to let-7 stRAN, are also highly conserved. This suggests that sequence-specific post-transcriptional regulatory mechanisms mediated by small RNAs are more general than previously appreciated.

19 Claims, 59 Drawing Sheets

A

B

Fig.4

Figure 1A:
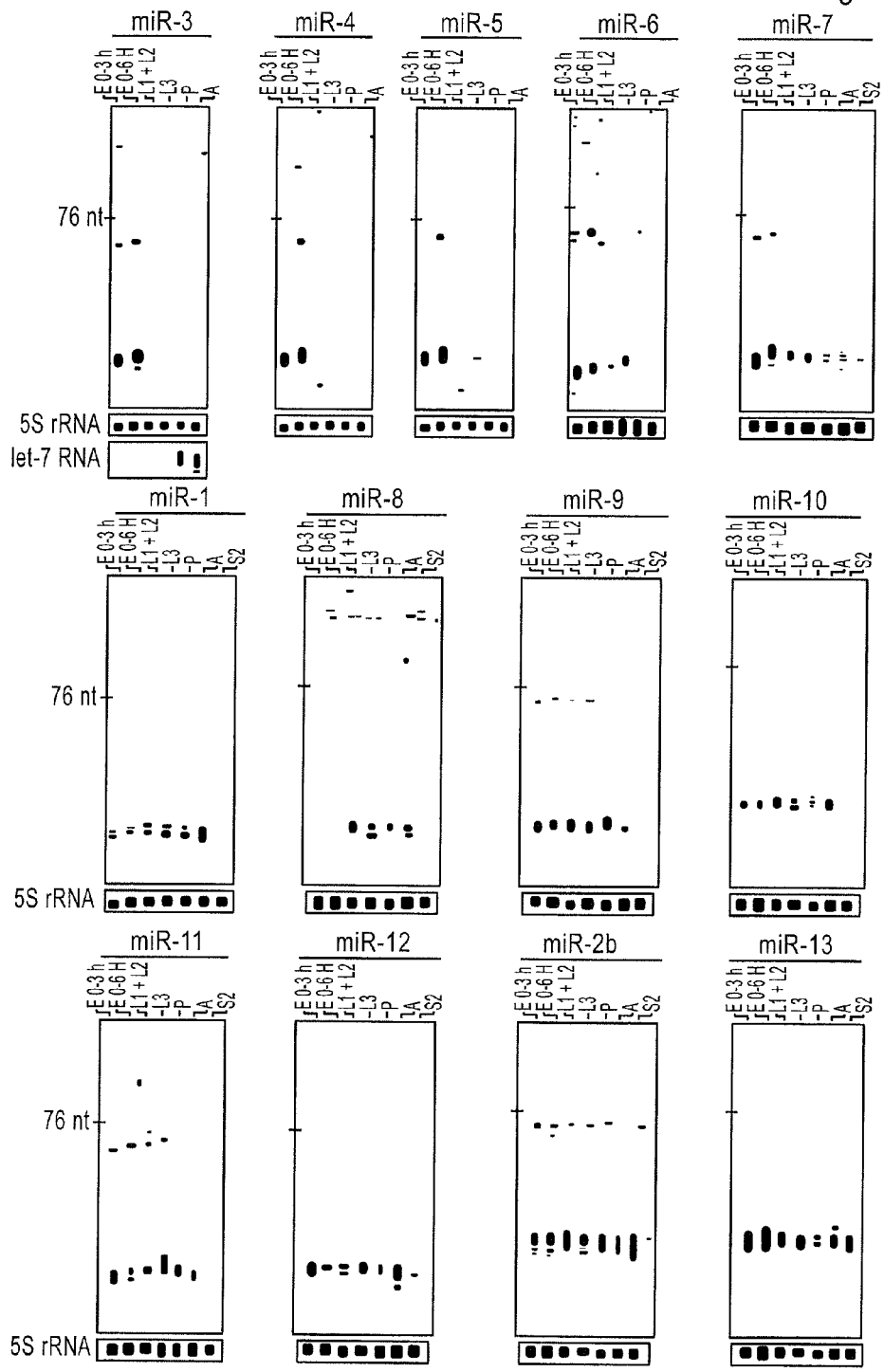

```
let-7a-1            U              UUAGG  ACA   C
chr. 9,17    5' UGGGA GAGGUAGUAGGUUGUAUAGUU   GUC   CCCA  C
             AUCCU UUCUGUCAUCUAACAUAUCAA  UAG   GGGU  A
                          -              -----  A--   C let-7a-2          UU  G  U         UAGAAUUAC  AA
chr. 11      5' AGG GAG UAG AGGUUGUAUAGUU   AUC  G
             UCC UUC AUC UCCACAUGUCAA   UAG  G
              U-   G   C           ---------  AG let-7a-3          U              ---------       U
chr. 22      5' GCG GAGGUAGUAGGUUGUAUAGUU    UGGGGC \
             UCC UUCUGUCAUCUAACAUAUCAA    GUCCCG  C
              U                  UAGGGUAUC       U let-7b            U       - A------       UG
             5' CGGGG GAGGUAGUAGGUUGUGUGGUU  UC    GGGCAG \
             GUCCC UUCCGUCAUCCAACAUAUCAA AG    CCCGUU A
              -                  U AAGGCUC      GU let-7c         A    UU  G  U            UA  G  A AC
             5' GC UCCGGG GAG UAG AGGUUGUAUGGUU  GA UU C \
             CG AGGUUC  UUC AUC UCCAACAUGUCAA   UU AG G  C
              -           CU  G  U          --  G  G UC let-7d           A        C    UUA------    GG
             5' CCUAGGA GAGGUAGUAGGUUG AUAGUU     GGGCAG \
             GGAUUCU UUCCGUCGUCCAGC UAUCAA     CCCGUU A
              -         -      A    UGGAGGAACA    UU let-7e           C  CU   G           U  GGA---- A
             5' CC GGG GAG UAGGAGGUUGUAUAGU   GA      GG C
             GG CCC UUC AUCCUCCGGCAUAUCA  CU      CC A
              A  CU   G              - AGAGGAA  C let-7f-1         AGU                ---------    UG
chr. 9,17    5' UCAG GAGGUAGUAGAUUGUAUAGUUGU   GGGGUAG \
             AGUC UUCCGUAUCUAACAUAUCAAUA    UCCCAUU A
                  CC-                GAGCACUUG     UU
```

```
mir-20          C  A-        G - UU
             5' GUAG ACU  AAGUGCUUAUAGUCCAG  UAG UG  U
             CGUC UGA  UUCACGAGUAUUACGUC  AUC AU  A
              A   AA          - U UG mir-21           A  A   A  U AA
             5' UGUCGGGUAGCUUAUC GACUG UGUUG  CUGU G \
             ACAGUCUGUCGGGUAG CUGAC ACAAC  GGUA C  U
                             -   C   -   - UC mir-22          U CC       - A   U CCUG
             5' GCC GAG GCAGUAGUUCUUCAG UGGCA GCUUUA GU \
             CCG CUC CGUUGUCAAGAAGUU ACCGU CGAAAU CG  A
              U  C-           G         -   -   - ACCC mir-23          C  C       G  G  CUUC
             5' GG CGG UGGGG UUCCUGG GAUG GAUUUG   C
             CC GCC ACCUU AGGGACC UUAC CUAAAC   U
              A  A   U     G   A    ACUG mir-24-1        G  G   A     UA  UCUCAU
chr. 9       5' CUCC GU CCU CUGAGCUGA  UCAGU       \
             GAGG CA GGA GACUUGACU  GGUCA    U
              A  A   C     C-    CACAUU mir-24-2       CC  CG CU-     AA--   UU
chr. 19      5' CUCUG UCC  UGC  ACUGAGCUG   ACACAG \
             GGGAC AGG  ACG  UGACUCGGU   UGUGUU G
              A-  --    ACU    CACA      UG mir-25         A   AG  G   UU G  UG  ACG
             5' GGCC GUGUUG  AGGC GAGAC  G GCAAU CUGG  C
             CCGG CGUGAC  UCUG CUCUG  C CGUUA GGUC  U
              C    AG   G    UU A     CG   CCG mir-26a        G  U   U        GCAG
             5' GUG CCUCGU CAAGUAA CCAGGCAUAGGCUGU   G
             CGC GGGGCA GUUCAUU GGUUCUAUCCGGUA    U
              A   C   -          ACCC
```

A

| | |
|---|---|
| C. elegans lin-4 | UCCCUGAGACCUC--AAG-UGUGA |
| D. melanogaster miR-125 | UCCCUGAGACCCU--AACUUGUGA |
| M. musculus/H. sapiens miR-125b | UCCCUGAGACCCU--AACUUGUGA |
| M. musculus/H. sapiens miR-125a | UCCCUGAGACCCUUUAACCUGUGA |

B

Fig.7

| name | sequence | structure |
|------|----------|-----------|
| let-7a-1 | UGAGGUAGUAGGUUGUAUAGUU | ```
      UG   U       UUAGG      ACA   CCCA C
   CAC  UGGGA GAGUAGUAGGUUGUAUAGUU    GUC     A
   GUG  AUCCU UUCUGUCAUCUAACAUUCAA    UAG   GGGU C
      CA   -       -----      A---      
``` |
| let-7a-2 | UGAGGUAGUAGGUUGUAUAGUU | ```
      UU  G  U       UAGAAUUAC  AA  G
   AGG  GAG UAG AGGUUGUAUAGUU        AUC G
   UCC  UUC AUC UCCGACAUGUCAA        UAG AG
      U-  G  C                   
``` |
| let-7a-3 | UGAGGUAGUAGGUUGUAUAGUU | ```
                                U
      U                      UGGGGC     C
   GGG GAGGUAGUAGGUUGUAUAGUU       GUCCCG U
   UCC UUCUGUCAUCUAACAUGUCAA       UAGGUAUC
      U                      -----
``` |
| let-7b | UGAGGUAGUAGGUUGUGUGGUU | ```
      GG U               A----- UG
   CGGGG GAGGUAGUAGGUUGUGUGGUU UC    GGCAG   A
   GUCCC UUCCGUCAUCCAACAUCAA AG    CCCGUU  GU
      -- -               U AAGGCUC
``` |
| let-7c | UGAGGUAGUAGGUUGUAUGGUU | ```
      UU  G  U       UA  G  GA U  C  AC
   GC  UCCGGG GAG UAG AGGUUGUAUGGUU        GA U U  C
   CG  AGGUUC UUC AUC UCCAACAUGUCAA        UU  A G C
      CU    G  U                   -- G  GG UC
``` |
| let-7d | AGAGGUAGUAGGUUGCAUAGU | ```
         A       C  UUA------  GG
   CCUAGGA GAGUAGUAGGUUG AUAGU         GGGCAG  A
   GGAUUCU UUCCGUCGUCCAGC UAUCAA       CCCGUU UU
         - -       A       UGGAGGAACA
``` |
| let-7e | UGAGGUAGUAGGUUGCAUAGU | ```
   C  CU  G       U  GGA----   A
   CC  GGG GAG UAGGAGGUUGCAUAGU    GG C
   GG  CCC UUC  AUCCUCCGGCAUAUCA   CC A
      A  CU  G       - AGAGGAA    C
``` |

Fig.7 (cont.)

| Name | Sequence | Structure |
|---|---|---|
| let-7f-1 | UGAGGUAGUAGAUUGUAUAGUU | `UCAG     GAGGUAGUAGAUUGUAUAGUGU        GGGGUAG   UG\`<br>`    AGU                              --------         UCCCAUU A`<br>`AGUC     UUCCGUUAUCUAACAUAUCAAUA        GAGGACUUG UU`<br>`    CC-` |
| let-7f-2 | UGAGGUAGUAGAUUGUAUAGUU | `CUGUGGGA GAGGUAGUAGAUUGUAUAGUU    UUAGGG  UCAU A`<br>`         U                      --------                 C`<br>`GGCACCCU UUCCGUCAUCUGACAUAUCAA    UAGA    GGUUCU ACCC`<br>`         -                                              C` |
| let-7g | UGAGGUAGUAGUUUGUACAGUA | `   A  U  A   UGAGG     GUCU  A-  A  A`<br>`CC GGC GAGGUAGU GUUUGUACAGUU    UAGA  UG UACC C`<br>`GG CCG UUCCGUCA CGGACAUGUCAA    UAGA  AC AUGG C`<br>`   A  -  C   -----     -----  GG   -  -  C` |
| let-7h | UGAGGUAGUAGUUUGUACAGUU |  |
| let-7i | UGAGGUAGUAGUUUGUGCU | `     U              U  GG UGUG\`<br>`CUGGC GAGGUAGUAGUUUGUGC GUU     CGGGU A`<br>`GAUCG UUCCGUCAUCGAACGCG CAA     GCCCG UUAC`<br>`     U              -  UAGAGGUG -` |
| miR-1 | UGGAAUGUAAAGAAGUAUGAG | `   A  UUUGAGA    C   A    - AUA\`<br>`UUC GCC       GUUCCAUGCUUC UUGCAUUC AUA GUU`<br>`GAG CGG       CGAGGUAUGAAG AAUGUAAG UAU CGA U`<br>`   -  UCUAAAG    A   G    A ACU` |
| miR-1b | UGGAAUGUAAAGAAGUAUGUAA | `            A       AC`<br>`UGGGA ACAUACUUCUUUAUAU  CCAUA   UGG\`<br>`ACUCU UGUAUGAAGAAAUGUA  GGUAU   AUC C`<br>`            A       A-     CGA   GU`<br>`AL449263.5` |

Fig.7 (cont.)

| | | |
|---|---|---|
| miR-1c | UGGAAUGUAAGAAGUAUGUAC | GCUUGGGA ACAUACUUCUUUAUAU C GC CCAUA UGAACC U<br>CGGACUUU UGUAUGAAGAAAUGUA A− GGUAU CGAAUC G |
| miR-1d | UGGAAUGUAAGAAGUAUGUAUU | GCUGGGCUC UCAAAG UGGUUGUGA AUGC A AUUUC CGC UU<br>CGAUUCGAG AGUUUC ACCGACACU UACG U A GGG CG CG |
| miR-2a-1 | UAUCACAGCCAGCUUUGAUGAGC | AUCU AGC UCAUCAAG UGGUUGUGAUAUG GAUAC C<br>UAGG UCG AGUAGUUU ACCGACACUAUAC GCAAC C<br>A − G CG |
| miR-2a-2 | UAUCACAGCCAGCUUUGAUGAGC | U UG A C U<br>CU CAAC UCUUCAAAG UGGC GUGA AUGUUG C<br>GG GUUG AGGAGUUUC ACCG CACU UAUAAC A<br>C CG G A AUACU |
| miR-2b-1 | UAUCACAGCCAGCUUUGAUGAGC | A − UUU−− CUU U<br>UUGUGUC UUCUUCAAAG UGGUUGUGA AUG GC U<br>AGCGCAG GAGGAGUUUC ACCGACACU UAC CG U<br>C A G UUAUC UAU |
| miR-2b-2 | UAUCACAGCCAGCUUUGAGGAGC | |
| miR-3 | UCACUGGGCAAAGUGUCUCA | C C G U UUCA<br>GAUC UGGAUGCAU UUGU CAGU AUGU A<br>CUAG ACUCUGUG AACG GUCA UACA A<br>A G C CUCU |

Fig.7 (cont.)

| | | |
|---|---|---|
| miR-4 | AUAAAGCUAGACAACCAUUGA | ```
            U      UU   C  C  C  GG   UU
UUGCAAU  AGUUC  UGGU GUC AGC UUA  UGAUU  \
GGGUUG  UCGAAG  ACCA CAG UCG AAU  ACUGG   U
            C      UU   A  A  A  --   CC
``` |
| miR-5 | AAAGGAACGAUCGUUGUGAUAUG | ```
         UA---    C                 AGUUGU\
      GC      AAAGGAA GAUCGUUGUGAUAUG      U
      CG      UUUCCUU UUAGUGACACUAUAC      
         CAAUA    -                 AAUCCU
``` |
| miR-6-1 | UAUCACAGUGGCUGUUCUUUUU | ```
         A-    C                        AG UAAUA\
      UUUA  UGUAGAGGAAUAGUGCUGUG UGUA A       U
      AAAU  AUGUUUUUUCUUGUCGGUGAC AUAU A      CU UACCA
         CC    U                        -
``` |
| miR-6-2 | UAUCACAGUGGCUGUUCUUUUU | ```
           C        UU UG  C       U - G
      UAACC AAGGGAAC  C   CUG UGAUAUA UA UU A
      GUUGG UUUUCUUG  G   GAC ACUAUAU AU AA A
           -        UC GU  -       C C A
``` |
| miR-6-3 | UAUCACAGUGGCUGUUCUUUUU | ```
        A                            U    AAAC\
   CAAA AGAAGGAACGUUCCUG UGAUGUAG UUG       U
   GUUU UUUUUUCCUUGUCGGUGAC ACUAUAU AAC     ACUC
        G                            -    
``` |
| miR-7 | UGGAAGACUAGAGAUUUGUUGU | ```
     U    U       U   U    -  UGGUC\
GAGUGCAU CCGUA GGAAGAC AG GAUUU      U
UUUACGUG GGCAU UCUUCUG UC CUAAA      ACAAUA UGGUU
     C    -       U   C    -  UGUUGU/
``` |
| miR-8 | UAAUACUGUCAGGUAAAGAUGUC | ```
          CUGUUC    -    G    C    AUUAGA  UCCUUU\
AAGGACAU        ACAUCUU ACC GGCAG CUGUC      U
UUCCUGUG        UGUAGAA UGG CUGUC UAAUCU     CAAUAU
          CCUGC-            A    A        
``` |

Fig.7 (cont.)

| | |
|---|---|
| miR-9 | UCUUUGGUUAUCUAGCUGUAUGA |
| miR-10 | ACCCUGUAGAUCCGAAUUUGU |
| miR-11 | CAUCACAGUCUGAGUUCUUGC |
| miR-12 | UGAGUAUUACAUCAGGUACUGGU |
| miR-13a | UAUCACAGCCAUUUUGAUGAGU |
| miR-13b-1 | UAUCACAGCCAUUUUGACGAGU |
| miR-13b-2 | UAUCACAGCCAUUUUGACGAGU |

(Hairpin secondary structure sequences shown adjacent to each miRNA entry)

Fig.7 (cont.)

| | | |
|---|---|---|
| miR-14 | UCAGUCUUUUCUCUCCUA | UGUGGGAG GAGA C GGGGACU C ACUGU GCUU \<br>AUAUCCUC CUCU U UUCUGA UGAUA A<br>            U     C           AAUU |
| miR-15a | UAGCAGCACAUAAUGGUUUGUG | GAGUAAAGUA UA GA U<br>CCUUG GCAGCACA AUGGUUUGUG AAA G<br>GGAAC CGUCGUGU UACCGGACGU GG A<br>      AUAAAAACUC UA |
| miR-15b | UAGCAGCACAUCAUGGUUUACA | U C C A A ACA \<br>CUG AGCAGCA AU AUGGUUU CAU CU<br>GAU UCGUCGU UA UACUAAG GUA GA G<br>  C U U      C     ACU |
| miR-16 | UAGCAGCACGUAAAUAUUGGCG | AG C - A CGUUA UCUA \<br>GUCAGC UGC UUAGCAGCAC GU AAUAUUGG AGAU A<br>CAGUUG AUG AGUCGUCGUG CA UUAUAACC UCUA A<br>      GA A          U A           - - - - UUAA |
| miR-16 | only different precursor | UC CU UA C AG AAU<br>GU CACU AGCAGCACG GU UGA A<br>CA GUGA UCGUCGUGU CA AUU U<br>  GU   UU         CA       A A- AUA |
| miR-17 | ACUGCAGUGAAGGCACUUGU | GA CA- A G - AUA \<br>GUCA AUAAUGU AAGUGCUU CA UGCAG UAG UG<br>CAGU UAUUACG UUCACGGA GU ACGUC AUC AC U<br>  GG         AUG       A      G   -    GUG |
| miR-18 | UAAGGUGCAUCUAGUGCAGAUA | CU U C U A UGAA AG<br>UGUU AAGG GCAU UAG GCAU GU A<br>ACGG UUCC CGUG AUC CGUA CG U<br>    UC       A      C      -   UA-- AU |

Fig.7 (cont.)

| | | |
|---|---|---|
| miR-19a | UGUGCAAAUCUAUGCAAAACUGA | ``` U   U              ----  AGA\ GCAG  CC CUGUUAGUUUUGCAUAG  UUGCAC  UACA    A CGUC  GG GGUAGUCAAAACGUAUC  AACGUG  AUGU  AAG      C    U              UA    UUG    ``` |
| miR-19b-1 | UGUGCAAAUCCAUGCAAAACUGA | ``` UU              UC  UGUGUG\ CACUG  CUAUGGUUAGUUUUGCA GG UUUGCA CAGC      A GUGAU  GGGUCAGUCAAAACGU CC AAACGU GUCG  UCUUAU           --              A  U       ``` |
| miR-19b-2 | UGUGCAAAUCCAUGCAAAACUGA | ``` CUAC          UUCA   GCGUAUA  U ACAUUG    UUACAAUUAGUUUUGCA GG UUUGCAU     UGUAUAU  U UGUAAU    AGUGUUAGUCAAAAACGU CC AAACGUG  UCGG    G               ----           A  U       ``` |
| miR-20 | UAAAGUGCUUAUAGUGCAGGUAG | ``` C  ACU  A-  AAGUGCUUAUAGUGCAG UAG UG  U GUAG   ACU    AAGUGCUUAUAGUGCAG UAG  UG  U CGUC  UGA  AA  UUCACGAGUAUUACGUC AUC AU  A      A             G       UG ``` |
| miR-21 | UAGCUUAUCAGACUGAUGUUGA | ``` A  A   UGUUG UGUCGGGUAGCUUAUC GACUG\  CUGU G\ ACAGUCUGGGGUAG CGUUGUCAAACGU ACAAC GGUA C UC      C              -          U       ``` |
| miR-22 | AAGCUGCCAGUUGAAGAACUGU | ``` U CC     -      A  U CCUG GGC GAG GCAGUAGUUCUUCAG UGGCA GCUUUA GU  \A CCG CUC CGUUGUCAAGAAGU ACCGU CGAAAU CG   A U C-    A           G         ACCC ``` |
| miR-23a | AUCACAUUGCCAGGGAUUUCC | ``` C  C  -      G  G CUUC   C GG CGG UGGGG UUCCUGG GAUG GAUUUG   U CC GCC ACCUU AGGGACC UUAC CUAAAC  ACUG   A  A           U         G  A       ``` |

Fig.7 (cont.)

| | | |
|---|---|---|
| miR-23b | AUCACAUUGCCAGGGAUUACCAC | ```
         C   U   -      -     C  GUGACU   U
      GG UGC UGG  GUUCCUGGCA UG UGAUUU     G
      CC ACG ACC  UAGGGACCGU AC ACUAAA   AUUAGA
         A   C   AU      U   -  
``` |
| miR-24-1 | UGGCUCAGUUCAGCAGGAACAG | ```
        G   G   A     UA    UCUCAU   U
     CUCC GU CCU CUGAGCUGA UCAGU
     GAGG CA GGA GACUUGACU GGUCA
        A   A   C          C-   CACAUU
``` |
| miR-24-2 | UGGCUCAGUUCAGCAGGAACAG | ```
       CC  CG   UGC   ACUGAGCUG  AA--  ACACAG   UU
     CUCUG UCC        ACUGAGCUG       ACACAG   G
     GGGAC AGG   ACG  UGACUCGGU  CACA  UGUGUU   G
       A-  --   ACU              -     CACA   UG
``` |
| miR-25 | CAUUGCACUUGUCUCGGUCUGA | ```
        A  AG   G   AGGC GAGAC  G GCAAU  UU G  ACG   C
     GGCC GUGUUG   UCUG  CUCUG    GUUCAUU CGUUA  GGUC  U
     CCGG CGUGAC   GGGCA GUUCAU  C CGUUA  GG UC  CCG   U
        C  AG  G   A    C       U UUA      CG   CG
``` |
| miR-26a | UUCAAGUAAUCCAGGAUAGGCU | ```
                     G    -   U   UC   AGGAUAGGUUG  GCAG  G
        AGGCC GUG CCUCGU CAAGUAA CCAGGAUAGGCUGU      U
        UCCGG CGC GGGGCA GUUCAUU GGUUCUAUCCGGUA      ACCC
              GA   C   -    U         CC
``` |
| miR-26b | UUCAAGUAAUUCAGGAUAGGUU | ```
              GA  -  U    UC    AGGAUAGGUUG    UGUG  C
        CCGG  CCC AGU CAAGUAAU  AGGAUAGGUUG          C
        GGCC  GGG UCG GUUCAUUA  UCUGUCCGAC          CUGU
            AG  C   -  -       CC
``` |
| miR-27a | UUCACAGUGGCUAAGUUCCGCU | ```
       A   A   A       U   G  UCCAC
     CUG GG GC GGGCUUAGCUGCU GUGAGCA  GG   A
     GAC CC CG CUUGAAUCGGUGA CACUGU CU     A
       C   C   C             -     G   GAACC
``` |

Fig.7 (cont.)

| | | |
|---|---|---|
| miR-27b | UUCACAGUGGCUAAGUUCUG | AGGUGCAGAGCUUAGCUG<sup>AUUG</sup> GUGAACAG<sup>UGAU</sup> UGG<sup>U</sup> GCC<sup>U</sup><br>UCCACGUCUUUGAAUCGGU CACUUGU UC-- U |
| miR-28 | AAGGAGCUCACAGUCUAUUGAG | C<sup>C</sup> CUUGCCCUC<sup>A</sup> AGGAGCUCACAGUCUA<sup>UG</sup> AGUUA<sup>U</sup> UCAGU<sup>CC</sup><br>GGU CUUGCCCUC AGGAGCUCACAGUCUA UG AGUUA U UCAGU CU<br>UCA GGACGGGAG UCCUCGAGUGUUAGAU AC C CCUU UCAGU<br>G C |
| miR-29a | CUAGCACCAUCUGAAAUCGGUU | UUU C UCAAU<br>AUGACUGAUUUC UGGUGUU AGAG<br>UAUUGGCUAAAG ACCACGA UCUU UUAAU<br>UCU |
| miR-29b | UAGCACCAUUUGAAAUCAGUGUU | A GCUGGUUUCA AUGGUG UUAGAU UUAAAU<br>AGGA GCUGGUUUCA AUGGUG UUAGAU UUAAAU<br>UCUU UGACUAAAGU UACCAC GAUCUG UUAGUG<br>G |
| miR-29c | UAGCACCAUUUGAAAUCGGuua | |
| miR-30a-s | UGUAAACAUCCUCGACUGGAAGC | A GUG A<br>GCG CUGUAAACAUCC GACUGGAAGCU GUG A<br>CGU GACGUUUGUAGG CUGACUUUCG CAC G<br>C GUAAA C |
| miR-30a-as | CUUUCAGUCGGAUGUUUGCAGC | A GUG A<br>GCG CUGUAAACAUCC GACUGGAAGCU GUG A<br>CGU GACGUUUGUAGG CUGACUUUCG CAC G<br>C GUAGA C |

Fig.7 (cont.)

| Name | Sequence | Hairpin Structure | Notes |
|---|---|---|---|
| miR-30b | UGUAAACAUCCUACACUCAGC | ```
        U  -        UCAUA
AUGUAAACAUCC ACA CUCAGCUG     C  A
UGCAUUUGUAGG UGU GGGUCGGU     UGCGU
        -  A
``` | |
| miR-30c | UGUAAACAUCCUACACUCUCAGC | ```
    UACU   U  ACA    C    GUGGAA      A
AGA   GUAAACA CCU CUCUCAGCU         G
UCU   CAUUUGU GGA GAGGGUCGA         AAGAAU
    UUCU   C  A--
``` | human |
| miR-30d | UGUAAACAUCCCCGACUGGAAG | ```
  U U   CCC     GUAAGA      C
GU GU GUAAACAUC GACUGGAAGCU      A
CA CG CGUUUGUAG CUGACUUUCGA      AUCGAC
  U U   A--
``` | |
| miR-31 | GGCAAGAUGCUGGCAUAGCUG | ```
     GA  G  C    U-  GAA    G
GGAGAG GGCAA AUG UGGCAUAGC GUU  U
CCUUUC CCGUU UAC ACCGUAUCG CAA  GGG
     UA  A  A    UC  CG G
``` | |
| miR-32 | UAUUGCACAUUACUAAGUUGC | ```
             U    -  UU  C
GGAGAUAUGCACAU ACUAAGUUGCAU G  GU A
CUUUUAUAGUGUG  UGAUUUAACGUA C  CG G
             -        A UC A
``` | |
| miR-33 | GUGCAUUGUAGUUGCAUUG | ```
         A UU  G   UUCU  UG
CUGUGGUGCAUUGU GCAUUGCAUG GG  G
GACACUACGUAACA UGUAACGUAC CC  G
         C UU         ----  AU
``` | chr8 human |
| miR-99a | ACCCGUAGAUCCGAUCUUGU | ```
   A   UC   CGA  U  G  AAG
CAUA ACCCGUAGA UCCGAUCUUGU UG  U
GUGU UGGGUAUCU GGCUAGAACGC GC  G
   C   UU         C  -  CAG
``` | |

Fig.7 (cont.)

| | | |
|---|---|---|
| miR-99b | CACCCGUAGAACCGACCUUGCG | GGCAC CC ACCCGUAGA AC C ---- C<br>CUGUG    UGGGUGUCU CGA CU UGCGG GG<br>CC       GU C ACAC   G U |
| miR-101 | UACAGUACUGUGAUAACUGA | UCAGUUAUCACAGUGCUG A GUCCA<br>AGUCAAUAGUGUCAUGAC UGCU U<br>          - AUGG AAAUC |
| miR-122a | UGGAGUGUGACAAUGGUGUUUGU | AGCUGU GG AGUGUGA C UGUCC A   woodchuck<br>UCGAUA    UCACACU AAUGGUGUUUG A<br>       AA         A UUACCGCAAAC UAUCA |
| miR-122b | UGGAGUGUGACAAUGGUGUUUGA | |
| miR-122a,b | UGGAGUGUGACAAUGGUGUUUG | |
| miR-123 | CAUUAUUACUUUUGGUACGCG | UGAC A GC CAUUAUUACUUU U CGCUG C<br>ACUG CG GUAAUAAUGAG UGGUACG UGA A<br>    G C         U GCCAUGC ACU C<br>                   UCAA- |
| miR-124a* | UUAAGGCACGCGGUGAAUGCCA | CUCU C GUGUUCAC A GA CCUUGAUU UAAUG<br>GAGA G CGUAAGUG GCG CGC AC GGAAUUAA U<br>    -    A-           G       CAUAU C |

Fig.7 (cont.)

| | | |
|---|---|---|
| miR-124b | UUAAGGCACGCGGGUGAAUGC | CUCU GUGUUCAC GCG CCUUGAUU CC A GA UAAUG AC021518<br>GAGA CGUAAGUG CGC GGAAUUAA AC G AC CAUAC U |
| miR-125a | UCCCUGAGACCCUUUAACCUGUG<br>potential lin-4 ortholog | CUGGGU CCUGAGA CCUU ACCUGUGA C C UA ---- A GG C<br>GGUCCG GGGUUCU GGAG UGGACACU A U -- GGGA CC G U |
| miR-125b | UCCCUGAGACCCUAACUUGUGA<br>potential lin-4 ortholog | GCCUAG CCUGAGA CCU ACUUGUGA UC C A GG- U UAU U<br>CGGAUC GGGUUCU GGA UGAACACU CA C ACA AUG A |
| miR-126 | UCGUACCGUGAGUAAUAAUGC | A U CGCUG C<br>GC CAUUAUUACUU UGGUACG UGA A C<br>CG GUAAUAAUGAG GCCAUGC ACU C<br>C U UCAA- U |
| miR-127 | UCGGAUCCGUCUGAGCUUGGCU | A U G G C AG<br>CC GCC GCU AAGCUCAGA GG UCUGAU UC --<br>GG UGG CGG UUCGAGUCU CC AGGCUA AG A<br>C U - G U CU AA |
| miR-128 | UCACAGUGAACCGGUCUCUUUU | UUC UAC CU U<br>GUUGGA GGGGCCC CACUGU GAGAGGU U<br>CGACUU CUCUGGG GUGACA CUCUUUA A<br>UUU CAA - C |
| miR-129 | CUUUUUUCGGUCUCUGGGCUUGC | - C CU G UUCCU C human<br>GGAU CUUUUUG GGU GGGCUU CUG CU A GA A<br>UCUA GAAAAAC CCA CCCGAA GAC GA C<br>U C UU G UGAU- |

Fig.7 (cont.)

| | | |
|---|---|---|
| miR-130 | CAGUGCAAUGUUAAAGGGC | - C A GUCUAAC<br>GA GCUCUUU ACAUUGUGCU CU \\ G<br>CU CGGGAAAA UGUAACGUGA GA GCCAUGU<br>A U C |
| miR-131 | UAAAGCUAGAUAACCGAAAGU | G C G U A<br>GUU UUAU UUUGGUUAUCUAGCU UAUGAG GU U<br>CAA AAUG AAGCCAAUAGAUCGA AUACUU UG U<br>A A A C G |
| miR-132 | UAACAGUCUACAGCCAUGGUCGU | A UUC G- G<br>GGGC ACCGUGGCU GAUUGUUACU UGG \\<br>CCCG UGGUACCGA CUGACAAUGG GCC A<br>C CAU AG UC |
| miR-133 | UUGGUCCCCUUCAACCAGCUGU | AA U A GCCUC<br>GCUA AGCUGGU AA GG ACCAAAUC U<br>CGAU UCGACCA UU CC UGGUUUAG U<br>G AC C C GUAAC |
| miR-134 | UGUGACUGGUUGACCAGAGGGA | GU U A- G GCGU AC \\<br>AGGGU GUGACUGG UG CCA AGGG GC U<br>UCCCA CACUGAUC AC GGU UCCC UG UC<br>AC C CG G ACU- |
| miR-135 | UAUGGCUUUUUAUUCCUAUGUGAA | UU UUCUAU \\<br>CUAUGGCUUU AUUCCUAUGUGA U<br>GGUGCCGAGG UAGGGAUAUACU<br>U- CGCUCG |
| miR-136 | ACUCCAUUGUGUUUGAUGAUGGA | C UUU UUCU \\<br>GAGGACUC AUUUG UGAUGAUGGA U<br>CUUCUGAG UAAAC GCUACUACCU<br>- UCU CGAA |

Fig. 7 (cont.)

| | | |
|---|---|---|
| miR-137 | UAUUGCUUAAGAAUACGCGUAG | ```
            G  G                A     - GA
CUUCGGGU ACG GUAUUCUUGGUGG  UAAUA CG    U
GGAGCUG UGC CAUAAGAAUUCGUU AUUGU GC    AU
        A  G                -     U  U
``` |
| miR-138 | AGCUGGGUGUUGUGAAUC | ```
         UCA   AC- C  CG
CAGCU GGUGUUGUGAA  GGCCG GAG AG  C
GUUGG CCACAGCACUU  UCGGC UUC UC  A
     GA           UA- _  -  CU
``` |
| miR-139 | UCUACAGUGCACGUGUCU | ```
     G             A              GUGGC\
GU UAUUCUA CAG GC CGUGUCUCCAGU         U
CA AUGAGGU GUC CG GCGCAGAGGUCG      GAGGC
     -  U A   -                      human
``` |
| miR-140 | AGUGGUUUUACCCUAUGGUAG | ```
       A      UU  UC
CCUG CC GUGGUUUUACCCU UGGUAGG ACG A
GGAC GG CACCAAGAUGGGA ACCAUCU UGU U
     A -             C       --  CG
``` |
| miR-141 | AACACUGUCUGGUAAAGAUGG | ```
     U       -       AU GAAG\
GGG CCAUCUU  CCAG GCAGUGUUGG GGUU  U
CCC GGUAGAA  GGUC UGUCACAAUC UCGA AGUA
     -       AU       -     C-
``` |
| miR-142s | CAUAAAGUAGAAAGCACUAC | ```
      A  UAA--- G
AC-  CCAUAAAGUAG AAGCACUAC CA C
     GGUAUUUCAUC UUUGUGAUG GU A
GUA                        UGGGAG C
                            C
``` |
| miR-142as* | UGUAGUGUUUCCUACUUUAUGG | ```
      A  UAA--- G
AC-  CCAUAAAGUAG AAGCACUAC CA C
     GGUAUUUCAUC UUUGUGAUG GU A
GUA                        UGGGAG C
                            C
``` |

Fig.7 (cont.)

| | | |
|---|---|---|
| new | AUAAGAGAGCAAAAGCUUGU | ``` G         G C  GG    C  AU\ UGAC  GGCGAGCUUUU  GC CG  UUAUAC UG ACUG  UUGUUCGAAAA  CG GC  AAUAUG AC G G                A  A  AG      C  UC ``` |
| miR-143 | UGAGAUGAAGCACUGUAGCUCa UUAGAUGAAGCACUGUAG | ``` G       G    U - AG CCUGAG UGCAGUGCU CAUCUC GG UC U GGACUC AUGUCACGA GUAGAG CU AG U G         A  U   G GG ``` AL049829.4 |
| miR-144 | UACAGUAUAGAUGAUGUACUAG | ``` G    A   A-    GU GGCUGG AUAUCAUC UAUACUGUA  GUUU G CGAUC UGUAGUAG AUAUGACAU CAGA A A        -         CA   GU ``` |
| miR-145 | GUCCAGUUUUCCCAGGAAUCCCUU | ``` C  UC  CAGU UU C  UGGAUG\ CUCA GG   U C CCAGGAAUCCCU      C GAGU UC  GUCA AA GGUCCUUAGGGG UAGAAU   -  UU      -              ACUGU ``` |
| miR-146 | UGAGAACUGAAUUCCAUGGGUUU | ``` CU          C  AUAUC AGCU GAGAACUGAAUU CAUGGGUU A UCGA UUCUUGACUUAA GUGUCCAG A C-                            A ``` |
| miR-147 | GUGUGUGGAAAUGCUUCUGCC | ``` A- CAA  CAUUUCUGCACAC ACA--- GA\ CCA C AAUCUA AGA  GUAAAGGUGUGUG        GGU AU UUAGAU UCU                ACCGAA    CG UC-                    A ``` | human |
| miR-148 | UCAGUGCACUACAGAACUUUGU | ``` -  A-  CC - AGU\ GAGGCAAAGUUCUG AG  CACU GACU CUG A CUCUGUUUCAAGAC UC  GUGA CUGA GAU A        A  AC      --         A  AGU ``` | human |

Fig.7 (cont.)

| miR-149 | UCUGGCUCCGUGUCUUCACUCC | GGCUCUG G C G A GUG G UCUUC CUCCC UUU U<br>UCGGGGC GAG CA GGAGG GAGGG GAG C<br>G A G - AG- C |
|---|---|---|
| miR-150 | UCUCCCAACCCUUGUACCAGUGU | CCCUGUCUCCCA AC U CCU GUACCAG UG- UG<br>GGGAUAGGGGGU CC CA CAUGGUC CUG C<br>A - GGA - GAC UC<br>A CCA C |
| miR-151 | CUAGACUGAGGCUCCUUGAGGU | C CA UGUCU<br>CCUG CCUCGAGGAGCU CAGUCUAGUA<br>GGAC GGAGUUCCUCG GUCAGAUCAU C<br>A A CCCUC |
| miR-152 | UCAGUGCAUGACAGAACUUGG | CCGGGCCUAGGUUCUGU G A CC CGG C<br>GGCCCGGGUUCAAGACA AU CACU GACU GCU U<br>UA GUGA CUGA CGA G<br>G C - - --- G |
| miR-153 | UUGCAUAGUCACAAAGUGA | GU A- AAU<br>CAGUG UCAUUUUGUGAU UGCAGCU GU \<br>GUUAC AGUGAAAACACUG ACGUUGA CG A<br>AU CC AGU<br>U |
| miR-154 | UAGGUUAUCCGUGUUGCCUUCG | U - CCU-- UUU<br>GAAGAUAGGUUA CCGUGU UG UCGC \<br>UUUUUAUCCAGU GGCACA AC AGUG A<br>U U UAAGC UUU |
| miR-155 [BIC-RNA] | UUAAUGCUAAUUGUGAUAGGGG | U U A UUGGCC \<br>CUGUUAAUGCUAAU G G UAGGGGU U<br>GACAAUUACGAUUG U C AUCCUCAG<br>- C - UCAGUC |

Fig.7 (cont.)

| name | sequence | structure |
|---|---|---|
| miR-C1 | AACAUUCAACGCUGUCGGUGAGU | ```
     U  A  U     CU     A  GGGAUUCA
CCA GG ACA UCAACG GUCGGUG GUUU       A
GGU CC UGU AGUUGC CAGCCAC CAAA       A
     U  A  C     -      -  AAAACAAA
``` |
| miR-C2 | UUUGGCAAUGGUAGAACUCACA | ```
   UU    UGG   UCA     UAAGGU
ACCAU UUGGCAA UAGAAC CACCGG      A
UGGUA AACCGUU AUCUUG GUGGCC      A
   UC    CAG   ---    CAGGGU
``` |
| miR-C3 | UAUGGCACUGGUAGAAUUCACUG | ```
    G       AC--  GA     AC        A  A
CUGU UAUGGC    UGGUA AUUCACUG UGA    G
GACA AUACCG    ACCAU UAAGUGAC ACU    CU
    A       GGAA  -      -  UG    G
``` |
| miR-C4 | CUUUUUGCGGUCUGGGCUUGUU | ```
-    CUUUUUG GGU G GGGCUU CUG G UUUU C
UGGAU       GGU   GGGCUU     CUG   CU G
AUCUA GAAAAAC CCA CCCGAA GAC A GAA C
U    C       UU     -      GA   U
``` |
| miR-C5 | UGGACGGAGAACUGAUAAGGGU | ```
  U   C    AG    -   UG
CCU UCCUUAUCA UUUUCC CCAGC UUUG A
GGA GGGAAUAGU AAGAGG GGUUG GAAU C
  U   C    U     CA    U   CU
``` |
| miR-C6 | UGGAGAGAAAGGCAGUUC | ```
            A     G        AU  UC  C  C
AGGGAUUGGAG GAAAAG CAGUUCCGUG GG   CC C
UUCCUGGUCUC CUUUUC GUCGGGAC   CC   -- UC
            -     G        --
``` |

Fig.7 (cont.)

| name | sequence | structure |
|---|---|---|
| miR-C7 | CAAAGAAUUCCUUUGGGCUU | ```
          U    UU   UCUCAU
     ACUUUCCAAAGAAUUC CCUU GGGCUU     U
     UGAAGGGUUUUUUAAG GGAA CCCGAA     U
          U    U-        UUUUAU
``` |
| miR-C8 | UCGUGUCUUGUGUUGCAGCCGG | ```
         A  A     C        CGCUGC
     UC GGCU CAACACAGGAC CGGG      U
     GG CCGA GUUGUGUUCUG GCUC      C
         -  C        U        CCCAGU
``` |
| miR-C9 | UAACACUGUCUGUAACGAUGU | ```
                            C  UU  UUG
     GGGCAUC UUACCGGACACAGUG UGGA UC    G
     CUUGUAG AAUGGUCUGUCAC AUCU AG    UUC
                 C        A    C-    UUC
``` |
| miR-C10 | CAUCCCUUGCAUGGUGAGGGU | ```
       CA  UC     GU        U
     UCU CA CCUUGCAUG GGAGGG    C
     AGG GU GGGACGUAC CCUCCC    C
       AC  UU     AC        CAAAAGU
``` |
| miR-C11 | GUGCCUACUGAGCUGACAUCAGU | ```
       G  G   A    UA  UCUCAU
     CUCC GU CCU CUGAGCUGA UCAGU    U
     GAGG CA GGA GACUUGACU GGUCA    C
       A  A   C    C-  CACACU
``` |
| miR-C12 | UGAUAUGUUUGAUAUAUUAGGU | ```
          UA---        UU
     CUGUG GAUAUGUUUGAUAUAU GGUUG    A
     GACAU UUAUACGAACUAUAUA CUAAU    UU
          CC           UCAAC   A
``` |

Fig.7 (cont.)

| name | sequence | structure |
|---|---|---|
| miR-c13 | CAACGGAAUCCCAAAAGCAGCU | C    C  AA      UU -  C<br>AGCGGG AACGGAAUCC AA GCAGCUG GU CU C<br>UCGUCC UUGCUUUAGG UU CGUCGAC UA GA A<br>      C          -  CA       CU C G |
| miR-c14 | CUGACCUAUGAAUUGACA | C  -    A          UGCUCUC<br> UGACCUAUG AAUUG CAGCCAG      G<br> ACUGGAUAC UUAAC GUCGGUC      U<br>-         C    C        UCCCCUC |
| miR-c15 | UACCACAGGGUAGAACCACGGA |    -   G       A          UU  UC<br>UCCUG CCG UGGUUUACCCU UGGUAGG ACG A<br>AGGAC GGC ACCAAGAUGGA ACCAUCU UGU U<br>   A         C              - -  CG |
| miR-c16 | AACUGGCCUACAAAGUCCCAG |   A   U    C    A  A       AGU<br>GAG GCUGGG CUUUG GGGC AG UGAG   G<br>CUC UGACCC GAAAC UCCG UC ACUU   U<br>  C      U     A    G  A       GAC |
| miR-c17 | UGUAACAGCAACUCCAUGUGGA |  U     A          G      - -    U<br>AUCGGG GUAACAGCA CUCCAU UGGA CUG G<br>UAGUCU CAUUGUCGU GAGGUG ACCU GGC C<br>     U            C         -     UA  U |
| miR-c18 | UAGCAGCACAGAAAUAUUGGC |  U     A-              UG GAA    G   U<br> AGCAGCACAG AAUAUUGGCA    GG  CU    G<br> UCGUCGUGUC UUAUAACCGU    CU  --    GAG<br>               GG |

Fig.7 (cont.)

| name | sequence | structure |
|---|---|---|
| miR-C19 | UAGGUAGUUUCAUGUUGG | ```
          A  A   C          GGCCUGGG
GUGAAUU GGU GUUU AUGUUGUUG          U
CACUUAG CCA CAAA UACAACAAC          U
          C  C   U          ACAAGUCU
``` |
| miR-C20 | UUCACCACCUUCUCCACCCAGC | ```
          C  A   CA    GA   -   A
GGCUGUGC GGGU GAGAGGG GUGG  GGU AAG G
CCGGUACG CCCA CUCUUCC CACU  CCA UUC C
          A  C   AC    UC   C   U
``` |
| miR-C21 | GGUCCAGAGGGGAGAUAGG | ```
     G  -  C G   U   UUCCUG
UCAUU  G UC A AGGGGAGA AGG   U
AGUAA  U AG U UCUCUUCU UCC   G
     A  -  A A   -   UUUUUA
``` |
| miR-C22 | CCCAGUGUUCAGACUACCUGUU | ```
   AAC     U    C   U  G---  G
GCC   CCAGUGU CAGACUAC UGU CA  GAG \
CGG   GGUUACA GUCUGAUG ACA GU  CUC C
   AUU     C    -   U  GUAA  U
``` |
| miR-C23 | UAAUACUGCCUGGUAAUGAUGAC | ```
   GGC   -    C   UAGUG
GCCGU  CAUC UUACUGGGCA AUUGGA U
CGGCA  GUAG AAUGGUCCGU UAAUCU C
   U     U    A   CUAGU
``` |
| miR-C24 | UACUCAGUAAGGCAUUGUUCU | ```
        U   U   UUC   A
UACCUUAC CAG AAGGCAUUGUUC  UAU U
AUGGGAUG GUC UUCCGUGACAAG  AUA U
        U   U   UAA   A
``` |

Fig.7 (cont.)

| name | sequence | structure |
|---|---|---|
| miR-C25 | AGAGGUAUAGCGCAUGGAAGA | ``` U        A-   UG   C<br>GUUCC UUUUCCUAUGC  UAUACUUCUU UGGAU \<br>CGAGG AGAAGGUACG  AUAUGGAGAA AUCUG U<br>     U            CG       --    G``` |
| miR-C26 | UGAAAUGUUUAGGACCACUAG | ``` C      U  G   A    C  U<br>GGUC AGUGGUUCU GACA UUCA CAGUU UG \<br>CCAG UCACCAGGA UUGU AAGU GUUAA AC A<br>    A        U    A    -     C  G``` |
| miR-C27 | UUCCCUUUGUCAUCCUAUGCCUG | ``` U    A    U  GAGAAUA \<br>UGGAC UCCCUUUGUC UCCUA GCCU     U<br>ACUUG AGGGAAACGG AGGGU CGGA     <br>     C    A    U   -   GGAAGUA``` |
| miR-C28 | UCCUUCAUUCCACCGGAGUCUG | ``` UC   C      UCUUA<br>CUCUUG CUUCAUUCCAC GGAGUCUG  G<br>GAGGAC GAAGUAGGUG CUUUAGAC   <br>     UC   A      CAACC``` |
| miR-C29 | GUGAAAUGUUUAGGACCACUAGA | ``` U  C    U  G   A    C  U<br>GCC GGUC AGUGGUUCU GACA UUCA CAGUU UG \<br>CGG CCAG UCACCAGGA UUGU AAGU GUUAA AC A<br>  C    A        U    A    -     C  G``` |
| miR-C30 | UGGAAUGUAAGGAAGUGUGUGG | ```                             C  U  AUAUC \<br>CCAGG CCACAUGCCUUCUUUAUAU C CAUAG      U<br>GGUUU GGUGUGUAAGGAAGUGA G GUAUC       <br>    U                        A  -  ACGAC``` |

Fig.7 (cont.)

| name | sequence | structure |
|---|---|---|
| miR-C31 | UACAGUAGUCUGCACAUUGUU | ```
       AUC     U     C              G
    GCC   CCAGUGU CAGACUAC UGU  UCAG A
    CGG   GGUUACA GUCUGAUG ACA  GGUC G
       AUU     C     -    UGUACAG  G
``` |
| miR-C32 | CCCUGUAGAACCGAAUUUGUGU a miR-10 variant | ```
        A  G   C            UG- AC
   UAUAU CCCU UAGAA CGAAUUUGUG  GU  C
   AUAUA GGGG AUCUU GCUUAGACAC  UA  C
        A  -   A            UGA CA
``` |
| miR-C33 | AACCCGUAGAUCCGAACUUGUGA A a miR-99a variant | ```
        A  C   C   A  CUUGUG UG U
   CACA ACC GUAGAU CGA      UG  C AU
   GUGU UGG UAUCUG GUU      AC  G C
        A  U   A   C  GAACAC -  GU
``` |
| miR-C34 | GCUUCUCCUGGCUCUCUCCCUC | ```
        C  U  UUG            -   GGAG
   AAGG AGGGG GAGGGG CGGGAGGAGC CGGGC  G
   UUCC UCUCC CUCCUC GUCCUCUUCG GUUCG  C
        -  C  UCG            C   GCGU
``` |

Fig. 7 (cont.)

| name | human | C.elegans | \ mouse \ | | | | | | | Drosophila | fugu fish | zebrafish |
| --- | --- | --- | --- | --- | --- | --- | --- | --- | --- | --- | --- | --- |
| | | | liver | small intes | colon | cerebellum | cortex | midbrain | heart | spleen | | | |
| let-7a-1 | AC007924 chr9 AC087784 chr 17 identical precursor | | num.hits in trace date, 3 families of similar precursors | | found | | nearly identical precursor | found | | | | | |
| let-7a-2 | AP001359 chr11 | | | | | | nearly identical precursor | | | | | | |
| let-7a-3 | AL049853 chr22 | AF274345 chrX with diff. precursor | | | | | | | | | | | |
| let-7b | AL049853 chr22 | | nearly identical precursor | | | nearly ident precursor trace#8311003 | | found | | EST AI481799.1 spleen = cerebellum (mammary) | | with slightly diff precursor | |
| let-7c | AP001667 chr21 | | identical and diff. precursors | | | num.genomic hits, ident precursor;diff precursor -> EST AI614897 | numerous genomic hits | found | | | AE003659 diff. Precursor | | |
| | | | | | | | | | found | | | | |
| let-7d | AC007924.3 chr9 AC087784 chr17 identical | | | | found | trace#8358704 nearly ident prec | trace#8358704 2 nearly ident prec | found | | | | | |

| | | | | | | | | | | | |
|---|---|---|---|---|---|---|---|---|---|---|---|
| let-7e | AC018755 chr19 | | | | | found | FOUND | | | | |
| let-7f-1 | AC007924 chr9 AC087784 chr17 | | ident precursor genomic DNA | | | found | found | | | | |
| let-7f-2 | AI592046 chrX | | ident. precursor in mmtrace 18713911 | | | | | | | | |
| let-7g | precursor ident. to mouse in AC092045.2 chr3 | | genomic hits, no EST | | | found | | | | | |
| let-7h | | | | found in cortex, no db hit | | | | | | | |

Fig.7 (cont.)

Fig.7 (cont.)

| | | | | | | | | | |
|---|---|---|---|---|---|---|---|---|---|
| let-7i | precursor ident. to mouse [AL117383.19]; also AC048341.22 | | found, supported by EST BB661268 | | | | | | |
| miR-1 | | | | | | | 2L,AE003667 | | |
| miR-1b | AL449263.5 chr20 nt1-21 | U97405.1 nt 1-21 (22G) | no mouse hit (only nt1-21) | | | found | | | |
| miR-1c | | | | | | found | | | found, but no db hit |
| miR-1d | AL449263.5 chr20 nt1-22 (23G) | | | | | found | | trace hits(nt1-23) trace#91 523974 | BF157601.1 with C23 (diff. precursor) |
| miR-2a-1 | | | | | | | 2L,AE003663 | | |

| | | | | |
|---|---|---|---|---|
| miR-2a-2 | | 2L,AE003663 | | |
| miR-2b-1 | | 2L,AE003620 | | |
| miR-2b-2 | | 2L,AE003663 | | |
| miR-3 | | 2R,AE003795 | | |
| miR-4 | | 2R,AE003795 | | |

Fig.7 (cont.)

Fig.7 (cont.)

| | | | | | | | | | | | |
|---|---|---|---|---|---|---|---|---|---|---|---|
| miR-5 | | | | | | | | | 2R,AE003795 | | |
| miR-6-1 | | | | | | | | | 2R,AE003795 | | |
| miR-6-2 | | | | | | | | | 2R,AE00379 | | |
| miR-6-3 | | | | | | | | | 2R,AE00379 | | |
| miR-7 | AC003791 chr19 diff.precursor; EST BF373391 again different | | | | not cloned, but mouse EST predicts precursor similar to human | | | | 2R,AE003791 | | |
| miR-8 | | | | | | | | | 2R,AE003805 | | |

| | | | | | |
|---|---|---|---|---|---|
| miR-9 | AC005316 chr15 AC026701 chr5 each with diff. precursor | | AF155142.1 chr19 diff prec.sligh.diff prec.s in trace hits | found | 3L,AE003516 2diff precurs scaffold 3868 and 2417 |
| miR-10 | AF287967 chr11 (HOX B4/B5) | | | | AE001574 |
| miR-11 | | not found, but AC011194 chr.11 predicts diff. precursor | | | 3R,AE003735 |
| miR-12 | | | | | X,AE003499 |
| miR-13a | | | | | 3R,AE003708 |

Fig.7 (cont.)

Fig.7 (cont.)

| | | | | | | | | | | | | |
|---|---|---|---|---|---|---|---|---|---|---|---|---|
| miR-13b-1 | | | | | | | | | 3R,AE003708 | | | |
| miR-13b-2 | | | | | | | | | X,AE003446 | | | |
| miR-14 | | | | | | | | | 2R,AE003833 | | | |
| miR-15a | 13, AC069475 | | | | | found | trace#72 137197 prec slig diff | | | | | |
| miR-15b | | | | | | | trace#79 105069 | | | | | |

| | | | | | | | | | |
|---|---|---|---|---|---|---|---|---|---|
| miR-16 | 13, AC069475 interesting leukemia locus | | | | | found | | | AL606727 diff precurs |
| miR-16 | 3, NT_005740.6 | several trace, nearly ident precursor | found | genomic hits with 2 slightly diff precur.trace#502 93836,78368680 | found trace#7910506 9;nearly ident prec. as in human | | | | |
| miR-17 | 13, AL138714 | | | | | | | | |
| miR-18 | 13, AL138714 | | | | | | | | |
| miR-19a | 13, AL138714 | | | | | | found | | |
| miR-19b-1 | 13, AL138714 | | | | | | | | G46757 with a U9C |

Fig.7 (cont.)

Fig.7 (cont.)

| | | | | | | | | | |
|---|---|---|---|---|---|---|---|---|---|
| miR-19b-2 | X, AC002407 | | | | | | | | |
| miR-20 | 13, AL138714 | | found | | | | | | |
| miR-21 | 17, AC004686 | AL604063 chr11, near ly ident precursor | found | | | | | | |
| miR-22 | several highly similar ESTs: AW961601 shown | cDNAa from var. tissues, ide ntical precursor | AK008813 cDNAs, same precursor | AK008813 (cDNA), prec ident to human | | found | | | |
| miR-23a | 19, AC020916 | | | | | found | found | | |
| miR-23b | XM_072557.1 chr9,also human ESTs,prec nearly ident to mouse | | | EST AW124037 hypothal,EST AI848465 cerebellum | | found trace#62 540691 prec sli diff | found | three hits in db | |

| | | | | | | | |
|---|---|---|---|---|---|---|---|
| miR-24-1 | 9, AF043896 | | found | | | | |
| miR-24-2 | 19, AC020916 | | | found.EST AI286629 (thymus): nearly ident. to miR-24-1; EST AA111466 (whole embryo) different precursor | found | found | |
| miR-25 | 7, AC073842 second ident. copy found in chr7 | predicted in mouse (EST AI595464), but not cloned | | | | | |
| miR-26a | 3, AP000497 | | | AC055818.9,trf ace#8471973 precursor diff. from human | found | | Scaffold_4097 different precursor |
| miR-26b | 2, AC021016 | found | found,trace#6986 6494,slight.diff precursor | | | | |

Fig.7 (cont.)

Fig.7 (cont.)

| | | | | | | | | |
|---|---|---|---|---|---|---|---|---|
| miR-27a | 19, AC020916 | | found | found, but no hit | found, but no db hit for mouse | found | found | found | |
| miR-27b | XM_098943.1 chr9 identical precursor | | | | | found, maps to chr 13 MGSC mmtrace 44671617 | | | |
| miR-28 | 3, AC063932 | | | | | | | | |
| miR-29a | 7, AF017104 second ident.copy found in chr7 CLUSTER, this cluster also consvd in mouse: AC024913.32 | | found, AC024913.32 | found, mmtrace#23467334 | nearly ident precursor trace#23467334, EST AC024913.32 | | trace, EST, nearly ident prec | | |
| miR-29b | AL035209.1 chr1 CLUSTER of miR-29-b and 29-c; miRNA similar to miR-83 | | found | | AC024913.32;d iff precursor in EST BG342396 (retina) | found | FOUND | | Scaffold 17670.(a third copy) |

| | | | | | | |
|---|---|---|---|---|---|---|
| miR-29c | | | | | | |
| miR-30a-s | nearly ident fold in AL035467.23 chr6 | found;ESTs trace6802 ,3889 all with 22G | | found | found | |
| miR-30a-as | 6, AL035467 | | found with diff. precursor in trace #85261735 | found | | found, supportd by ESTs |
| miR-30b | human AF159227.6 chr8,different precursor | | trace#7239251 | found | | |
| miR-30c | AL136164.8 chr.6 supported by ESTs (BF594736.1) | | found,but no db hit for mouse | | found | found |

| | | |
|---|---|---|
| | | Scaffold 17670 has two copies of this RNA |
| found | | |
| | | |
| found | | Scaffold 3483,diff precursor |
| found | | |

Fig.7 (cont.)

Fig.7 (cont.)

| | | | | | | |
|---|---|---|---|---|---|---|
| miR-30d | AF159227.5 chr8 | | | | Scaffold 3483,diff fold | |
| miR-31 | 9, AL353732 | | | found, but no mouse db hit | | |
| miR-32 | 9, AL354797 | | | | | |
| miR-33 | 22, Z99716 | | trace#4891071 4 | | G44780 with diff.precu rsor | |
| miR-99a | AP000962.2 chr21,ident to mouse;[similar to miR-10 and miR-51] | | mmtrace #92340982 | | | |
| miR-99b | AC018755.3 chr.19; [similar to miR-10 and miR-51] | | | | | |

| | | | | | | |
|---|---|---|---|---|---|---|
| miR-101 | AL158147.17 chr9 diff precursor | | AK021368.1 cDNA eyeball | found | | U53213.1 T.fluviatilis |
| miR-122a | abundant but no db hit, except woodchuck x13234 | | | | | |
| miR-122b | | | | | | |
| miR-122a,b | | | | | | |
| miR-123 | genomic hits (trace#6108147), no EST | | | | | Scaffold_3295 |

Fig.7 (cont.)

Fig.7 (cont.)

| | | | | | | | |
|---|---|---|---|---|---|---|---|
| miR-124a* | nearly ident. precursor in chr8[AC021518] chr20[AL096828] | found in z72504.1 chrIV intron,diff precursor | found | most abundant in cereb.,genomic hits (trace#21097008, 11137241) | most abundant;several trace hits;precurs= cerebellum | found | slightly diff precursor AC009251 chr2L |
| miR-124b | AC021518 chr8,nearly ident chr20 AL096828.29 | | | found, but no db hit | found | | |
| miR-125a | ident precur in AC018755.3 chr 19 | | | genomic hits trace#33921945, 48262259 and more | found | | |
| miR-125b | AP001359.4 chr11 AP001667.1 chr21 (chr21 like mouse) | | | | trace#8398570 5 | found with A22U | found in AC006590.1 2358 1 with diff fold |
| miR-126 | | | | mmtrace#3521597 and more | | found | |
| miR-127 | human AL117190.6 chr.14 same precurs as in mouse | | | hit in trace#7951437 | | | with diff precursScaffold_32 95 |

| | | | | | | | | |
|---|---|---|---|---|---|---|---|---|
| miR-128 | ident in AC016742.10 chr 2;diff prec in AC016943.7 chr.3 | | | | genomic hit trce#51670230 | found | | |
| miR-129 | human AC018662.3 chr7 | | | | found, but no db hit | | | Scaffold 828,diff prec |
| miR-130 | | | | | mmtrace 68479278 | | | |
| miR-131 | AC005317.2 chr 15 sligh.diff precursor,but AC026701.6 chr 5 ident | | | | several trace hits,mouse AF155142 | found | | with diff fold AC091299.2 |
| miR-132 | AL137038.5 chr17 prec sligh.diff from mouse | | | | trace hit#86984641 | | | |

Fig.7 (cont.)

Fig. 7 (cont.)

| | | | | | | |
|---|---|---|---|---|---|---|
| miR-133 | AL391221.15 chr6 diff. Precursor(ident to rat L33722.1) | | found, trace# 62407955 | found | AC093440.1 diff. Precursor | Scaffold 1049;precu nearly like mouse |
| miR-134 | AL132709.5 chr14 similar precursor | | trace#6462031 1 | | | |
| miR-135 | AC092045.2 chr3 AC018659.35 chr12 (ident or simil to mouse) | | trace#7149523 5,ESTBF780995 .1(kidn.,sple en)(=chr3huma n) | found | | Scaffold 2125 with similar precurs |
| miR-136 | AL117190.6 chr14 ident to mouse | | trace#8607175 3 | | | |
| miR-137 | AC027691.1 chr1 ,ident to mouse,nearly ident fish | | trace#8977454 3,EST (hypothal)AI8 52436.1,ident. | | | Scaffold 18244 – nearly ident to mouse/man |
| miR-138 | AC006058.1 chr3 precursor diff | | mouse EST BB528620.2 | | | |

| | | | | | | | | |
|---|---|---|---|---|---|---|---|---|
| miR-139 | AP003065.2 chr11 | | | | | | | |
| miR-140 | AC026468.8 chr.16, precursor nearly ident, | several trace hits; trace#10530393 | | found, but no mouse hit | | | | |
| miR-141 | AC006512.12 chr12, precursor slightli diff | AC002397 chr6 | | | | | | |
| miR-142s | AC004687.1 chr17 BCL3/myc translocation locus, like mouse | found | found | | | found | | |
| miR-142as* | | several EST AI153235 | found | | | found | | |

Fig.7 (cont.)

Fig.7 (cont.)

| | | | | | | | | | |
|---|---|---|---|---|---|---|---|---|---|
| new | AL049829.4 chr14 | | | | | found but no db hit | | | |
| miR-143 | AC008681.7 chr5 | | | found, but no db hit | found | found | | | |
| miR-144 | XM_064366.1 precursor nearly ident | | found | | | EST AA290206 .1,trace 2143909 | | | |
| miR-145 | AC008681.7 chr5 GG->GA;precur nearly like mouse, see 2 positions above | | | | | found EST BF163348 .1 lung | | Scaffold 934 similar | |
| miR-146 | AC008388.7 chr5 diff precursor | | | | | trace#34 639321 | | | |
| miR-147 | AL592549.7 | | | | | | found | | |

| | | | | | | | | | | | | |
|---|---|---|---|---|---|---|---|---|---|---|---|---|
| miR-148 | AC010719.4 | | | | | | | | | | | |
| miR-149 | | | | | | | | | | | found, no db hit | |
| miR-150 | | | trace#8472 1065,10352 801 | | | | | | trace#85 955550 | | | |
| miR-151 | | | trace#8845 6669 | | | | | | | | | |
| miR-152 | human chr 17 AC004477.1, nearly identical | | found in colon,supportd.by trace#83700445;close match MGSC in chr18 (additional 14C unlikely, not supported by trace and | | | | | | | | | |

Fig.7 (cont.)

Fig.7 (cont.)

| | | | | | | | | | | | |
|---|---|---|---|---|---|---|---|---|---|---|---|
| miR-153 | AC006372.2 chr7 ident.precursor | | | | | | found sever. mmtrace 87010874 | | | | |
| miR-154 | AL132709.5 chr14 nearly identical precursor | | | | | | found sever. mmtrace 86715639 | | | | |
| miR-155 [BIC-RNA] | human BIC RNA:AF402776.1 (has U12C) | | | found; chr 16 mouse | | | | | | | |

Fig.7 (cont.)

| name | human | | mouse | | | | | | | Drosophila | fugu fish | zebrafish |
|---|---|---|---|---|---|---|---|---|---|---|---|---|
| | | spleen | eye | kidney | testes | lung | thymus | skin | | | |
| miR-C1 | with different precursors in chr9 AL158075.11,chr1 AL136321.5 | | mouse trace #76647842 | | | found | | found | | scaffold_1819 | |
| miR-C2 | chr7 AC084864.2 similar precursor | | mouse trace #88841093 | | | | | | | scaffold_967 | AI590150.2 |
| miR-C3 | chr7 AC084864.2 ident.precursor | | trace #86029980 | | | | | | | scaffold_967 | AI590150.2 |
| miR-C4 | similar precurs.in chr7 AC018662.3 | | trace #13885686 | | found | | | | | | |
| miR-C5 | chr15 AC069082.9 | | trace #87318220 | | | | | | found | scaffold_3671 | |
| miR-C6 | chr22 AC005664.2 ident.precursor | | chr16 AC012526.32 | | | | | | | | |
| miR-C7 | chr1 AL512243.7 similar prec. | | trace #86694995 | | | | | | | | |

Fig.7 (cont.)

| | | | | | | | | |
|---|---|---|---|---|---|---|---|---|
| miR-C8 | | | | found, trace #51673384 | | | | |
| miR-C9 | | | | found, trace #78964803 | | | scaffold 2210, diff. precursor | |
| miR-C10 | chrX AF222686.1 nearly ident. precursor | | | found, trace #61928192 | | | | |
| miR-C11 | chr9 XM_098943.1 has C17U;prec.nearly identical to mouse | | | found,cDNA AI286629.1, has C17U | | | | |
| miR-C12 | | found | | found,trace#71 760450 | | | | |
| miR-C13 | | | | found,trace #88722637 | | | scaffold_2294 | |

Fig.7 (cont.)

| name | human | mouse | | | | | | | Drosophila | fugu fish | zebrafish |
|---|---|---|---|---|---|---|---|---|---|---|---|
| | | spleen | eye | kidney | testes | lung | thymus | skin | | | |
| miR-C14 | chr11 AC000159.6 | | | found, but no db hit | | | | | | | |
| miR-C15 | chr16 AC026468.6 nearly ident.precursor | | | EST BI687377.1, several trace | | | | | | scaffold_2083 | |
| miR-C16 | chr17 AC003101.1, similar precursor | | | found, trace#9555103 | | | | | | scaffold_246 | |
| miR-C17 | chr11 AC000159.6, chr1 AC103590.2; diff.prec. | | | found, trace #87796602 | | | | | | scaffold_152 | |
| miR-C18 | | | | found, trace #47823768 (close to miR-16) | | found | | found | | | |
| miR-C19 | chr17 AC009789.21 cloned from human cell line only | | | similar precursor in mouse chr11 AC011194.15 | | | | | | scaffold_18334 | |
| miR-C20 | chr1 AL355310.19 cloned from human cell line only | | | | | | | | | | |

| | | | | | | | | |
|---|---|---|---|---|---|---|---|---|
| miR-C21 | chr3 AC063952.15 cloned from human cell line only | | | | | | | |
| miR-C22 | chr19 AC007229.1; chr1 AL137157.7 similar precursor; cloned from human cell line only | | | | | scaffold_8399 | | |
| miR-C23 | | | trace #72257777 | found | | | | |
| miR-C24 | | | trace #69879879 | | | scaffold_2210 | | |
| miR-C25 | | | trace #49754566 | | | | | |
| miR-C26 | AL136001 ident. precursor | | trace #11977216 | | | | | |

Fig.7 (cont.)

Fig. 7 (cont.)

| name | human | mouse | | | | | | | Drosophila | fugu fish | zebrafish |
| --- | --- | --- | --- | --- | --- | --- | --- | --- | --- | --- | --- |
| | | spleen | eye | kidney | testes | lung | thymus | skin | | | |
| miR-C27 | chr9 AL159990.12 identical precursor | | trace #91503159 | | | | | | | scaffold_725 | |
| miR-C28 | XM_036612.4, precursor very similar | | | | | | | XM_149012.1 | | scaffold_13664 | |
| miR-C29 | chr14 AL136001.6 nearly identical precursor | | | | | | | trace #18453604 | | | |
| miR-C30 | chr6 AL391221.15 similar precursor | | | | | | | trace #84055510 | | | |
| miR-C31 | chr9 AC006312.8 | | | | | | | trace #89079710 | | scaffold_5830 | |
| miR-C32 | | | | | | | | U77364.1, intronic location Hoxd4 gene | | scaffold_82 | |
| miR-C33 | | | | | | | | trace #84780544 | | scaffold_15612 | |
| miR-C34 | | | | | | | trace# 72109322 | | | | |

MICRORNA MOLECULES

This Application is a divisional of U.S. Ser. No. 11/747,409 filed May 11, 2007, which is a divisional of U.S. Pat. No. 7,232,806 issued Jun. 19, 2007, which is a 371 of International Application PCT/EP2002/10881 filed Sep. 27, 2002, the disclosure of which is incorporated herein in its entirety by reference.

The present invention relates to novel small expressed (micro)RNA molecules associated with physiological regulatory mechanisms, particularly in developmental control.

In *Caenorhabditis elegans*, lin-4 and let-7 encode 22- and 21-nucleotide RNAs, respectively (1, 2), that function as key regulators of developmental timing (3-5). Because the appearance of these short RNAs is regulated during development, they are also referred to as "microRNAs" (miRNAs) or small temporal RNAs (stRNAs) (6). lin-4 and let-21 are the only known miRNAs to date.

Two distinct pathways exist in animals and plants in which 21- to 23-nucleotide RNAs function as post-transcriptional regulators of gene expression. Small interfering RNAs (siRNAs) act as mediators of sequence-specific mRNA degradation in RNA interference (RNAi) (7-11) whereas miRNAs regulate developmental timing by mediating sequence-specific repression of mRNA translation (3-5). siRNAs and miRNAs are excised from double-stranded RNA (dsRNA) precursors by Dicer (12, 13, 29), a multidomain RNase III protein, thus producing RNA species of similar size. However, siRNAs are believed to be double-stranded (8, 11, 12), while miRNAs are single-stranded (6).

We show that many more short, particularly 21- and 22-nt expressed RNAs, termed microRNAs (miRNAs), exist in invertebrates and vertebrates, and that some of these novel RNAs, similar to let-7 RNA (6), are also highly conserved. This suggests that sequence-specific post-transcriptional regulatory mechanisms mediated by small RNAs are more general than previously appreciated.

The present invention relates to an isolated nucleic acid molecule comprising:
  (a) a nucleotide sequence as shown in Table 1, Table 2, Table 3 or Table 4
  (b) a nucleotide sequence which is the complement of (a),
  (c) a nucleotide sequence which has an identity of at least 80%, preferably of at least 90% and more preferably of at least 99%, to a sequence of (a) or (b) and/or
  (d) a nucleotide sequence which hybridizes under stringent conditions to a sequence of (a), (b) and/or (c).

In a preferred embodiment the invention relates to miRNA molecules and analogs thereof, to miRNA precursor molecules and to DNA molecules encoding miRNA or miRNA precursor molecules.

Preferably the identity of sequence (c) to a sequence of (a) or (b) is at least 90%, more preferably at least 95%. The determination of identity (percent) may be carried out as follows:

$$I = n:L$$

wherein I is the identity in percent, n is the number of identical nucleotides between a given sequence and a comparative sequence as shown in Table 1, Table 2, Table 3 or Table 4 and L is the length of the comparative sequence. It should be noted that the nucleotides A, C, G and U as depicted in Tables 1, 2, 3 and 4 may denote ribonucleotides, deoxyribonucleotides and/or other nucleotide analogs, e.g. synthetic non-naturally occurring nucleotide analogs. Further nucleobases may be substituted by corresponding nucleobases capable of forming analogous H-bonds to a complementary nucleic acid sequence, e.g. U may be substituted by T.

Further, the invention encompasses nucleotide sequences which hybridize under stringent conditions with the nucleotide sequence as shown in Table 1, Table 2, Table 3 or Table 4, a complementary sequence thereof or a to highly identical sequence. Stringent hybridization conditions comprise washing for 1 h in 1×SSC and 0.1% SDS at 45° C., preferably at 48° C. and more preferably at 50° C., particularly for 1 h in 0.2×SSC and 0.1% SDS.

The isolated nucleic acid molecules of the invention preferably have a length of from 18 to 100 nucleotides, and more preferably from 18 to 80 nucleotides. It should be noted that mature miRNAs usually have a length of 19-24 nucleotides, particularly 21, 22 or 23 nucleotides. The miRNAs, however, may be also provided as a precursor which usually has a length of 50-90 nucleotides, particularly 60-80 nucleotides. It should be noted that the precursor may be produced by processing of a primary transcript which may have a length of >100 nucleotides.

The nucleic acid molecules may be present in single-stranded or double-stranded form. The miRNA as such is usually a single-stranded molecule, while the mi-precursor is usually an at least partially self-complementary molecule capable of forming double-stranded portions, e.g. stem- and loop-structures. DNA molecules encoding the miRNA and miRNA precursor molecules. The nucleic acids may be selected from RNA, DNA or nucleic acid analog molecules, such as sugar- or backbone-modified ribonucleotides or deoxyribonucleotides. It should be noted, however, that other nucleic analogs, such as peptide nucleic acids (PNA) or locked nucleic acids (LNA), are also suitable.

In an embodiment of the invention the nucleic acid molecule is an RNA- or DNA molecule, which contains at least one modified nucleotide analog, i.e. a naturally occurring ribonucleotide or deoxyribonucleotide is substituted by a non-naturally occurring nucleotide. The modified nucleotide analog may be located for example at the 5'-end and/or the 3'-end of the nucleic acid molecule.

Preferred nucleotide analogs are selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. In preferred sugar-modified ribonucleotides the 2'-OH-group is replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. In preferred backbone-modified ribonucleotides the phosphoester group connecting to adjacent ribonucleotides is replaced by a modified group, e.g. of phosphothioate group. It should be noted that the above modifications may be combined.

The nucleic acid molecules of the invention may be obtained by chemical synthesis methods or by recombinant methods, e.g. by enzymatic transcription from synthetic DNA-templates or from DNA-plasmids isolated from recombinant organisms. Typically phage RNA-polymerases are used for transcription, such as T7, T3 or SP6 RNA-polymerases.

The invention also relates to a recombinant expression vector comprising a recombinant nucleic acid operatively linked to an expression control sequence, wherein expression, i.e. transcription and optionally further processing results in a miRNA-molecule or miRNA precursor molecule as described above. The vector is preferably a DNA-vector, e.g. a viral vector or a plasmid, particularly an expression vector suitable for nucleic acid expression in eukaryotic, more particularly mammalian cells. The recombinant nucleic acid contained in said vector may be a sequence which results in the transcription of the miRNA-molecule as such, a precursor or a primary transcript thereof, which may be further processed to give the miRNA-molecule.

Further, the invention relates to diagnostic or therapeutic applications of the claimed nucleic acid molecules. For example, miRNAs may be detected in biological samples, e.g. in tissue sections, in order to determine and classify certain cell types or tissue types or miRNA-associated pathogenic disorders which are characterized by differential expression of miRNA-molecules or miRNA-molecule patterns. Further, the developmental stage of cells may be classified by determining temporarily expressed miRNA-molecules.

Further, the claimed nucleic acid molecules are suitable for therapeutic applications. For example, the nucleic acid molecules may be used as modulators or targets of developmental processes or disorders associated with developmental dysfunctions, such as cancer. For example, miR-15 and miR-16 probably function as tumor-suppressors and thus expression or delivery of these RNAs or analogs or precursors thereof to tumor cells may provide therapeutic efficacy, particularly against leukemias, such as B-cell chronic lymphocytic leukemia (B-CLL). Further, miR-10 is a possible regulator of the translation of Hox Genes, particularly Hox 3 and Hox 4 (or Scr and Dfd in *Drosophila*).

In general, the claimed nucleic acid molecules may be used as a modulator of the expression of genes which are at least partially complementary to said nucleic acid. Further, miRNA molecules may act as target for therapeutic screening procedures, e.g. inhibition or activation of miRNA molecules might modulate a cellular differentiation process, e.g. apoptosis.

Furthermore, existing miRNA molecules may be used as starting materials for the manufacture of sequence-modified miRNA molecules, in order to modify the target-specificity thereof, e.g. an oncogene, a multidrug-resistance gene or another therapeutic target gene. The novel engineered miRNA molecules preferably have an identity of at least 80% to the starting miRNA, e.g. as depicted in Tables 1, 2, 3 and 4. Further, miRNA molecules can be modified, in order that they are symetrically processed and then generated as double-stranded siRNAs which are again directed against therapeutically relevant targets.

Furthermore, miRNA molecules may be used for tissue reprogramming procedures, e.g. a differentiated cell line might be transformed by expression of miRNA molecules into a different cell type or a stem cell.

For diagnostic or therapeutic applications, the claimed RNA molecules are preferably provided as a pharmaceutical composition. This pharmaceutical composition comprises as an active agent at least one nucleic acid molecule as described above and optionally a pharmaceutically acceptable carrier.

The administration of the pharmaceutical composition may be carried out by known methods, wherein a nucleic acid is introduced into a desired target cell in vitro or in vivo. Commonly used gene transfer techniques include calcium phosphate, DEAE-dextran, electroporation and microinjection and viral methods [30, so 31, 32, 33, 34]. A recent addition to this arsenal of techniques for the introduction of DNA into cells is the use of cationic liposomes [35].

Commercially available cationic lipid formulations are e.g. Tfx 50 (Promega) or Lipofectamin 2000 (Life Technologies).

The composition may be in form of a solution, e.g. an injectable solution, a cream, ointment, tablet, suspension or the like. The composition may be administered in any suitable way, e.g. by injection, by oral, topical, nasal, rectal application etc. The carrier may be any suitable pharmaceutical carrier. Preferably, a carrier is used, which is capable of increasing the efficacy of the RNA molecules to enter the target-cells. Suitable examples of such carriers are liposomes, particularly cationic liposomes.

Further, the invention relates to a method of identifying novel microRNA-molecules and precursors thereof, in eukaryotes, particularly in vertebrates and more particularly in mammals, such as humans or mice. This method comprises: ligating 5'- and 3'-adapter-molecules to the end of a size-fractionated RNA-population, reverse transcribing said adapter-ligated RNA-population, and characterizing said reverse transcribed RNA-molecules, e.g. by amplification, concatamerization, cloning and sequencing.

A method as described above already has been described in (8), however, for the identification of siRNA molecules. Surprisingly, it was found now that the method is also suitable for identifying the miRNA molecules or precursors thereof as claimed in the present application.

Further, it should be noted that as 3'-adaptor for derivatization of the 3'-OH group not only 4-hydroxymethylbenzyl but other types of derivatization groups, such as alkyl, alkyl amino, ethylene glycol or 3'-deoxy groups are suitable.

Further, the invention shall be explained in more detail by the following Figures and Examples:

FIGURE LEGENDS

FIG. 1A. Expression of *D. melanogaster* miRNAs. Northern blots of total RNA isolated from staged populations of *D. melanogaster* were probed for the indicated miRNAs. The position of 76-nt val-tRNA is also indicated on the blots. 5S rRNA serves as loading control. E, embryo; L, larval stage; P, pupae; A, adult; S2, Schneider-2 cells. It should be pointed out, that S2 cells are polyclonal, derived from an unknown subset of embryonic tissues, and may have also lost some features of their tissue of origin while maintained in culture. miR-3 miR-6 RNAs were not detectable in S2 cells (data not shown). miR-14 was not detected by Northern blotting and may be very weakly expressed, which is consistent with its cloning frequency. Similar miRNA sequences are difficult to distinguish by Northern blotting because of potential cross-hybridization of probes.

Figure 1B:
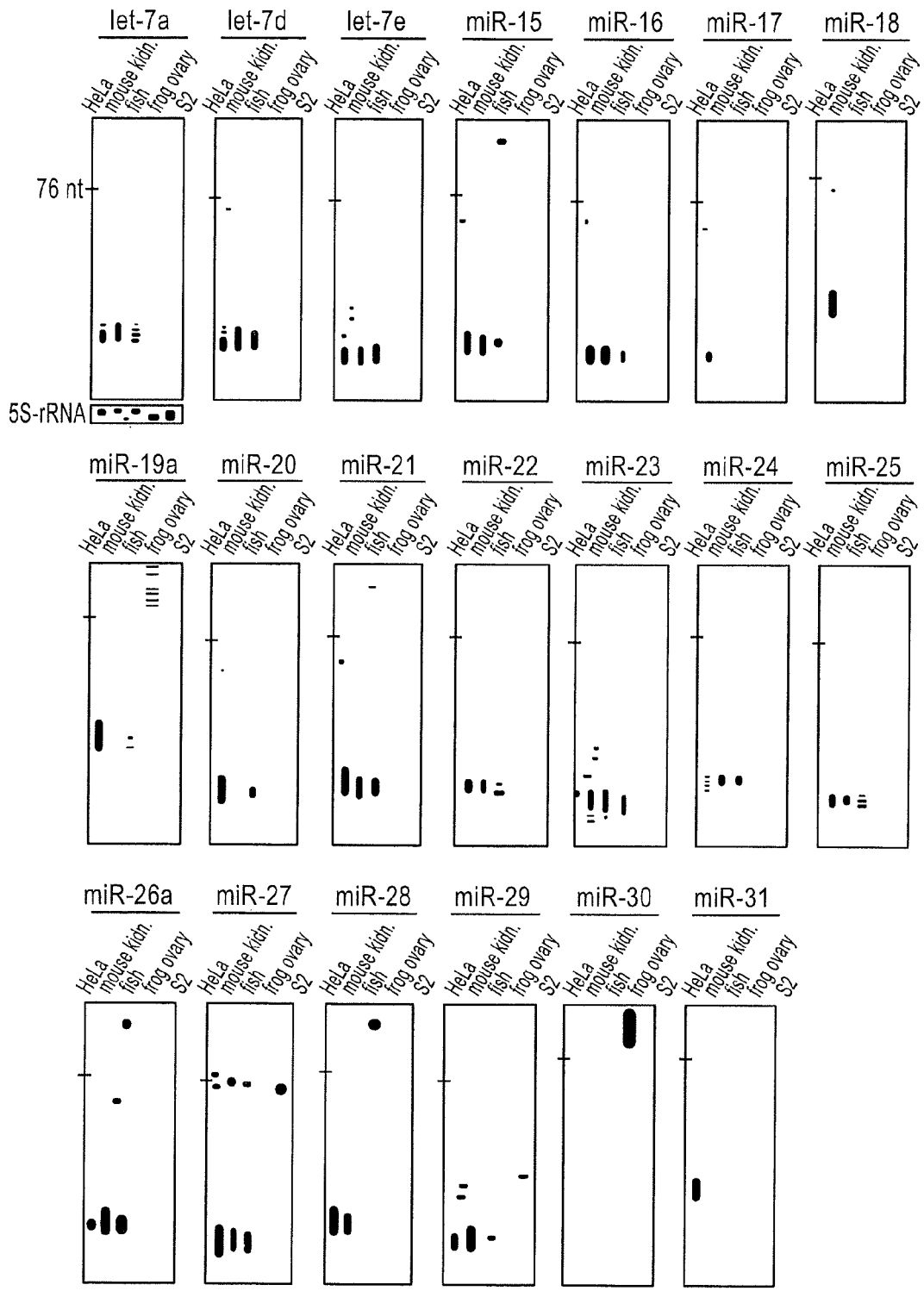

FIG. 1B. Expression of vertebrate miRNAs. Northern blots of total RNA isolated from HeLa cells, mouse kidneys, adult zebrafish, frog ovaries, and S2 cells were probed for the indicated miRNAs. The position of 76-nt val-tRNA is also indicated on the blots. 5S rRNA from the preparations of total RNA from the indicated species is also shown. The gels used for probing of miR-18, miR-19a, miR-30, and miR-31 were not run as far as the other gels (see tRNA marker position). miR-32 and miR-33 were not detected by Northern blotting, which is consistent with their low cloning frequency. Oligodeoxynucleotides used as Northern probes were:

```
let-7a,
5' TACTATACAACCTACTACCTCAATTTGCC;   (SEQ ID NO: 1)

let-7d,
5' ACTATGCAACCTACTACCTCT;           (SEQ ID NO: 2)
```

```
let-7e,
5' ACTATACAACCTCCTACCTCA;                (SEQ ID NO: 3)

D. melanogaster val-tRNA,
5' TGGTGTTTCCGCCCGGGAA;                  (SEQ ID NO: 4)

miR-1,
5' TGGAATGTAAAGAAGTATGGAG;               (SEQ ID NO: 5)

miR-2b,
5' GCTCCTCAAAGCTGGCTGTGATA;              (SEQ ID NO: 6)

miR-3,
5' TGAGACACACTTTGCCCAGTGA;               (SEQ ID NO: 7)

miR-4,
5' TCAATGGTTGTCTAGCTTTAT;                (SEQ ID NO: 8)

miR-5,
5' CATATCACAACGATCGTTCCTTT;              (SEQ ID NO: 9)

miR-6,
5' AAAAAGAACAGCCACTGTGATA;               (SEQ ID NO: 10)

miR-7,
5' TGGAAGACTAGTGATTTTGTTGT;              (SEQ ID NO: 11)

miR-8,
5' GACATCTTTACCTGACAGTATTA;              (SEQ ID NO: 12)

miR-9,
5' TCATACAGCTAGATAACCAAAGA;              (SEQ ID NO: 13)

miR-10,
5' ACAAATTCGGATCTACAGGGT;                (SEQ ID NO: 14)

miR-11,
5' GCAAGAACTCAGACTGTGATG;                (SEQ ID NO: 15)

miR-12,
5' ACCAGTACCTGATGTAATACTCA;              (SEQ ID NO: 16)

miR-13a,
5' ACTCGTCAAAATGGCTGTGATA;               (SEQ ID NO: 17)

miR-14,
5' TAGGAGAGAGAAAAAGACTGA;                (SEQ ID NO: 18)

miR-15,
5' TAGCAGCACATAATGGTTTGT;                (SEQ ID NO: 19)

miR-16,
5' GCCAATATTTACGTGCTGCTA;                (SEQ ID NO: 20)

miR-17,
5' TACAAGTGCCTTCACTGCAGTA;               (SEQ ID NO: 21)

miR-18,
5' TATCTGCACTAGATGCACCTTA;               (SEQ ID NO: 22)

miR-19a,
5' TCAGTTTTGCATAGATTTGCACA;              (SEQ ID NO: 23)

miR-20,
5' TACCTGCACTATAAGCACTTTA;               (SEQ ID NO: 24)

miR-21,
5' TCAACATCAGTCTGATAAGCTA;               (SEQ ID NO: 25)

miR-22,
5' ACAGTTCTTCAACTGGCAGCTT;               (SEQ ID NO: 26)

miR-23,
5' GGAAATCCCTGGCAATGTGAT;                (SEQ ID NO: 27)

miR-24,
5' CTGTTCCTGCTGAACTGAGCCA;               (SEQ ID NO: 28)

miR-25,
5' TCAGACCGAGACAAGTGCAATG;               (SEQ ID NO: 29)

miR-26a,
5' AGCCTATCCTGGATTACTTGAA;               (SEQ ID NO: 30)

miR-27;
5' AGCGGAACTTAGCCACTGTGAA;               (SEQ ID NO: 31)

miR-28,
5' CTCAATAGACTGTGAGCTCCTT;               (SEQ ID NO: 32)

miR-29,
5' AACCGATTTCAGATGGTGCTAG;               (SEQ ID NO: 33)

miR-30,
5' GCTGCAAACATCCGACTGAAAG;               (SEQ ID NO: 34)

miR-31,
5' CAGCTATGCCAGCATCTTGCCT;               (SEQ ID NO: 35)

miR-32,
5' GCAACTTAGTAATGTGCAATA;                (SEQ ID NO: 36)

miR-33,
5' TGCAATGCAACTACAATGCACC.               (SEQ ID NO: 37)
```

Figure 2:
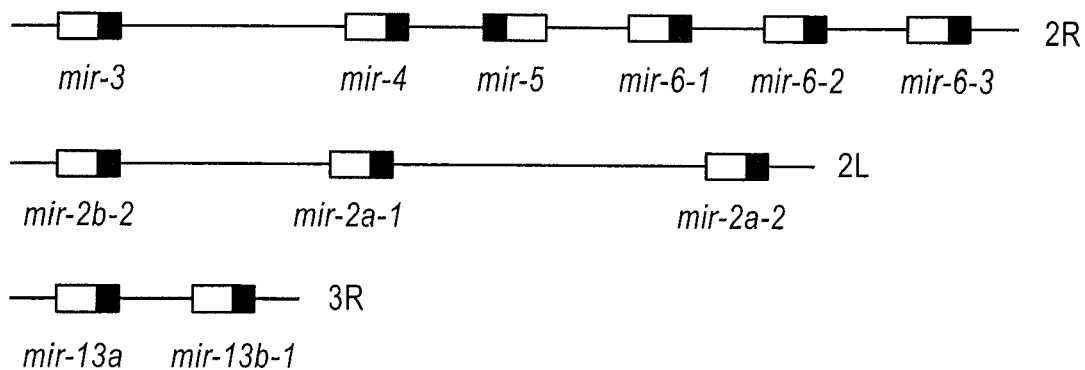
Figure 2:
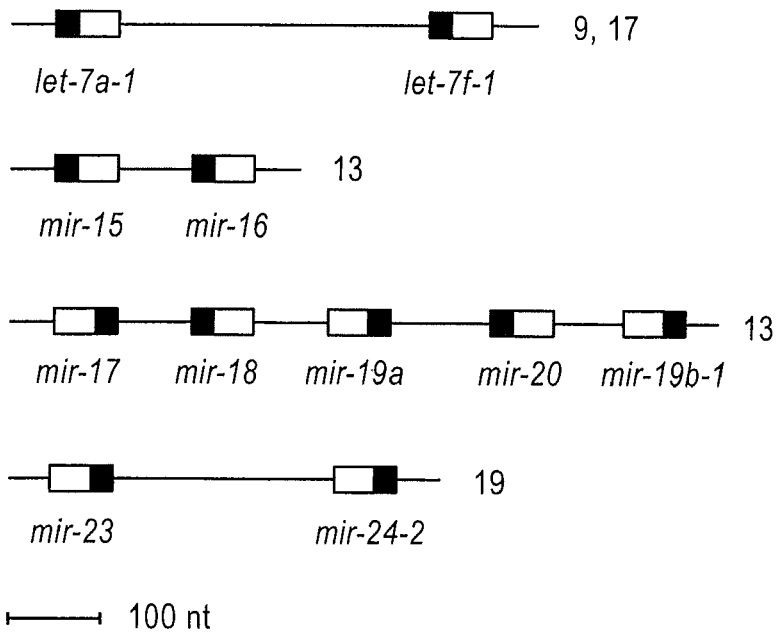

FIG. 2. Genomic organization of miRNA gene clusters. The precursor structure is indicated as box and the location of the miRNA within the precursor is shown in gray; the chromosomal location is also indicated to the right. (A) *D. melanogaster* miRNA gene clusters. (B) Human miRNA gene clusters. The cluster of let-7a-1 and let-7f-1 is separated by 26500 nt from a copy of let-7d on chromosome 9 and 17. A cluster of let-7a-3 and let-7b, separated by 938 nt on chromosome 22, is not illustrated.

Figure 3:
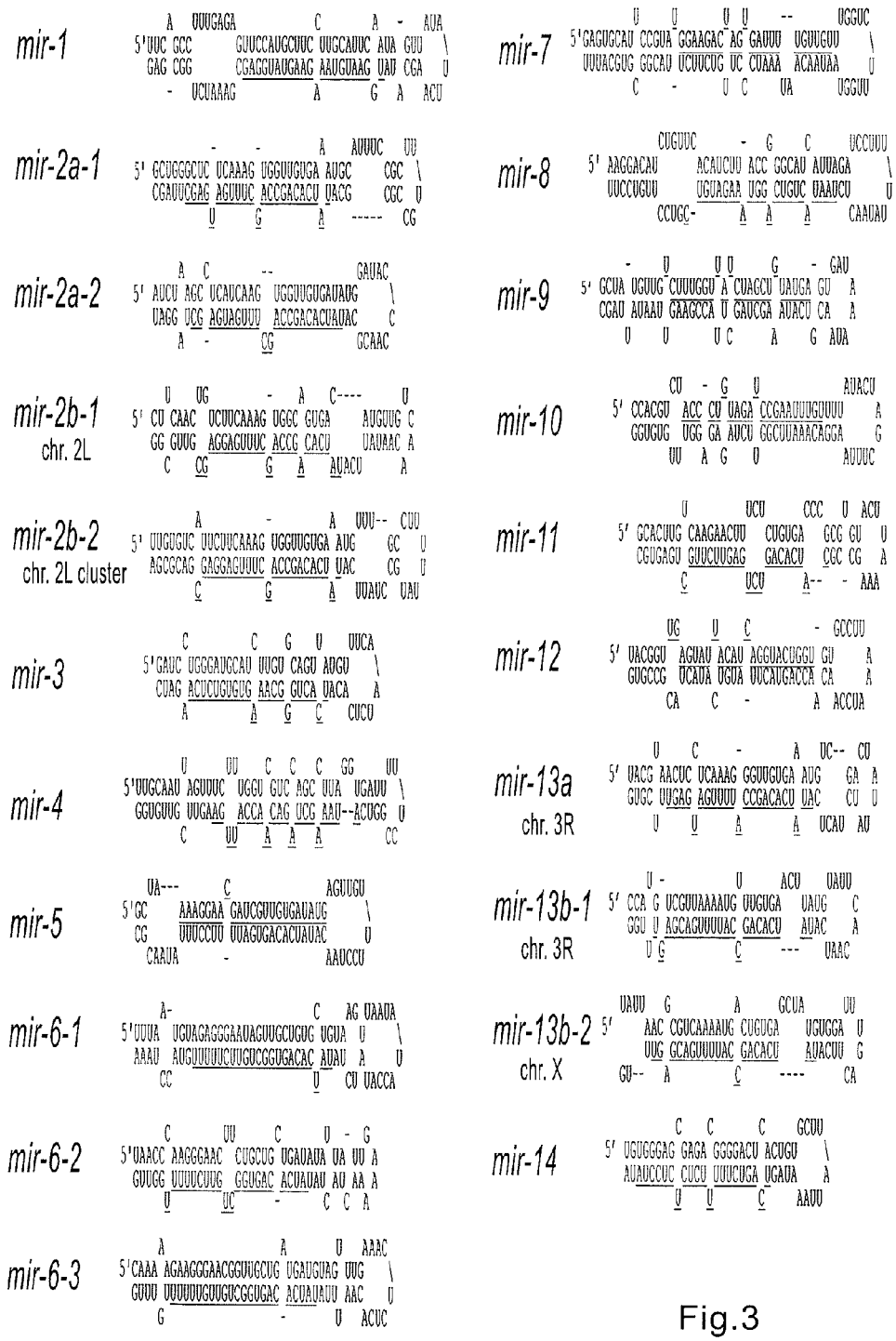

FIG. 3. Predicted precursor structures of *D. melanogaster* miRNAs. RNA Secondary structure prediction was performed using mfold version 3.1 [28] and manually refined to accommodate G/U wobble base pairs in the helical segments. The miRNA sequence is underlined. The actual size of the stem-loop structure is not known experimentally and may be slightly shorter or longer than represented. Multicopy miRNAs and their corresponding precursor structures are also shown.

Figure 4:
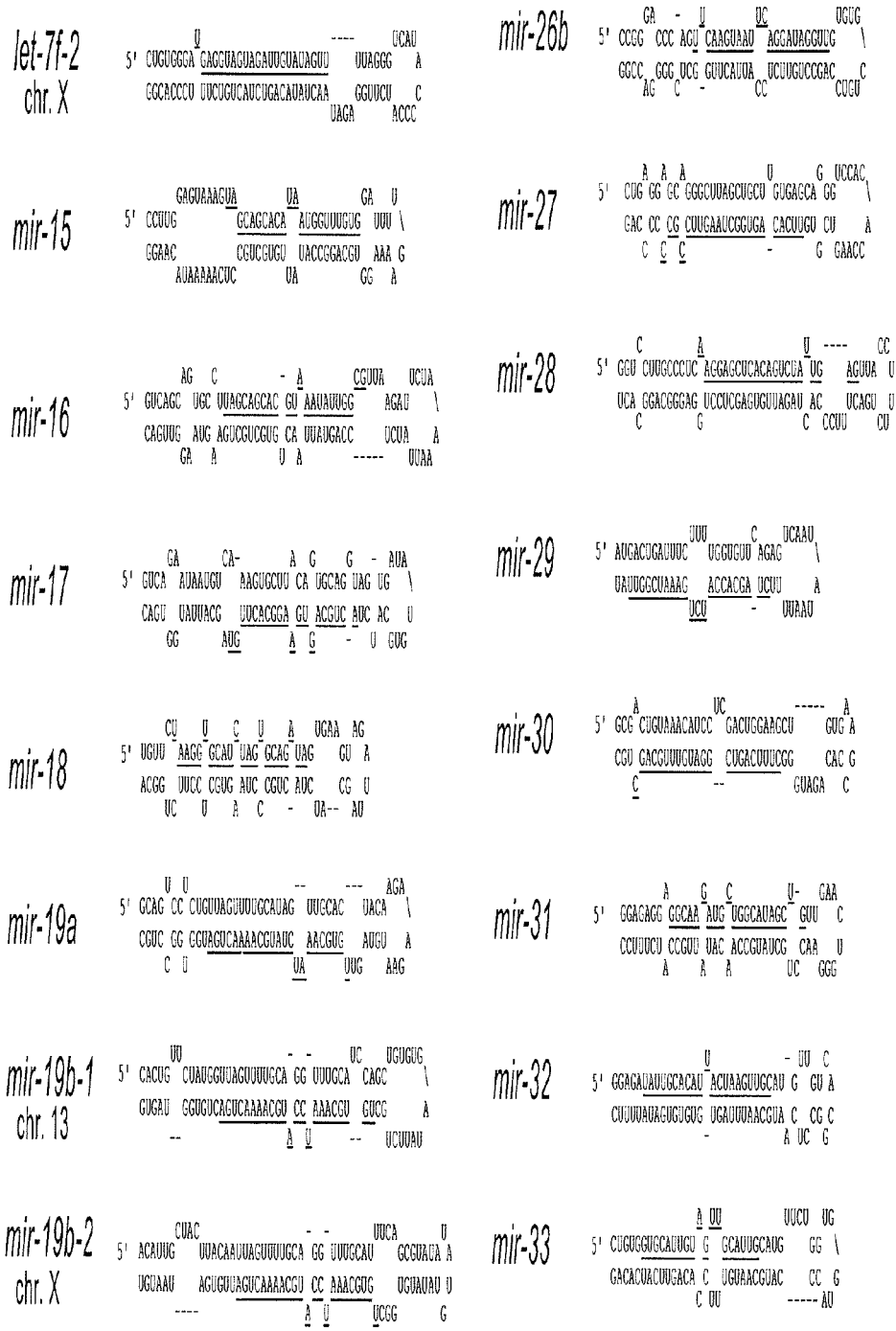

FIG. 4. Predicted precursor structures of human miRNAs. For legend, see FIG. 3.

Figure 5:
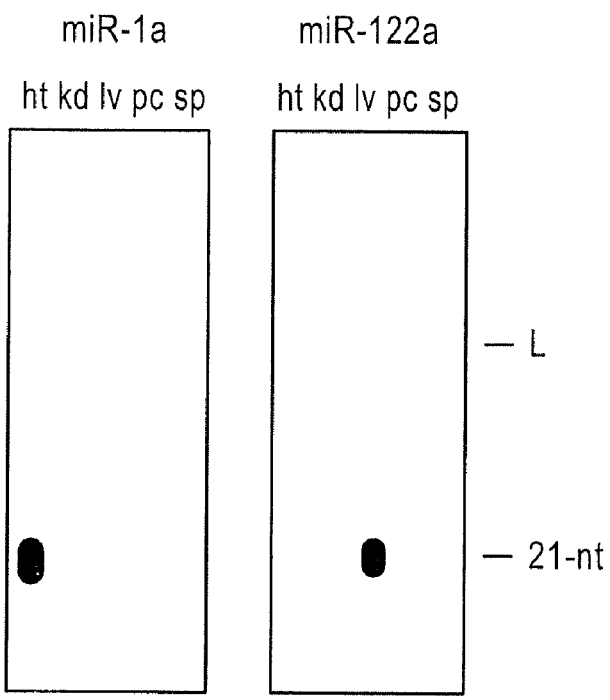
Figure 5:
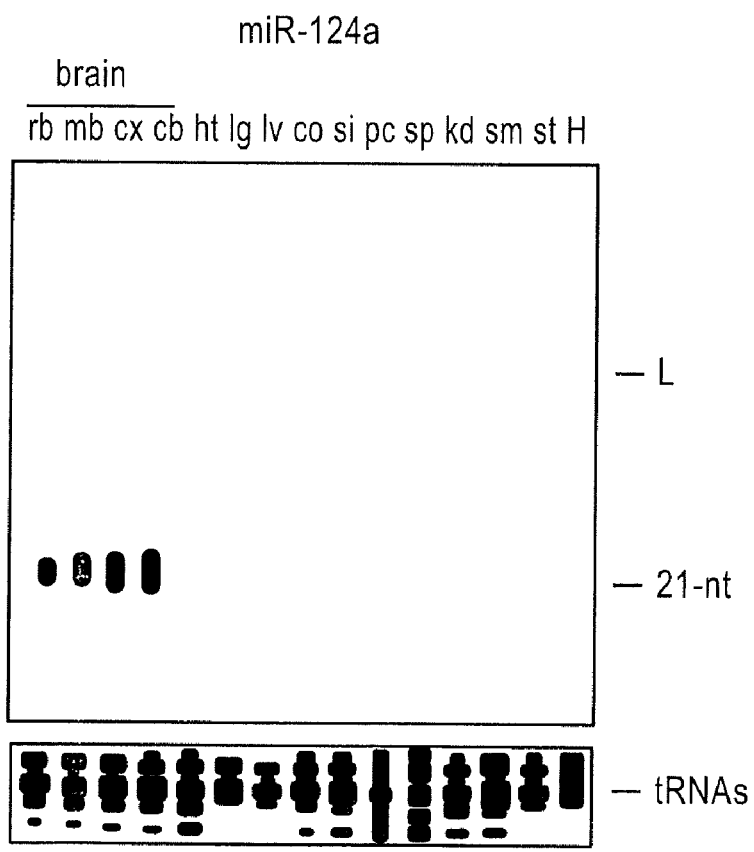
Figure 5:
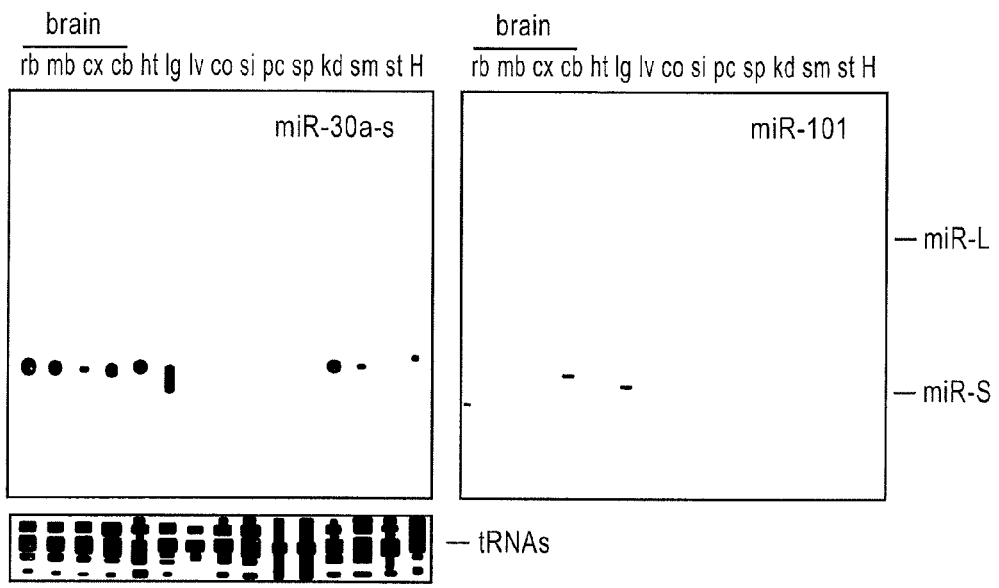
Figure 5:
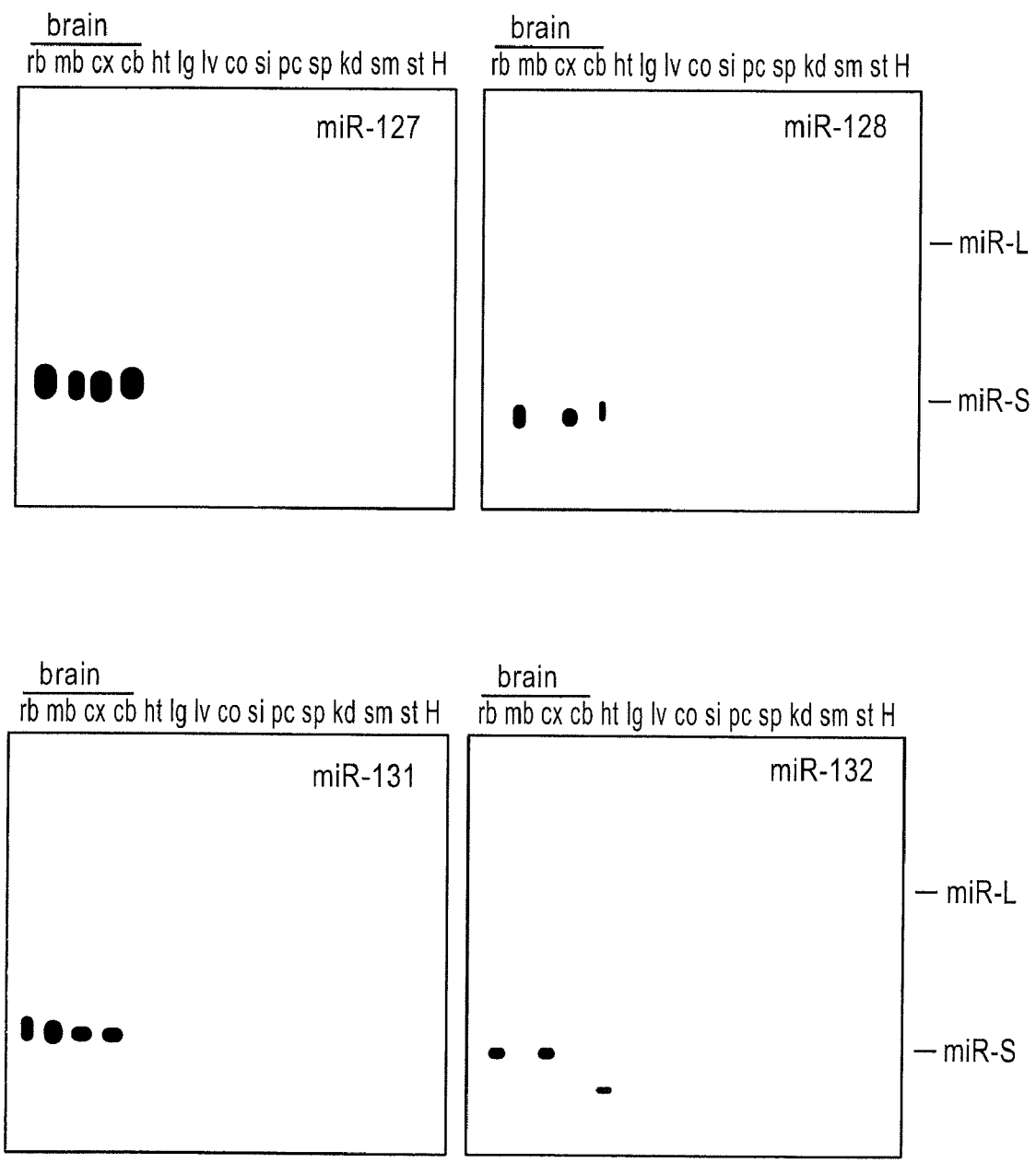
Figure 5:
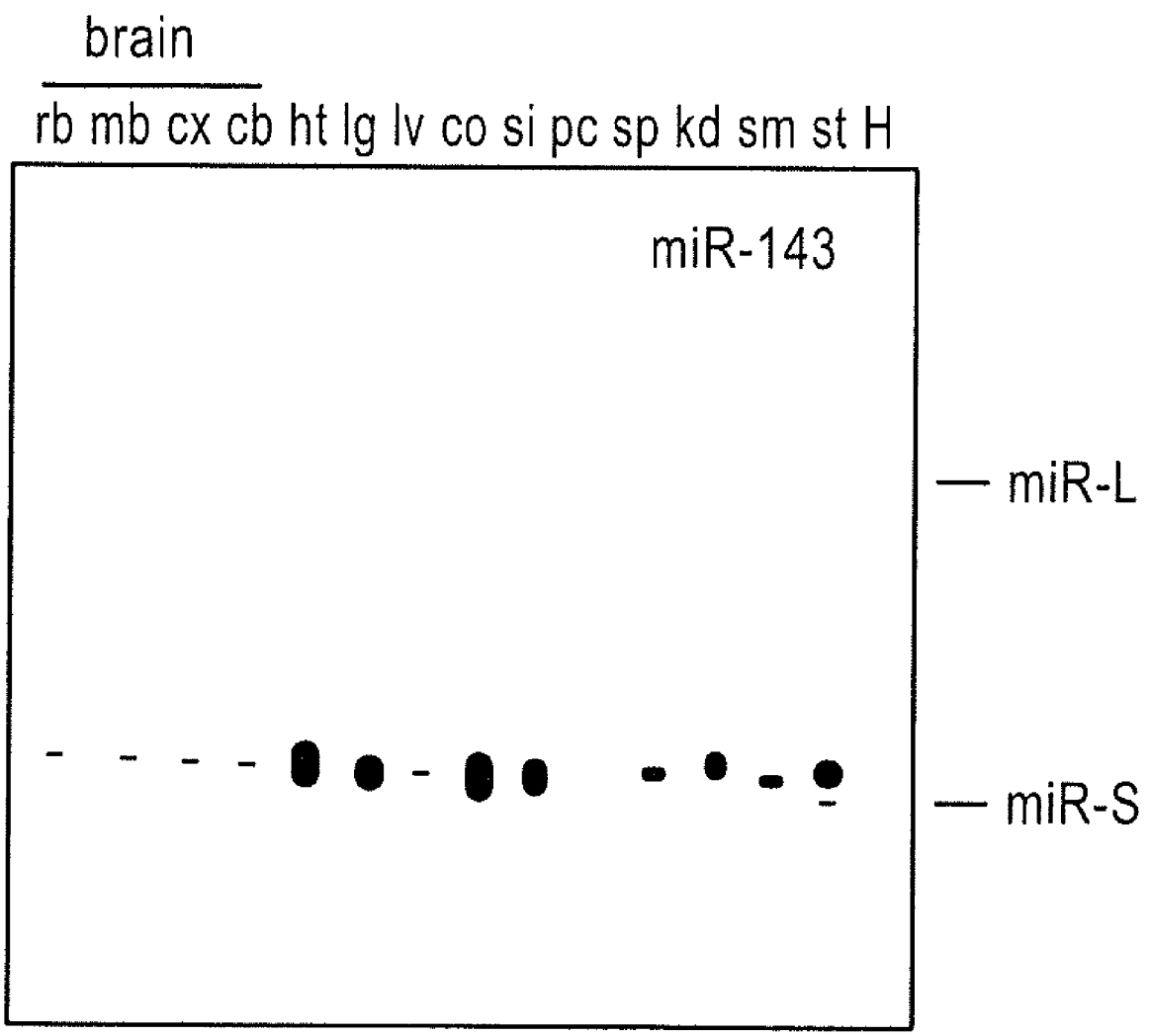

FIG. 5. Expression of novel mouse miRNAs. Northern blot analysis of novel mouse miRNAs. Total RNA from different mouse tissues was blotted and probed with a 5'-radiolabeled oligodeoxynucleotide complementary to the indicated miRNA. Equal loading of total RNA on the gel was verified by ethidium bromide staining prior to transfer; the band representing tRNAs is shown. The fold-back precursors are indicated with capital L. Mouse brains were dissected into midbrain, mb, cortex, cx, cerebellum, cb. The rest of the brain, rb, was also used. Other tissues were heart, ht, lung, lg, liver, lv, colon, co, small intestine, si, pancreas, pc, spleen, sp, kidney, kd, skeletal muscle, sm, stomach, st, H, human Hela SS3 cells. Oligodeoxynucleotides used as Northern probes were:

```
miR-1a,
CTCCATACTTCTTTACATTCCA;                  (SEQ ID NO: 38)

miR-30b,
GCTGAGTGTAGGATGTTTACA;                   (SEQ ID NO: 39)

miR-30a-s,
GCTTCCAGTCGAGGATGTTTACA;                 (SEQ ID NO: 40)
```

-continued

```
miR-99b,
CGCAAGGTCGGTTCTACGGGTG;      (SEQ ID NO: 41)

miR-101,
TCAGTTATCACAGTACTGTA;        (SEQ ID NO: 42)

miR-122a,
ACAAACACCATTGTCACACTCCA;     (SEQ ID NO: 43)

miR-124a,
TGGCATTCACCGCGTGCCTTA;       (SEQ ID NO: 44)

miR-125a,
CACAGGTTAAAGGGTCTCAGGGA;     (SEQ ID NO: 45)

miR-125b,
TCACAAGTTAGGGTCTCAGGGA;      (SEQ ID NO: 46)

miR-127,
AGCCAAGCTCAGACGGATCCGA;      (SEQ ID NO: 47)

miR-128,
AAAAGAGACCGGTTCACTCTGA;      (SEQ ID NO: 48)

miR-129,
GCAAGCCCAGACCGAAAAAAG;       (SEQ ID NO: 49)

miR-130,
GCCCTTTTAACATTGCACTC;        (SEQ ID NO: 50)

miR-131,
ACTTTCGGTTATCTAGCTTTA;       (SEQ ID NO: 51)

miR-132,
ACGACCATGGCTGTAGACTGTTA;     (SEQ ID NO: 52)

miR-143,
TGAGCTACAGTGCTTCATCTCA.      (SEQ ID NO: 53)
```

Figure 6:
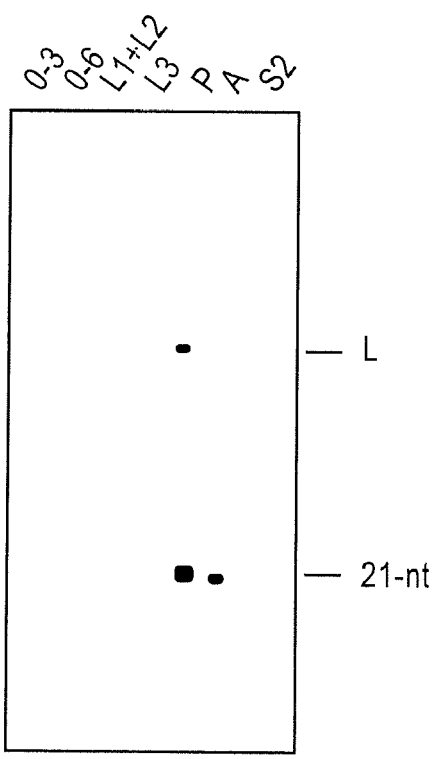

FIG. 6. Potential orthologs of lin-4 stRNA. (A) Sequence alignment of C. elegans lin-4 stRNA with mouse miR-125a and miR-125b and the D. melanogaster miR-125. Differences are highlighted by gray boxes. (B) Northern blot of total RNA isolated from staged populations of D. melanogaster, probed for miR-125. E, embryo; L, larval stage; P, pupae; A, adult; S2, Schneider-2 cells.

FIG. 7. Predicted precursor structures of miRNAs, sequence accession numbers and homology information. RNA secondary structure prediction was performed using mfold version 3.1 and manually refined to accommodate G/U wobble base pairs in the helical segments. Dashes were inserted into the secondary structure presentation when asymmetrically bulged nucleotides had to be accommodated. The excised miRNA sequence is underlined. The actual size of the stem-loop structure is not known experimentally and may be slightly shorter or longer than represented. Multicopy miRNAs and their corresponding precursor structures are also shown. In cases where no mouse precursors were yet deposited in the database, the human orthologs are indicated. miRNAs which correspond to D. melanogaster or human sequences are included. Published C. elegans miRNAs [36, 37] are also included in the table. A recent set of new HeLa cell miRNAs is also indicated [46]. If several ESTs were retrieved for one organism in the database, only those with different precursor sequences are listed. miRNA homologs found in other species are indicated. Chromosomal location and sequence accession numbers, and clusters of miRNA genes are indicated. Sequences from cloned miRNAs were searched against mouse and human in GenBank (including trace data), and against Fugu rubripes and Danio rerio at www.jgi.doe.gov and www.sanger.ac.uk, respectively.

EXAMPLE 1

MicroRNAs from D. melanogaster and Human

We previously developed a directional cloning procedure to isolate siRNAs after processing of long dsRNAs in Drosophila melanogaster embryo lysate (8). Briefly, 5' and 3' adapter molecules were ligated to the ends of a size-fractionated RNA population, followed by reverse transcription, PCR amplification, concatamerization, cloning and sequencing. This method, originally intended to isolate siRNAs, led to the simultaneous identification of 14 novel 20- to 23-nt short RNAs which are encoded in the D. melanogaster genome and which are expressed in 0 to 2 h embryos (Table 1). The method was adapted to clone RNAs in a similar size range from HeLa cell total RNA (14), which led to the identification of 19 novel human stRNAs (Table 2), thus providing further evidence for the existence of a large class of small RNAs with potential regulatory roles. According to their small size, we refer to these novel RNAs as microRNAs or miRNAs. The miRNAs are abbreviated as miR-1 to miR-33, and the genes encoding miRNAs are named mir-1 to mir-33. Highly homologous miRNAs are classified by adding a lowercase letter, followed by a dash and a number for designating multiple genomic copies of a mir gene.

The expression and size of the cloned, endogenous short RNAs was also examined by Northern blotting (FIG. 1, Table 1 and 2). Total RNA isolation was performed by acid guanidinium thiocyanate-phenol-chloroform extraction [45]. Northern analysis was performed as described [1], except that the total RNA was resolved on a 15% denaturing polyacrylamide gel, transferred onto Hybond-N+membrane (Amersham Pharmacia Biotech), and the hybridization and wash steps were performed at 50° C. Oligodeoxynucleotides used as Northern probes were 5'-32P-phosphorylated, complementary to the miRNA sequence and 20 to 25 nt in length.

5S rRNA was detected by ethidium staining of polyacrylamide gels prior to transfer. Blots were stripped by boiling in 0.1% aqueous sodium dodecylsulfate/0.1×SSC (15 mM sodium chloride, 1.5 mM sodium citrate, pH 7.0) for 10 min, and were re-probed up to 4 times until the 21-nt signals became too weak for detection. Finally, blots were probed for val-tRNA as size marker.

For analysis of D. melanogaster RNAs, total RNA was prepared from different developmental stages, as well as cultured Schneider-2 (S2) cells, which originally derive from 20-24 h D. melanogaster embryos [15] (FIG. 1, Table 1). miR-3 to miR-7 are expressed only during embryogenesis and not at later developmental stages. The temporal expression of miR-1, miR-2 and miR-8 to miR-13 was less restricted. These miRNAs were observed at all developmental stages though significant variations in the expression levels were sometimes observed. Interestingly, miR-1, miR-3 to miR-6, and miR-8 to miR-11 were completely absent from cultured Schneider-2 (S2) cells, which were originally derived from 20-24 h D. melanogaster embryos [15], while miR-2, miR-7, miR-12, and miR-13 were present in S2 cells, therefore indicating cell type-specific miRNA expression. miR-1, miR-8, and miR-12 expression patterns are similar to those of lin-4 stRNA in C. elegans, as their expression is strongly upregulated in larvae and sustained to adulthood [16]. miR-9 and miR-11 are present at all stages but are strongly reduced in the adult which may reflect a maternal contribution from germ cells or expression in one sex only.

The mir-3 to mir-6 genes are clustered (FIG. 2A), and mir-6 is present as triple repeat with slight variations in the mir-6 precursor sequence but not in the miRNA sequence itself. The expression profiles of miR-3 to miR-6 are highly similar (Table 1), which suggests that a single embryo-specific precursor transcript may give rise to the different miRNAs, or that the same enhancer regulates miRNA-specific promoters. Several other fly miRNAs are also found in gene clusters (FIG. 2A).

The expression of HeLa cell miR-15 to miR-33 was examined by Northern blotting using HeLa cell total RNA, in addition to total RNA prepared from mouse kidneys, adult zebrafish, *Xenopus laevis* ovary, and *D. melanogaster* S2 cells. (FIG. 1B, Table 2). miR-15 and miR-16 are encoded in a gene cluster (FIG. 2B) and are detected in mouse kidney, fish, and very weakly in frog ovary, which may result from miRNA expression in somatic ovary tissue rather than oocytes. mir-17 to mir-20 are also clustered (FIG. 2B), and are expressed in HeLa cells and fish, but undetectable in mouse kidney and frog ovary (FIG. 1, Table 2), and therefore represent a likely case of tissue-specific miRNA expression.

The majority of vertebrate and invertebrate miRNAs identified in this study are not related by sequence, but a few exceptions, similar to the highly conserved let-7 RNA [6], do exist. Sequence analysis of the *D. melanogaster* miRNAs revealed four such examples of sequence conservation between invertebrates and vertebrates. miR-1 homologs are encoded in the genomes of *C. elegans, C. briggsae*, and humans, and are found in cDNAs from zebrafish, mouse, cow and human. The expression of mir-1 was detected by Northern blotting in total RNA from adult zebrafish and *C. elegans*, but not in total RNA from HeLa cells or mouse kidney (Table 2 and data not shown). Interestingly, while mir-1 and let-7 are expressed both in adult flies (FIG. 1A) [6] and are both undetected in S2 cells, miR-1 is, in contrast to let-7, undetectable in HeLa cells. This represents another case of tissue-specific expression of a miRNA, and indicates that miRNAs may not only play a regulatory role in developmental timing, but also in tissue specification. miR-7 homologs were found by database searches in mouse and human genomic and expressed sequence tag sequences (ESTs). Two mammalian miR-7 variants are predicted by sequence analysis in mouse and human, and were detected by Northern blotting in HeLa cells and fish, but not in mouse kidney (Table 2). Similarly, we identified mouse and human miR-9 and miR-1.0 homologs by database searches but only detected mir-10 expression in mouse kidney.

The identification of evolutionary related miRNAs, which have already acquired multiple sequence mutations, was not possible by standard bioinformatic searches. Direct comparison of the *D. melanogaster* miRNAs with the human miRNAs identified an 11-nt segment shared between *D. melanogaster* miR-6 and HeLa miR-27, but no further relationships were detected. One may speculate that most miRNAs only act on a single target and therefore allow for rapid evolution by covariation, and that highly conserved miRNAs act on more than one target sequence, and therefore have a reduced probability for evolutionary drift by covariation [6]. An alternative interpretation is that the sets of miRNAs from *D. melanogaster* and humans are fairly incomplete and that many more miRNAs remain to be discovered, which will provide the missing evolutionary links.

lin-4 and let-7 stRNAs were predicted to be excised from longer transcripts that contain approximately 30 base-pair stem-loop structures [1, 6]. Database searches for newly identified miRNAs revealed that all miRNAs are flanked by sequences that have the potential to form stable stem-loop structures (FIGS. 3 and 4). In many cases, we were able to detect the predicted, approximately 70-nt precursors by Northern blotting (FIG. 1).

Some miRNA precursor sequences were also identified in mammalian cDNA (EST) databases [27], indicating that primary transcripts longer than 70-nt stem-loop precursors do also exist. We never cloned a 22-nt RNA complementary to any of the newly identified miRNAs, and it is as yet unknown how the cellular processing machinery distinguishes between the miRNA and its complementary strand. Comparative analysis of the precursor stem-loop structures indicates that the loops adjacent to the base-paired miRNA segment can be located on either side of the miRNA sequence (FIGS. 3 and 4), suggesting that the 5' or 3' location of the stem-closing loop is not the determinant of miRNA excision. It is also unlikely that the structure, length or stability of the precursor stem is the critical determinant as the base-paired structures are frequently imperfect and interspersed by less stable, non-Watson-Crick base pairs such as G/A, U/U, C/U, A/A, and G/U wobbles. Therefore, a sequence-specific recognition process is a likely determinant for miRNA excision, perhaps mediated by members of the Argonaute (rde-1/ago1/piwi) protein family. Two members of this family, alg-1 and alg-2, have recently been shown to be critical for stRNA processing in *C. elegans* [13]. Members of the Argonaute protein family are also involved in RNAi and PTGS. In *D. melanogaster*, these include argonaute2, a component of the siRNA-endonuclease complex (RISC) [17], and its relative aubergine, which is important for silencing of repeat genes [18]. In other species, these include rde-1, argonaute1, and qde-2, in *C. elegans* [19], *Arabidopsis thaliana* [20], and *Neurospora crassa* [21], respectively. The Argonaute protein family therefore represents, besides the RNase III Dicer [12, 13], another evolutionary link between RNAi and miRNA maturation.

Despite advanced genome projects, computer-assisted detection of genes encoding functional RNAs remains problematic [22]. Cloning of expressed, short functional RNAs, similar to EST approaches (RNomics), is a powerful alternative and probably the most efficient method for identification of such novel gene products [23-26]. The number of functional RNAs has been widely underestimated and is expected to grow rapidly because of the development of new functional RNA cloning methodologies.

The challenge for the future is to define the function and the potential targets of these novel miRNAs by using bioinformatics as well as genetics, and to establish a complete catalogue of time- and tissue-specific distribution of the already identified and yet to be uncovered miRNAs. lin-4 and let-7 stRNAs negatively regulate the expression of proteins encoded by mRNAs whose 3' untranslated regions contain sites of complementarity to the stRNA [3-5].

Thus, a series of 33 novel genes, coding for 19- to 23-nucleotide microRNAs (miRNAs), has been cloned from fly embryos and human cells. Some of these miRNAs are highly conserved between vertebrates and invertebrates and are developmentally or tissue-specifically expressed. Two of the characterized human miRNAs may function as tumor suppressors in B-cell chronic lymphocytic leukemia. miRNAs are related to a small class of previously described 21- and 22-nt RNAs (lin-4 and let-7 RNAs), so-called small temporal RNAs (stRNAs), and regulate developmental timing in *C. elegans* and other species. Similar to stRNAs, miRNAs are presumed to regulate translation of specific target mRNAs by binding to partially complementary sites, which are present in their 3'-untranslated regions.

Deregulation of miRNA expression may be a cause of human disease, and detection of expression of miRNAs may become useful as a diagnostic. Regulated expression of miR-NAs in cells or tissue devoid of particular miRNAs may be useful for tissue engineering, and delivery or transgenic expression of miRNAs may be useful for therapeutic intervention. miRNAs may also represent valuable drug targets itself. Finally, miRNAs and their precursor sequences may be engineered to recognize therapeutic valuable targets.

EXAMPLE 2 miRNAs from Mouse

To gain more detailed insights into the distribution and function of miRNAs in mammals, we investigated the tissue-specific distribution of miRNAs in adult mouse. Cloning of miRNAs from specific tissues was preferred over whole organism-based cloning because low-abundance miRNAs that normally go undetected by Northern blot analysis are identified clonally. Also, in situ hybridization techniques for detecting 21-nt RNAs have not yet been developed. Therefore, 19- to 25-nucleotide RNAs were cloned and sequenced from total RNA, which was isolated from 18.5 weeks old BL6 mice. Cloning of miRNAs was performed as follows: 0.2 to 1 mg, of total RNA was separated on a 15% denaturing polyacrylamide gel and RNA of 19- to 25-nt size was recovered. A 5'-phosphorylated 3'-adapter oligonucleotide (5'-pUUUaac-cgcgaattccagx: uppercase, RNA; lowercase, DNA; p, phosphate; x, 3'-Amino-Modifier C-7, ChemGenes, Ashland, Mass., USA, Cat. No. NSS-1004; SEQ ID NO:54) and a 5'-adapter oligonucleotide (5'-acggaattcctcactAAA: uppercase, RNA; lowercase, DNA; SEQ ID NO:55) were ligated to the short RNAs. RT/PCR was performed with 3'-primer (5'-GACTAGCTGGAATTCGCGGTTAAA; SEQ ID NO:56) and 5'-primer (5'-CAGCCAACGGAATTCCTCACTAAA; SEQ ID NO:57). In order to introduce Ban I restriction sites, a second PCR was performed using the primer pair 5'-CAGC-CAACAGGCACCGAATTCCTCACTAAA (SEQ ID NO:57) and 5'-GACTAGCTTGGTGCCGAATTCGCGGT-TAAA (SEQ ID NO:56), followed by concatamerization after Ban I digestion and T4 DNA ligation. Concatamers of 400 to 600 basepairs were cut out from 1.5% agarose gels and recovered by Biotrap (Schleicher & Schuell) electroelution (1×TAE buffer) and by ethanol precipitation. Subsequently, the 3' ends of the concatamers were filled in by incubating for 15 min at 72° C. with Taq polymerase in standard PCR reaction mixture. This solution was diluted 3-fold with water and directly used for ligation into pCR2.1 TOPO vectors. Clones were screened for inserts by PCR and 30 to 50 samples were subjected to sequencing. Because RNA was prepared from combining tissues of several mice, minor sequence variations that were detected multiple times in multiple clones may reflect polymorphisms rather than RT/PCR mutations. Public database searching was used to identify the genomic sequences encoding the approx. 21-nt RNAs. The occurrence of a 20 to 30 basepair fold-back structure involving the immediate upstream or downstream flanking sequences was used to assign miRNAs [36-38].

We examined 9 different mouse tissues and identified 34 novel miRNAs, some of which are highly tissue-specifically expressed (Table 3 and FIG. 5). Furthermore, we identified 33 new miRNAs from different mouse tissues and also from human Soas-2 osteosarcoma cells (Table 4). miR-1 was previously shown by Northern analysis to be strongly expressed in adult heart, but not in brain, liver, kidney, lung or colon [37]. Here we show that miR-1 accounts for 45% of all mouse miRNAs found in heart, yet miR-1 was still expressed at a low level in liver and midbrain even though it remained undetectable by Northern analysis. Three copies or polymorphic alleles of miR-1 were found in mice. The conservation of tissue-specific miR-1 expression between mouse and human provides additional evidence for a conserved regulatory role of this miRNA. In liver, variants of miR-122 account for 72% of all cloned miRNAs and miR-122 was undetected in all other tissues analyzed. In spleen, miR-143 appeared to be most abundant, at a frequency of approx. 30%. In colon, miR-142-as, was cloned several times and also appeared at a frequency of 30%. In small intestine, too few miRNA sequences were obtained to permit statistical analysis. This was due to strong RNase activity in this tissue, which caused significant breakdown of abundant non-coding RNAs, e.g. rRNA, so that the fraction of miRNA in the cloned sequences was very low. For the same reason, no miRNA sequences were obtained from pancreas.

To gain insights in neural tissue miRNA distribution, we analyzed cortex, cerebellum and midbrain. Similar to heart, liver and small intestine, variants of a particular miRNA, miR-124, dominated and accounted for 25 to 48% of all brain miRNAs. miR-101, -127, -128, -131, and -132, also cloned from brain tissues, were further analyzed by Northern blotting and shown to be predominantly brain-specific. Northern blot analysis was performed as described in Example 1. tRNAs and 5S rRNA were detected by ethidium staining of polyacrylamide gels prior to transfer to verify equal loading. Blots were stripped by boiling in deionized water for 5 min, and reprobed up to 4 times until the 21-nt signals became too weak for detection.

miR-125a and miR-125b are very similar to the sequence of *C. elegans* lin-4 stRNA and may represent its orthologs (FIG. 6A). This is of great interest because, unlike let-7 that was readily detected in other species, lin-4 has acquired a few mutations in the central region and thus escaped bioinformatic database searches. Using the mouse sequence miR-125b, we could readily identify its ortholog in the *D. melanogaster* genome. miR-125a and miR-125b differ only by a central diuridine insertion and a U to C change. miR-125b is very similar to lin-4 stRNA with the differences located only in the central region, which is presumed to be bulged out during target mRNA recognition [41]. miR-125a and miR-125b were cloned from brain tissue, but expression was also detected by Northern analysis in other tissues, consistent with the role for lin-4 in regulating neuronal remodeling by controlling lin-14 expression [43]. Unfortunately, orthologs to *C. elegans* lin-14 have not been described and miR-125 targets remain to be identified in *D. melanogaster* or mammals. Finally, miR-125b expression is also developmentally regulated and only detectable in pupae and adult but not in embryo or larvae of *D. melanogaster* (FIG. 6B).

Sequence comparison of mouse miRNAs with previously described miRNA reveals that miR-99b and miR-99a are similar to *D. melanogaster*, mouse and human miR-10 as well as *C. elegans* miR-51 [36], miR-141 is similar to *D. melanogaster* miR-8, miR-29b is similar to *C. elegans* miR-83, and miR-131 and miR-142-s are similar to *D. melanogaster* miR-4 and *C. elegans* miR-79 [36]. miR-124a is conserved between invertebrates and vertebrates. In this respect it should be noted that for almost every miRNA cloned from mouse was also encoded in the human genome, and frequently detected in other vertebrates, such as the pufferfish, *Fugu rubripes*, and the zebrafish, *Danio rerio*. Sequence conservation may point to conservation in function of these miRNAs. Comprehensive information about orthologous sequences is listed in FIG. 7.

In two cases both strands of miRNA precursors were cloned (Table 3), which was previously observed once for a *C. elegans* miRNA [36]. It is thought that the most frequently cloned strand of a miRNA precursor represents the functional miRNA, which is miR-30c-s and miR-142-as, s and as indicating the 5' or 3' side of the fold-back structure, respectively.

The mir-142 gene is located on chromosome 17, but was also found at the breakpoint junction of a t(8;17) translocation, which causes an aggressive B-cell leukemia due to strong up-regulation of a translocated MYC gene (441. The translocated MYC gene, which was also truncated at the first exon, was located only 4-nt downstream of the 3'-end of the miR-142 precursor. This suggests that translocated MYC was under the control of the upstream miR-142 promoter. Alignment of mouse and human miR-142 containing EST sequences indicate an approximately 20 nt conserved sequence element downstream of the mir-142 hairpin. This element was lost in the translocation. It is conceivable that the absence of the conserved downstream sequence element in the putative miR-142/mRNA fusion prevented the recognition of the transcript as a miRNA precursor and therefore may have caused accumulation of fusion transcripts and overexpression of MYC.

miR-155, which was cloned from colon, is excised from the known noncoding BIC RNA [47]. BIC was originally identified as a gene transcriptionally activated by promoter insertion at a common retroviral integration site in B cell lymphomas induced by avian leukosis virus. Comparison of BIC cDNAs from human, mouse and chicken revealed 78% identity over 138 nucleotides [47]. The identity region covers the miR-155 fold-back precursor and a few conserved boxes downstream of the fold-back sequence. The relatively high level of expression of BIC in lymphoid organs and cells in human, mouse and chicken implies an evolutionary conserved function, but BIC RNA has also been detected at low levels in non-hematopoietic tissues [47].

Another interesting observation was that segments of perfect complementarity to miRNAs are not observed in mRNA sequences or in genomic sequences outside the miRNA inverted repeat. Although this could be fortuitous, based on the link between RNAi and miRNA processing [11, 13, 43] it may be speculated that miRNAs retain the potential to cleave perfectly complementary target RNAs. Because translational control without target degradation could provide more flexibility it may be preferred over mRNA degradation.

In summary, 63 novel miRNAs were identified from mouse and 4 novel miRNAs were identified from human Soas-2 osteosarcoma cells (Table 3 and Table 4), which are conserved in human and often also in other non-mammalian vertebrates. A few of these miRNAs appear to be extremely tissue-specific, suggesting a critical role for some miRNAs in tissue-specification and cell lineage decisions. We may have also identified the fruitfly and mammalian ortholog of *C. elegans* lin-4 stRNA. The establishment of a comprehensive list of miRNA sequences will be instrumental for bioinformatic approaches that make use of completed genomes and the power of phylogenetic comparison in order to identify miRNA-regulated target mRNAs.

REFERENCES AND NOTES

1. R. C. Lee, R. L. Feinbaum, V. Ambros, Cell 75, 843 (1993).
2. B. J. Reinhart et al., Nature 403, 901 (2000).
3. V. Ambros, Curr. Opin. Genet. Dev. 10, 428 (2000).
4. E. G. Moss, Curr. Biol. 10, R436 (2000).
5. F. Slack, G. Ruvkun, Annu. Rev. Genet. 31, 611 (1997).
6. A. E Pasquinelli et al., Nature 408, 86 (2000).
7. S. M. Elbashir et al., Nature 411, 494 (2001).
8. S. M. Elbashir, W. Lendeckel, T. Tuschl, Genes & Dev. 15, 188 (2001).
9. A. J. Hamilton, D. C. Baulcombe, Science 286, 950 (1999).
10. S. M. Hammond, E. Bernstein, D. Beach, G. J. Hannon, Nature 404, 293 (2000).
11. P. D. Zamore, T. Tuschl, P. A. Sharp, D. P. Bartel, Cell 101, 25 (2000).
12. G. Hutvágner, J. McLachlan, É. Bálint, T. Tuschl, P. D. Zamore, Science 93, 834 (2001).
13. A. Grishok at al., Cell 106, 23 (2001).
14. Cloning of 19- to 24-nt RNAs from *D. melanogaster* 0-2 h embryo lysate was performed as described (8). For cloning of HeLa miRNAs, 1 mg of HeLa total RNA was separated on a 15% denaturing polyacrylamide gel and RNA of 19- to 25-nt size was recovered. A 5' phosphorylated 3' adapter oligonucleotide (5' pUUUaaccgcgaattccagx: uppercase, RNA; lowercase, DNA; p, phosphate; x, 4-hydroxymethylbenzyl; SEQ ID NO:54) and a 5' adapter oligonucleotide (5' acggaattcctcactAAA: uppercase, RNA; lowercase, DNA; SEQ ID NO:55) were ligated to the short HeLa cell RNAs. RT/PCR was performed with 3' primer (5' GACTAGCTGGAATTCGCGGTTAAA; SEQ ID NO:56) and 5' primer (5' CAGCCAACGGAATTCCTCACTAAA; SEQ ID NO:57), and followed by concatamerization after Eco RI digestion and T4 DNA ligation (8). After ligation of concatamers into pCR2.1 TOPO vectors, about 100 clones were selected and subjected to sequencing.
15. I. Schneider, J Embryol Exp Morphol 27, 353 (1972).
16. R. Feinbaum, V. Ambros, Dev. Biol. 210, 87 (1999).
17. S. M. Hammond, S. Boettcher, A. A. Caudy, R. Kobayashi, G. J. Hannon, Science 293, 1146 (2001).
18. A. A. Aravin et al., Curr. Biol. 11, 1017 (2001).
19. H. Tabara et al., Cell 99, 123 (1999).
20. M. Fagard, S. Boutet, J. B. Morel, C. Bellini, H. Vaucheret, Proc. Natl. Acad. Sci. USA 97, 11650 (2000).
21. C. Catalanotto, G. Azzalin, G. Macino, C. Cogoni, Nature 404, 245 (2000):
22. S. R. Eddy, Curr. Opin. Genet. Dev. 9, 695 (1999).
23. J. Cavaille et al., Proc. Natl. Acad. Sci. USA 97, 14311 (2000).
24. A; Hüttenhofer at al., EMBO J. 20, 2943 (2001).
25. L. Argaman et al., Curr. Biol. 11, 941 (2001).
26. K. M. Wassarman, F. Repoila, C. Rosenow, G. Storz, S. Gottesman, Genes & Dev. 15, 1637 (2001).
27. Supplementary Web material is available on Science Online at www.sciencemag.org/cgi/content/full/xxx
28. D. H. Mathews, J. Sabina, M. Zuker, D. H. Turner, J. Mol. Biol. 288, 911 (1999).
29. E. Bernstein, A. A. Caudy, S. M. Hammond, G. J. Hannon, Nature 409, 363 (2001).
30. Graham, F. L. and van der Eb, A. J., (1973), Virol. 52, 456.
31. McCutchan, J. H. and Pagano, J. S., (1968), J. Natl. Cancer Inst. 41, 351.
32. Chu, G. et al., (1987), Nucl. Acids Res. 15, 1311.
33. Fraley, R. et al., (1980), J. Biol. Chem. 255, 10431.
34. Capecchi, M. R., (1980), Cell 22, 479.
35. Felgner, P. L. et al., (1987), Proc. Natl. Acad. Sci. USA 84, 7413.
36. Lau N. C., Lim L. P., Weinstein E. G., Bartel D. P., (2001), Science 2.94, 858-862.
37. Lee R. C., Ambros V., (2001), Science 2.94, 862-864.
38. Ambros V., (2001), Cell 107, 823-826.
39. Ambros V., Horvitz H.R., (1984), Science 226, 409-416.
40. Wightman B., Ha I., Ruvkun G., (1993), Cell 75, 855-862.
41. Rougvie A. E., (2001), Nat. Rev. Genet. 2, 690-701.

42. Ketting R. F., Fischer S. E., Bernstein E., Sijen T., Hannon G. J., Plasterk R. H., (2001), Genes & Dev. 15, 2654-2659.
43. Hallam S. J., Jin Y., (1998), Nature 395, 78-82.
44. Gauwerky C. E., Huebner K., Isobe M., Nowell P. C., Croce C. M., (1989), Proc. Natl. Acad. Sci. USA 86, 8867-8871.
45. P. Chomczynski, N. Sacchi, Anal Biochem 162, 156, (1987).
46. Mourelatos Z., Dostie J., Paushkin S., Sharma A., Charroux B., Abel L., J. R., Mann M., Dreyfuss G., (2002), Genes & Dev., in press.
47. Tam W., (2001), Gene 274, 157-167.

TABLE 1

*D. melanogaster* miRNAs. The sequences given represent the most abundant, and typically longest miRNA sequence identified by cloning; miRNAs frequently vary in length by one or two nucleotides at their 3' termini. From 222 short RNAs sequenced, 69 (31%) corresponded to miRNAs, 103 (46%) to already characterized functional RNAs (rRNA, 7SL RNA, tRNAs), 30 (14%) to transposon RNA fragments, and 20 (10%) sequences with no database entry. The frequency (freq.) for cloning a particular miRNA relative to all identified miRNAs is indicated in percent. Results of Northern blotting of total RNA isolated from staged populations of *D. melanogaster* are summarized. E, embryo; L, larval stage; P, pupae; A, adult; S2, Schneider-2 cells. The strength of the signal within each blot is represented from strongest (+++) to undetected (-). let-7 stRNA was probed as control. Genbank accession numbers and homologs of miRNAs identified by database searching in other species are provided as supplementary material.

| miRNA | sequence (5' to 3') | freq. (%) | E 0-3 h | E 0-6 h | L1+ L2 | L3 | P | A | S2 |
|---|---|---|---|---|---|---|---|---|---|
| miR-1 | UGGAAUGUAAAGAAGUAUGGAG (SEQ ID NO: 58) | 32 | + | + | +++ | +++ | ++ | +++ | - |
| miR-2a* | UAUCACAGCCAGCUUUGAUGAGC (SEQ ID NO: 59) | 3 | | | | | | | |
| miR-2b* | UAUCACAGCCAGCUUUGAGGAGC (SEQ ID NO: 60) | 3 | ++ | ++ | ++ | +++ | ++ | + | +++ |
| miR-3 | UCACUGGGCAAAGUGUGUCUCA# | 9 | +++ | +++ | - | - | - | - | - |
| miR-4 | AUAAAGCUAGACAACCAUUGA (SEQ ID NO: 62) | 6 | +++ | +++ | - | - | - | - | - |
| miR-5 | AAAGGAACGAUCGUUGUGAUAUG (SEQ ID NO: 63) | 1 | +++ | +++ | +/- | +/- | - | - | - |
| miR-6 | UAUCACAGUGGCUGUUCUUUUU (SEQ ID NO: 64) | 13 | +++ | +++ | +/- | +/- | - | - | - |
| miR-7 | UGGAAGACUAGUGAUUUUGUUGU (SEQ ID NO: 65) | 4 | +++ | ++ | +/- | +/- | +/- | +/- | +/- |
| miR-8 | UAAUACUGUCAGGUAAAGAUGUC (SEQ ID NO: 66) | 3 | +/- | +/- | +++ | +++ | + | +++ | - |
| miR-9 | UCUUUGGUUAUCUAGCUGUAUGA (SEQ ID NO: 67) | 7 | +++ | ++ | +++ | +++ | +++ | +/- | - |
| miR-10 | ACCCUGUAGAUCCGAAUUUGU (SEQ ID NO: 68) | 1 | + | + | ++ | +++ | +/- | + | - |
| miR-11 | CAUCACAGUCUGAGUUCUUGC (SEQ ID NO: 69) | 7 | +++ | +++ | +++ | +++ | +++ | + | - |
| miR-12 | UGAGUAUUACAUCAGGUACUGGU (SEQ ID NO: 70) | 7 | + | + | ++ | ++ | + | +++ | +/- |
| miR-13a* | UAUCACAGCCAUUUUGACGAGU (SEQ ID NO: 71) | 1 | +++ | +++ | +++ | +++ | + | +++ | +++ |
| miR-13b* | UAUCACAGCCAUUUUGAUGAGU (SEQ ID NO: 72) | 0 | | | | | | | |

TABLE 1-continued

D. melanogaster miRNAs. The sequences given represent the most abundant, and typically longest miRNA sequence identified by cloning; miRNAs frequently vary in length by one or two nucleotides at their 3' termini. From 222 short RNAs sequenced, 69 (31%) corresponded to miRNAs, 103 (46%) to already characterized functional RNAs (rRNA, 7SL RNA, tRNAs), 30 (14%) to transposon RNA fragments, and 20 (10%) sequences with no database entry. The frequency (freq.) for cloning a particular miRNA relative to all identified miRNAs is indicated in percent. Results of Northern blotting of total RNA isolated from staged populations of D. melanogaster are summarized. E, embryo; L, larval stage; P, pupae; A, adult; S2, Schneider-2 cells. The strength of the signal within each blot is represented from strongest (+++) to undetected (-). let-7 stRNA was probed as control. Genbank accession numbers and homologs of miRNAs identified by database searching in other species are provided as supplementary material.

| miRNA | sequence (5' to 3') | freq. (%) | E 0-3 h | E 0-6 h | L1+ L2 | L3 | P | A | S2 |
|---|---|---|---|---|---|---|---|---|---|
| miR-14 | UCAGUCUUUUCUCUCUCCUA (SEQ ID NO: 73) | 1 | - | - | - | - | - | - | - |
| let-7 | UGAGGUAGUAGGUUGUAUAGUU (SEQ ID NO: 74) | 0 | - | - | - | - | +++ | +++ | - |

# = (SEQ ID NO: 61)
*Similar miRNA sequences are difficult to distinguish by Northern blotting because of potential cross-hybridization of probes.

TABLE 2

Human miRNAs. From 220 short RNAs sequenced, 100 (45%) corresponded to miRNAs, 53 (24%) to already characterized functional RNAs (rRNA, snRNAs, tRNAs), and 67 (30%) sequences with no database entry. Results of Northern blotting of total RNA isolated from different vertebrate species and S2 cells are indicated. For legend, see Table 1.

| miRNA | sequence (5' to 3') | freq. (%) | HeLa cells | mouse kidney | adult fish | frog ovary | S2 |
|---|---|---|---|---|---|---|---|
| let-7a* | UGAGGUAGUAGGUUGUAUAGUU# | 10 | +++ | +++ | +++ | - | - |
| let-7b* | UGAGGUAGUAGGUUGUGUGGUU (SEQ ID NO: 76) | 13 | | | | | |
| let-7c* | UGAGGUAGUAGGUUGUAUGGUU (SEQ ID NO: 77) | 3 | | | | | |
| let-7d* | AGAGGUAGUAGGUUGCAUAGU (SEQ ID NO: 78) | 2 | +++ | +++ | +++ | - | - |
| let-7e* | UGAGGUAGGAGGUUGUAUAGU (SEQ ID NO: 79) | 2 | +++ | +++ | +++ | - | - |
| let-7f* | UGAGGUAGUAGAUUGUAUAGUU (SEQ ID NO: 80) | 1 | | | | | |
| miR-15 | UAGCAGCACAUAAUGGUUUGUG (SEQ ID NO: 81) | 3 | +++ | ++ | + | +/- | - |
| miR-16 | UAGCAGCACGUAAAUAUUGGCG (SEQ ID NO: 82) | 10 | +++ | + | +/- | +/- | - |
| miR-17 | ACUGCAGUGAAGGCACUUGU (SEQ ID NO: 83) | 1 | +++ | - | - | - | - |
| miR-18 | UAAGGUGCAUCUAGUGCAGAUA (SEQ ID NO: 84) | 2 | +++ | - | - | - | - |
| miR-19a* | UGUGCAAAUCUAUGCAAAACUGA (SEQ ID NO: 85) | 1 | +++ | - | +/- | - | - |
| miR-19b* | UGUGCAAAUCCAUGCAAAACUGA (SEQ ID NO: 86) | 3 | | | | | |

TABLE 2-continued

Human miRNAs. From 220 short RNAs sequenced, 100 (45%) corresponded to miRNAs, 53 (24%) to already characterized functional RNAs (rRNA, snRNAs, tRNAs), and 67 (30%) sequences with no database entry. Results of Northern blotting of total RNA isolated from different vertebrate species and S2 cells are indicated. For legend, see Table 1.

| miRNA | sequence (5' to 3') | freq. (%) | HeLa cells | mouse kidney | adult fish | frog ovary | S2 |
|---|---|---|---|---|---|---|---|
| miR-20 | UAAAGUGCUUAUAGUGCAGGUA (SEQ ID NO: 87) | 4 | +++ | − | + | − | − |
| miR-21 | UAGCUUAUCAGACUGAUGUUGA (SEQ ID NO: 88) | 10 | +++ | + | ++ | − | − |
| miR-22 | AAGCUGCCAGUUGAAGAACUGU (SEQ ID NO: 89) | 10 | +++ | +++ | + | +/− | − |
| miR-23 | AUCACAUUGCCAGGGAUUUCC (SEQ ID NO: 90) | 2 | +++ | +++ | +++ | + | − |
| miR-24 | UGGCUCAGUUCAGCAGGAACAG (SEQ ID NO: 91) | 4 | ++ | +++ | ++ | − | − |
| miR-25 | CAUUGCACUUGUCUCGGUCUGA (SEQ ID NO: 92) | 3 | +++ | + | ++ | − | − |
| miR-26a* | UUCAAGUAAUCCAGGAUAGGCU (SEQ ID NO: 93) | 2 | + | ++ | +++ | − | − |
| miR-26b* | UUCAAGUAAUUCAGGAUAGGUU (SEQ ID NO: 94) | 1 | | | | | − |
| miR-27 | UUCACAGUGGCUAAGUUCCGCU (SEQ ID NO: 95) | 2 | +++ | +++ | ++ | − | − |
| miR-28 | AAGGAGCUCACAGUCUAUUGAG (SEQ ID NO: 96) | 2 | +++ | +++ | − | − | − |
| miR-29 | CUAGCACCAUCUGAAAUCGGUU (SEQ ID NO: 97) | 2 | + | +++ | +/− | − | − |
| miR-30 | CUUUCAGUCGGAUGUUUGCAGC (SEQ ID NO: 98) | 2 | +++ | +++ | +++ | − | − |
| miR-31 | GGCAAGAUGCUGGCAUAGCUG (SEQ ID NO: 99) | 2 | +++ | − | − | − | − |
| miR-32 | UAUUGCACAUUACUAAGUUGC (SEQ ID NO: 100) | 1 | − | − | − | − | − |
| miR-33 | GUGCAUUGUAGUUGCAUUG (SEQ ID NO: 101) | 1 | − | − | − | − | − |
| miR-1 | UGGAAUGUAAAGAAGUAUGGAG (SEQ ID NO: 102) | 0 | − | − | + | − | − |
| miR-7 | UGGAAGACUAGUGAUUUUGUUGU (SEQ ID NO: 103) | 0 | + | − | +/− | − | +/− |
| miR-9 | UCUUUGGUUAUCUAGCUGUAUGA (SEQ ID NO: 104) | 0 | − | − | − | − | − |
| miR-10 | ACCCUGUAGAUCCGAAUUUGU (SEQ ID NO: 105) | 0 | − | + | − | − | − |

# = (SEQ ID NO: 75)
*Similar miRNA sequences are difficult to distinguish by Northern blotting because of potential cross-hybridization of probes.

TABLE 3

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

| | | Number of clones | | | | | | | |
|---|---|---|---|---|---|---|---|---|---|
| miRNA | sequence (5' to 3') | ht | lv | sp | si | co | cx | cb | mb |
| let-7a | UGAGGUAGUAGGUUGUAUAGUU (SEQ ID NO: 106) | 3 | | | 1 | 1 | | | 7 |
| let-7b | UGAGGUAGUAGGUUGUGUGGUU (SEQ ID NO: 107) | | 1 | 1 | | | | 2 | 5 |
| let-7c | UGAGGUAGUAGGUUGUAUGGUU (SEQ ID NO: 108) | | 2 | | | | 2 | 5 | 19 |
| let-7d | AGAGGUAGUAGGUUGCAUAGU (SEQ ID NO: 109) | 2 | | | | 2 | 2 | | 2 |
| let-7e | UGAGGUAGGAGGUUGUAUAGU (SEQ ID NO: 110) | | | 1 | | | | | 2 |
| let-7f | UGAGGUAGUAGAUUGUAUAGUU (SEQ ID NO: 111) | | 2 | | | | | 3 | 3 |
| let-7g | UGAGGUAGUAGUUUGUACAGUA (SEQ ID NO: 112) | | | | | | | 1 | 1 | 2 |
| let-7h | UGAGGUAGUAGUGUGUACAGUU (SEQ ID NO: 113) | | | | | | | 1 | 1 |
| let-7i | UGAGGUAGUAGUUUGUGCU (SEQ ID NO: 114) | | | | | | | 1 | 1 |
| miR-1b | UGGAAUGUAAAGAAGUAUGUAA (SEQ ID NO: 115) | 4 | 2 | | | | | | 1 |
| miR-1c | UGGAAUGUAAAGAAGUAUGUAC (SEQ ID NO: 116) | 7 | | | | | | | |
| miR-1d | UGGAAUGUAAAGAAGUAUGUAUU (SEQ ID NO: 117) | 16 | | | | | | | 1 |
| miR-9 | UCUUUGGUUAUCUAGCUGUAUGA (SEQ ID NO: 118) | | | | | | | 3 | 4 | 4 |
| miR-15a | UAGCAGCACAUAAUGGUUUGUG (SEQ ID NO: 119) | 1 | | | | | | | 2 |
| miR-15b | UAGCAGCACAUCAUGGUUUACA (SEQ ID NO: 120) | 1 | | | | | | | |
| miR-16 | UAGCAGCACGUAAAUAUUGGCG (SEQ ID NO: 121) | 1 | | | 1 | 2 | 1 | 2 | 3 |
| miR-18 | UAAGGUGCAUCUAGUGCAGAUA (SEQ ID NO: 122) | | | 1 | | | | | |
| miR-19b | UGUGCAAAUCCAUGCAAAACUGA (SEQ ID NO: 123) | | | 1 | | | | | |
| miR-20 | UAAAGUGCUUAUAGUGCAGGUAG (SEQ ID NO: 124) | | | | | 1 | | | |

TABLE 3-continued

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

|  |  | Number of clones | | | | | | | |
|---|---|---|---|---|---|---|---|---|---|
| miRNA | sequence (5' to 3') | ht | lv | sp | si | co | cx | cb | mb |
| miR-21 | UAGCUUAUCAGACUGAUGUUGA (SEQ ID NO: 125) | 1 | | 1 | 2 | 1 | | | |
| miR-22 | AAGCUGCCAGUUGAAGAACUGU (SEQ ID NO: 126) | 2 | 1 | | 1 | | | 1 | 2 |
| miR-23a | AUCACAUUGCCAGGGAUUUCC (SEQ ID NO: 127) | 1 | | | | | | | |
| miR-23b | AUCACAUUGCCAGGGAUUACCAC (SEQ ID NO: 128) | | | | | | 1 | | |
| miR-24 | UGGCUCAGUUCAGCAGGAACAG (SEQ ID NO: 129) | 1 | | | | 1 | 1 | | 1 |
| miR-26a | UUCAAGUAAUCCAGGAUAGGCU (SEQ ID NO: 130) | | | | | | | 3 | 2 |
| miR-26b | UUCAAGUAUUCAGGAUAGGUU (SEQ ID NO: 131) | | | 2 | | | | 4 | 1 |
| miR-27a | UUCACAGUGGCUAAGUUCCGCU (SEQ ID NO: 132) | 1 | | 2 | | 1 | 1 | 2 | 1 |
| miR-27b | UCACAGUGGCUAAGUUCUG (SEQ ID NO: 133) | | | | | | | | 1 |
| miR-29a | CUAGCACCAUCUGAAAUCGGUU (SEQ ID NO: 134) | 1 | | | | 1 | | 1 | |
| miR-29b/ miR-102 | UAGCACCAUUUGAAAUCAGUGUU (SEQ ID NO: 135) | 1 | | | | 1 | 5 | | 3 |
| miR-29c/ | UAGCACCAUUUGAAAUCGGUUA (SEQ ID NO: 136) | 1 | | | | | 3 | | 1 |
| miR-30a-s/ miR-97 | UGUAAACAUCCUCGACUGGAAGC (SEQ ID NO: 137) | | | 1 | | | 1 | | 1 |
| miR-30a-as<sup>a</sup> | CUUUCAGUCGGAUGUUUGCAGC (SEQ ID NO: 138) | | | | | | | 1 | |
| miR-30b | UGUAAACAUCCUACACUCAGC (SEQ ID NO: 139) | | | | 1 | | | 2 | |
| miR-30c | UGUAAACAUCCUACACUCUCAGC (SEQ ID NO: 140) | 2 | | | | | 1 | 1 | |
| miR-30d | UGUAAACAUCCCCGACUGGAAG (SEQ ID NO: 141) | | 1 | | | | | | |
| miR-99a/ miR-99 | ACCCGUAGAUCCGAUCUUGU (SEQ ID NO: 142) | | | | | | | 1 | |

TABLE 3-continued

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

| miRNA | sequence (5' to 3') | ht | lv | sp | si | co | cx | cb | mb |
|---|---|---|---|---|---|---|---|---|---|
| miR-99b | CACCCGUAGAACCGACCUUGCG (SEQ ID NO: 143) | | | | | | | 1 | |
| miR-101 | UACAGUACUGUGAUAACUGA (SEQ ID NO: 144) | | | | | | 2 | 1 | 1 |
| miR-122a | UGGAGUGUGACAAUGGUGUUUGU (SEQ ID NO: 145) | | 3 | | | | | | |
| miR-122b | UGGAGUGUGACAAUGGUGUUUGA (SEQ ID NO: 146) | | 11 | | | | | | |
| miR-122a, b | UGGAGUGUGACAAUGGUGUUUG (SEQ ID NO: 147) | | 23 | | | | | | |
| miR-123 | CAUUAUUACUUUUGGUACGCG (SEQ ID NO: 148) | 1 | 2 | | | | | | |
| miR-124a[b] | UUAAGGCACGCGG-UGAAUGCCA (SEQ ID NO: 149) | | | | 1 | | 37 | 41 | 24 |
| miR-124b | UUAAGGCACGCGGGUGAAUGC (SEQ ID NO: 150) | | | | | | 1 | 3 | |
| miR-125a | UCCCUGAGACCCUUUAACCUGUG (SEQ ID NO: 151) | | | | | | 1 | 1 | |
| miR-125b | UCCCUGAGACCCU--AACUUGUGA (SEQ ID NO: 152) | | | | | | | 1 | |
| miR-126 | UCGUACCGUGAGUAAUAAUGC (SEQ ID NO: 153) | 4 | | | | | | 1 | |
| miR-127 | UCGGAUCCGUCUGAGCUUGGCU (SEQ ID NO: 154) | | | | | | | 1 | |
| miR-128 | UCACAGUGAACCGGUCUCUUUU (SEQ ID NO: 155) | | | | | | 2 | 2 | 2 |
| miR-129 | CUUUUUCGGUCUGGGCUUGC (SEQ ID NO: 156) | | | | | | | 1 | |
| miR-130 | CAGUGCAAUGUUAAAAGGGC (SEQ ID NO: 157) | | | | | | | 1 | |
| miR-131 | UAAAGCUAGAUAACCGAAAGU (SEQ ID NO: 158) | | | | | | 1 | 1 | 1 |
| miR-132 | UAACAGUCUACAGCCAUGGUCGU (SEQ ID NO: 159) | | | | | | | 1 | |
| miR-133 | UUGGUCCCCUUCAACCAGCUGU (SEQ ID NO: 160) | 4 | | | | | 1 | | |
| miR-134 | UGUGACUGGUUGACCAGAGGGA (SEQ ID NO: 161) | | | | | | | 1 | |

TABLE 3-continued

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

| miRNA | sequence (5' to 3') | ht | lv | sp | si | co | cx | cb | mb |
|---|---|---|---|---|---|---|---|---|---|
| miR-135 | UAUGGCUUUUAUUCCUAUGUGAA (SEQ ID NO: 162) | | | | | | 1 | | |
| miR-136 | ACUCCAUUUGUUUUGAUGAUGGA (SEQ ID NO: 163) | | | | | | 1 | | |
| miR-137 | UAUUGCUUAAGAAUACGCGUAG (SEQ ID NO: 164) | | | | | | 1 | | 1 |
| miR-138 | AGCUGGUGUUGUGAAUC (SEQ ID NO: 165) | | | | | | 1 | | |
| miR-139 | UCUACAGUGCACGUGUCU (SEQ ID NO: 166) | | | | | | 1 | 1 | |
| miR-140 | AGUGGUUUUACCCUAUGGUAG (SEQ ID NO: 167) | | | | 1 | | | | |
| miR-141 | AACACUGUCUGGUAAAGAUGG (SEQ ID NO: 168) | | | | 1 | 1 | | 1 | |
| miR-142-s | CAUAAAGUAGAAAGCACUAC (SEQ ID NO: 169) | | | | | 1 | 1 | | |
| miR-142-as[b] | UGUAGUGUUUCCUACUUUAUGG (SEQ ID NO: 170) | | | | 1 | 1 | 6 | | |
| miR-143 | UGAGAUGAAGCACUGUAGCUCA (SEQ ID NO: 171) | 3 | | 7 | | | 2 | | 1 |
| miR-144 | UACAGUAUAGAUGAUGUACUAG (SEQ ID NO: 172) | 2 | | | | 1 | | | |
| miR-145 | GUCCAGUUUUCCCAGGAAUCCCUU (SEQ ID NO: 173) | 1 | | | | | | | |
| miR-146 | UGAGAACUGAAUUCCAUGGGUUU (SEQ ID NO: 174) | 1 | | | | | | | |
| miR-147 | GUGUGUGGAAAUGCUUCUGCC (SEQ ID NO: 175) | | | | 1 | | | | |
| miR-148 | UCAGUGCACUACAGAACUUUGU (SEQ ID NO: 176) | | | | 1 | | | | |
| miR-149 | UCUGGCUCCGUGUCUUCACUCC (SEQ ID NO: 177) | 1 | | | | | | | |
| miR-150 | UCUCCCAACCCUUGUACCAGUGU (SEQ ID NO: 178) | | | | | | 1 | | |
| miR-151 | CUAGACUGAGGCUCCUUGAGGU (SEQ ID NO: 179) | | | | | | 1 | | |
| miR-152 | UCAGUGCAUGACAGAACUUGG (SEQ ID NO: 180) | | | | | | 1 | | |

TABLE 3-continued

Mouse miRNAs. The sequences indicated represent the longest miRNA sequences identified by cloning. The 3'-terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes, which are accommodated as G-U wobble base pairs during target recognition. miRNAs with the suffix -s or -as indicate RNAs derived from either the 5'-half or the 3'-half of a miRNA precursor. Mouse brains were dissected into midbrain, mb, cortex, cx, cerebellum, cb. The tissues analyzed were heart, ht; liver, lv; small intestine, si; colon, co; cortex, ct; cerebellum, cb; midbrain, mb.

| miRNA | sequence (5' to 3') | ht | lv | sp | si | co | cx | cb | mb |
|---|---|---|---|---|---|---|---|---|---|
| miR-153 | UUGCAUAGUCACAAAAGUGA (SEQ ID NO: 181) | | | | | | | | 1 |
| miR-154 | UAGGUUAUCCGUGUUGCCUUCG (SEQ ID NO. 182) | | | | | | | | 1 |
| miR-155 | UUAAUGCUAAUUGUGAUAGGGG (SEQ ID NO: 183) | | | | | | | 1 | |

[a] The originally described miR-30 was renamed to miR-30a-as in order to distinguish it from the miRNA derived from the opposite strand of the precursor encoded by the mir-30a gene. miR-30a-s is equivalent to miR-97 [46].
[b] A 1-nt length heterogeneity is found on both 5' and 3' end. The 22-nt-miR sequence is shown, but only 21-nt miRNAs were cloned.

TABLE 4

Mouse and human miRNAs. The sequences indicated represent the longest miRNA sequences identified by cloning. The 3' terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes; which are accommodated as G-U wobble base pairs during target recognition. Mouse brains were dissected into midbrain, mb, cortex, cx, cerebellum, cb. The tissues analyzed were lung, ln; liver, lv; spleen, sp; kidney, kd; skin, sk; testis, ts; ovary, ov; thymus, thy; eye, ey; cortex, ct; cerebellum, cb; midbrain, mb. The human osteosarcoma cells SAOS-2 cells contained an inducible p53 gene (p53−, uninduced p53; p53+, induced p53); the differences in miRNAs identified from induced and uninduced SAOS cells were not statistically significant.

| | | number of clones | | | | | | | | | | |
|---|---|---|---|---|---|---|---|---|---|---|---|---|
| | | mouse tissues | | | | | | | | human SAOS-2 cells | | |
| miRNA | Sequence (5' to 3') | ln | lv | sp | kd | sk | ts | ov | thy | ey | p53− | p53+ |
| miR-C1 | AACAUUCAACGCUGUCGGUGAGU | 1 | | | 1 | | | | | 2 | | (SEQ ID NO. 184) |
| miR-C2 | UUUGGCAAUGGUAGAACUCACA | | | | | | | | | 1 | | (SEQ ID NO. 185) |
| miR-C3 | UAUGGCACUGGUAGAAUUCACUG | | | | | | | | | 1 | | (SEQ ID NO. 186) |
| miR-C4 | CUUUUUGCGGUCUGGGCUUGUU | | | | | 1 | | | | 1 | 1 | (SEQ ID NO. 187) |
| miR-C5 | UGGACGGAGAACUGAUAAGGGU | | | | | | | | | 2 | | (SEQ ID NO. 188) |
| miR-C6 | UGGAGAGAAAGGCAGUUC | | | | | | | | | 1 | | (SEQ ID NO. 189) |
| miR-C7 | CAAAGAAUUCUCCUUUUGGGCUU | | | | | | | | | 1 | 1 | (SEQ ID NO. 190) |

TABLE 4-continued

Mouse and human miRNAs. The sequences indicated represent the longest miRNA sequences identified by cloning. The 3' terminus of miRNAs is often truncated by one or two nucleotides. miRNAs that are more than 85% identical in sequence (i.e. share 18 out of 21 nucleotides) or contain 1- or 2-nucleotide internal deletions are referred to by the same gene number followed by a lowercase letter. Minor sequence variations between related miRNAs are generally found near the ends of the miRNA sequence and are thought to not compromise target RNA recognition. Minor sequence variations may also represent A to G and C to U changes; which are accommodated as G-U wobble base pairs .during target recognition. Mouse brains were dissected into midbrain, mb, cortex, cx, cerebellum, cb. The tissues analyzed were lung, ln; liver, lv; spleen, sp; kidney, kd; skin, sk; testis, ts; ovary, ov; thymus, thy; eye, ey; cortex, ct; cerebellum, cb; midbrain, mb. The human osteosarcoma cells SAOS-2 cells contained an inducible p53 gene (p53-, uninduced p53; p53+, induced p53); the differences in miRNAs identified from induced and uninduced SAOS cells were not statistically significant.

| | | number of clones | | | | | | | | | | |
|---|---|---|---|---|---|---|---|---|---|---|---|---|
| | | mouse tissues | | | | | | | | | human SAOS-2 cells | |
| miRNA | Sequence (5' to 3') | ln | lv | sp | kd | sk | ts | ov | thy | ey | p53- | p53+ |
| miR-C8 | UCGUGUCUUGUGUUGCAGCCGG | | | 1 | | | | | | | | (SEQ ID NO. 191) |
| miR-C9 | UAACACUGUCUGGUAACGAUG | | | 1 | | | | | | | | (SEQ ID NO. 192) |
| miR-C10 | CAUCCCUUGCAUGGUGGAGGGU | | | 1 | | | | | | | | (SEQ ID NO. 193) |
| miR-C11 | GUGCCUACUGAGCUGACAUCAGU | | | 1 | | | | | | | | (SEQ ID NO. 194) |
| miR-C12 | UGAUAUGUUUGAUAUAUUAGGU | | | 2 | | | | | | | | (SEQ ID NO. 195) |
| miR-C13 | CAACGGAAUCCCAAAAGCAGCU | | 2 | 1 | | | | | | | | (SEQ ID NO. 196) |
| miR-C14 | CUGACCUAUGAAUUGACA | | 2 | 1 | | | | | | | | (SEQ ID NO. 197) |
| miR-C15 | UACCACAGGGUAGAACCACGGA | | | 1 | | | | | | | | (SEQ ID NO. 198) |
| miR-C16 | AACUGGCCUACAAAGUCCCCAG | | | 1 | | | | | | | | (SEQ ID NO. 199) |
| miR-C17 | UGUAACAGCAACUCCAUGUGGA | | | 1 | | | | | | | | (SEQ ID NO. 200) |
| miR-C18 | UAGCAGCACAGAAAUAUUGGC | 2 | | 1 | 1 | | | | | | | (SEQ ID NO. 201) |
| miR-C19 | UAGGUAGUUUCAUGUUGUUGG | | | | | | | | 1 | | | (SEQ ID NO. 202) |
| miR-C20 | UUCACCACCUUCUCCACCCAGC | | | | | | | | 1 | 1 | | (SEQ ID NO. 203) |
| miR-C21 | GGUCCAGAGGGGAGAUAGG | | | | | | | | 1 | | | (SEQ ID NO. 204) |
| miR-C22 | CCCAGUGUUCAGACUACCUGUU | | | | | | | | 1 | | | (SEQ ID NO. 205) |
| miR-C23 | UAAUACUGCCUGGUAAUGAUGAC | 2 | | | 1 | | | | | | | (SEQ ID NO. 206) |
| miR-C24 | UACUCAGUAAGGCAUUGUUCU | | | | 1 | | | | | | | (SEQ ID NO. 207) |
| miR-C25 | AGAGGUAUAGCGCAUGGGAAGA | | | | 1 | | | | | | | (SEQ ID NO. 208) |
| miR-C26 | UGAAAUGUUUAGGACCACUAG | | | | 1 | | | | | | | (SEQ ID NO. 209) |
| miR-C27 | UUCCCUUUGUCAUCCUAUGCCUG | | | | | | | 1 | | | | (SEQ ID NO. 210) |
| miR-C28 | UCCUUCAUUCCACCGGAGUCUG | | | 1 | | | | | | | | (SEQ ID NO. 211) |
| miR-C29 | GUGAAAUGUUUAGGACCACUAGA | | | 2 | | | | | | | | (SEQ ID NO. 212) |
| miR-C30 | UGGAAUGUAAGGAAGUGUGUGG | | | 2 | | | | | | | | (SEQ ID NO. 213) |
| miR-C31 | UACAGUAGUCUGCACAUUGGUU | | | 1 | | | | | | | | (SEQ ID NO. 214) |
| miR-C32 | CCCUGUAGAACCGAAUUUGUGU | | | 1 | 1 | | | | | | | (SEQ ID NO. 215) |
| miR-C33 | AACCCGUAGAUCCGAACUUGUGAA | | | 1 | | | | | | | | (SEQ ID NO. 216) |
| miR-C34 | GCUUCUCCUGGCUCUCCUCCCUC | | | | | | | | 1 | | | (SEQ ID NO. 217) |

TABLE 5

*D. melanogaster* miRNA sequences and genomic location. The sequences given represent the most abundant, and typically longest miRNA sequences identified by cloning. It was frequently observed that miRNAs vary in length by one or two nucleotides at their 3'-terminus. From 222 short RNAs sequenced; 69 (31%) corresponded to miRNAs, 103 (46%) to already characterized functional RNAs (rRNA, 7SL RNA, tRNAs), 30 (14%) to transposon RNA fragments, and 20 (10%) sequences with no database entry. RNA sequences with a 5'-guanosine are likely to be underrepresented due to the cloning procedure (8). miRNA homologs found in other species are indicated. Chromosomal location (chr.) and GenBank accession numbers (acc. nb.) are indicated. No ESTs matching miR-1 to miR-14 were detectable by database searching.

| mIRNA | sequence (5' to 3') | chr., acc. nb. | remarks |
|---|---|---|---|
| miR-1 | UGGAAUGUAAAGAAGUAUGGAG (SEQ ID NO: 58) | 2L, AE003667 | homologs: *C. briggsae*, G20U, AC87074; *C.elegans* G20U, U97405; mouse, G20U, G22U, AC020867; human, chr. 20, G20U, G22U, AL449263; ESTs: zebrafish, G20U, G22U, BF157-601; cow, G20U, G22U, BE722-224; human, G20U, G22U, AI220268 |
| miR-2a | UAUCACAGCCAGCUUUGAUGAGC (SEQ ID NO: 59) | 2L, AE003663 | 2 precursor variants clustered with a copy of mir-2b |
| miR-2b | UAUCACAGCCAGCUUUGAGGAGC (SEQ ID NO: 60) | 2L, AE003620 2L, AE003663 | 2 precursor variants |
| miR-3 | UCACUGGGCAAAGUGUGUCUCA (SEQ ID NO: 61) | 2R, AE003795 | in cluster mir-3 to mir-6 |
| miR-4 | AUAAAGCUAGACAACCAUUGA (SEQ ID NO: 62) | 2R, AE003795 | in cluster mir-3 to mir-6 |
| miR-5 | AAAGGAACGAUCGUUGUGAUAUG (SEQ ID NO: 63) | 2R, AE003795 | in cluster mir-3 to mir-6 |
| miR-6 | UAUCACAGUGGCUGUUCUUUUU (SEQ ID NO: 64) | 2R, AE003795 | in cluster mir-3 to mir-6 with 3 variants |
| miR-7 | UGGAAGACUAGUGAUUUUGUUGU (SEQ ID NO: 65) | 2R, AE003791 | homologs: human, chr. 19 AC006537, EST BF373391; mouse chr. 17 AC026385, EST AA881786 |
| miR-8 | UAAUACUGUCAGGUAAAGAUGUC (SEQ ID NO: 66) | 2R, AE003805 | |
| miR-9 | UCUUUGGUUAUCUAGCUGUAUGA (SEQ ID NO: 67) | 3L, AE003516 | homologs: mouse, chr. 19, AF155142; human, chr. 5, AC026701, chr. 15, AC005316 |
| miR-10 | ACCCUGUAGAUCCGAAUUUGU (SEQ ID NO: 68) | AE001574 | homologs: mouse, chr 11, AC011194; human, chr. 17, AF287967 |
| miR-11 | CAUCACAGUCUGAGUUCUUGC (SEQ ID NO: 69) | 3R, AE003735 | intronic location |
| miR-12 | UGAGUAUUACAUCAGGUACUGGU (SEQ ID NO: 70) | X, AE003499 | intronic location |
| miR-13a | UAUCACAGCCAUUUUGACGAGU (SEQ ID NO: 71) | 3R, AE003708 X; AE003446 | mir-13a clustered with mir-13b on chr. 3R |
| miR-13b | UAUCACAGCCAUUUUGAUGAGU (SEQ ID NO: 72) | 3R, AE003708 | mir-13a clustered with mir-13b on chr. 3R |
| miR-14 | UCAGUCUUUUUCUCUCUCCUA (SEQ ID NO: 73) | 2R, AE003833 | no signal by Northern analysis |

TABLE 6

Human miRNA sequences and genomic location. From 220 short RNAs sequenced, 100 (45%) corresponded to miRNAs, 53 (24%) to already characterized functional RNAs (rRNA, snRNAs, tRNAs), and 67 (30%) sequences with no database entry. For legend, see Table 1.

| miRNA | sequence (5' to 3') | chr. or EST, acc. nb. | remarks* |
|---|---|---|---|
| let-7a | UGAGGUAGUAGGUUGUAUAGUU (SEQ ID NO: 75) | 9, AC007924, 11, AP001359, 17, AC087784, 22, AL049853 | sequences of chr 9 and 17 identical and clustered with let-7f, homologs: *C. elegans*, AF274345; *C. briggsae*, AF210771, *D. melanogaster*, AE003659 |
| let-7b | UGAGGUAGUAGGUUGUGUGGUU (SEQ ID NO: 76) | 22, AL049853†, ESTs, AI382133, AW028822 | homologs: mouse, EST AI481799; rat, EST, BE120662 |
| let-7c | UGAGGUAGUAGGUUGUAUGGUU (SEQ ID NO: 77) | 21, AP001667 | Homologs: mouse, EST, AA575575 |
| let-7d | AGAGGUAGUAGGUUGCAUAGU (SEQ ID NO: 78) | 17, AC057784, 9, AC007924 | identical precursor sequences |
| let-7e | UGAGGUAGGAGGUUGUAUAGU (SEQ ID NO: 79) | 19, AC018755 | |
| let-7f | UGAGGUAGUAGAUUGUAUAGUU (SEQ ID NO: 80) | 9, AC007924, 17, AC087784, X, AL592046 | sequences of chr 9 and 17 identical and clustered with let-7a |
| miR-15 | UAGCAGCACAUAAUGGUUUGUG (SEQ ID NO: 81) | 13, AC069475 | in cluster with mir-16 homolog |
| miR-16 | UAGCAGCACGUAAAUAUUGGCG (SEQ ID NO: 82) | 13, AC069475 | in cluster with mir-15 homolog |
| miR-17 | ACUGCAGUGAAGGCACUUGU (SEQ ID NO: 83) | 13, AL138714 | in cluster with mir-17 to mir-20 |
| miR-18 | UAAGGUGCAUCUAGUGCAGAUA (SEQ ID NO: 84) | 13, AL138714 | in cluster with mir-17 to mir-20 |
| miR-19a | UGUGCAAAUCUAUGCAAAACUGA (SEQ ID NO: 85) | 13, AL138714 | in cluster with mir-17 to mir-20 |
| miR-19b | UGUGCAAAUCCAUGCAAAACUGA (SEQ ID NO: 86) | 13, AL138714, X, AC002407 | in cluster with mir-17 to mir-20 |
| miR-20 | UAAAGUGCUUAUAGUGCAGGUA (SEQ ID NO: 87) | 13, AL138714 | in cluster with mir-17 to mir-20 |
| miR-21 | UAGCUUAUCAGACUGAUGUUGA (SEQ ID NO: 88) | 17, AC004686, EST, BF326048 | homologs: mouse, EST, AA209594 |
| miR-22 | AAGCUGCCAGUUGAAGAACUGU (SEQ ID NO: 89) | ESTs, AW961681†, AA456477, AI752503, BF030303, HS1242049 | human ESTs highly similar; homologs: mouse, ESTs, e.g. AA823029; rat, ESTs, e.g. BF543690 |
| miR-23 | AUCACAUUGCCAGGGAUUUCC (SEQ ID NO: 90) | 19, AC020916 | homologs: mouse, EST, AW124037; rat, EST, BF402515 |
| miR-24 | UGGCUCAGUUCAGCAGGAACAG (SEQ ID NO: 91) | 9, AF043896, 19, AC020916 | homologs: mouse, ESTs, AA111466, AI286629; pig, EST, BE030976 |
| miR-25 | CAUUGCACUUGUCUCGGUCUGA (SEQ ID NO: 92) | 7, AC073842, EST, BE077684 | human chr 7 and EST identical; highly similar precursors in mouse ESTs (e.g. AI595464); fish precursor different STS: G46757 |
| miR-26a | UUCAAGUAAUCCAGGAUAGGCU (SEQ ID NO: 93) | 3, AP000497 | |
| miR-26b | UUCAAGUAAUUCAGGAUAGGUU (SEQ ID NO: 94) | 2, AC021016 | |

TABLE 6-continued

Human miRNA sequences and genomic location. From 220 short RNAs sequenced, 100 (45%) corresponded to miRNAs, 53 (24%) to already characterized functional RNAs (rRNA, snRNAs, tRNAs), and 67 (30%) sequences with no database entry. For legend, see Table 1.

| miRNA | sequence (5' to 3') | chr. or EST, acc. nb. | remarks* |
|---|---|---|---|
| miR-27 | UUCACAGUGGCUAAGUUCCGCU (SEQ ID NO: 95) | 19, AC20916 | U22C mutation in human genomic sequence |
| miR-28 | AAGGAGCUCACAGUCUAUUGAG (SEQ ID NO: 96) | 3, AC063932 | |
| miR-29 | CUAGCACCAUCUGAAAUCGGUU (SEQ ID NO: 97) | 7, AF017104 | |
| miR-30 | CUUUCAGUCGGAUGUUUGCAGC (SEQ ID NO: 98) | 6, AL035467 | |
| miR-31 | GGCAAGAUGCUGGCAUAGCUG (SEQ ID NO: 99) | 9, AL353732 | |
| miR-32 | UAUUGCACAUUACUAAGUUGC (SEQ ID NO: 100) | 9, AL354797 | not detected by Northern blotting |
| miR-33 | GUGCAUUGUAGUUGCAUUG (SEQ ID NO: 101) | 22, Z99716 | not detected by Northern blotting |

*If several ESTs were retrieved for one organism in the database, only those with different precursor sequences are listed.
†precursor structure shown in FIG. 4.

SEQUENCE LISTING

<160> NUMBER OF SEQ ID NOS: 562

<210> SEQ ID NO 1
<211> LENGTH: 29
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary let-7a

<400> SEQUENCE: 1
tactatacaa cctactacct caatttgcc                                       29

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary let-7d

<400> SEQUENCE: 2
actatgcaac ctactacctc t                                               21

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary let-7e

<400> SEQUENCE: 3
actatacaac ctcctacctc a                                               21

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide probe with significant homology
      to D. melanogaster Val-tRNA

<400> SEQUENCE: 4
tggtgtttcc gcccgggaa                                                  19

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-1

<400> SEQUENCE: 5
tggaatgtaa agaagtatgg ag                                              22

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-2b

<400> SEQUENCE: 6
gctcctcaaa gctggctgtg ata                                             23

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-3

<400> SEQUENCE: 7
tgagacacac tttgcccagt ga                                              22

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-4

<400> SEQUENCE: 8
tcaatggttg tctagcttta t                                               21

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide probe with significant homology -continued to D. melanogaster, HeLa cell, mouse kidney, adult zebrafish and
frog ovary miR-5

<400> SEQUENCE: 9
catatcacaa cgatcgttcc ttt                                          23

<210> SEQ ID NO 10
<211> LENGTH: 22
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-6

<400> SEQUENCE: 10
aaaaagaaca gccactgtga ta                                           22

<210> SEQ ID NO 11
<211> LENGTH: 23
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-7

<400> SEQUENCE: 11
tggaagacta gtgattttgt tgt                                          23

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-8

<400> SEQUENCE: 12
gacatcttta cctgacagta tta                                          23

<210> SEQ ID NO 13
<211> LENGTH: 23
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-9

<400> SEQUENCE: 13
tcatacagct agataaccaa aga                                          23

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-10

<400> SEQUENCE: 14
acaaattcgg atctacaggg t                                            21

<210> SEQ ID NO 15

-continued

```
<210> SEQ ID NO 15
<211> LENGTH: 21
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-11

<400> SEQUENCE: 15
gcaagaactc agactgtgat g                                              21

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-12

<400> SEQUENCE: 16
accagtacct gatgtaatac tca                                            23

<210> SEQ ID NO 17
<211> LENGTH: 22
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-13a

<400> SEQUENCE: 17
actcgtcaaa atggctgtga ta                                             22

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-14

<400> SEQUENCE: 18
taggagagag aaaaagactg a                                              21

<210> SEQ ID NO 19
<211> LENGTH: 21
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-15

<400> SEQUENCE: 19
tagcagcaca taatggtttg t                                              21

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-16

<400> SEQUENCE: 20
```

```
gccaatattt acgtgctgct a                                              21

<210> SEQ ID NO 21
<211> LENGTH: 22
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-17

<400> SEQUENCE: 21
tacaagtgcc ttcactgcag ta                                             22

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-18

<400> SEQUENCE: 22
tatctgcact agatgcacct ta                                             22

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-19a

<400> SEQUENCE: 23
tcagttttgc atagatttgc aca                                            23

<210> SEQ ID NO 24
<211> LENGTH: 22
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-20

<400> SEQUENCE: 24
tacctgcact ataagcactt ta                                             22

<210> SEQ ID NO 25
<211> LENGTH: 22
<212> TYPE: DNA
<213> ORGANISM: Artificial Sequence
<220> FEATURE:
<223> OTHER INFORMATION: Oligonucleotide probe with significant homology
      to D. melanogaster, HeLa cell, mouse kidney, adult zebrafish and
      frog ovary miR-21

<400> SEQUENCE: 25
tcaacatcag tctgataagc ta                                             22

<210> SEQ ID NO 26
<211> LENGTH: 22
<212> TYPE: DNA
<213> ORGANISM: Artificial Sequence
<220> FEATURE:
```

-continued

<223> OTHER INFORMATION: Oligonucleotide probe with significant homology
to D. melanogaster, HeLa cell, mouse kidney, adult zebrafish and
frog ovary miR-22

<400> SEQUENCE: 26
acagttcttc aactggcagc tt                                              22

<210> SEQ ID NO 27
<211> LENGTH: 21
<212> TYPE: DNA
<213> ORGANISM: Artificial Sequence
<220> FEATURE:
<223> OTHER INFORMATION: Oligonucleotide probe with significant homology
to D. melanogaster, HeLa cell, mouse kidney, adult zebrafish and
frog ovary miR-23

<400> SEQUENCE: 27
ggaaatccct ggcaatgtga t                                               21

<210> SEQ ID NO 28
<211> LENGTH: 22
<212> TYPE: DNA
<213> ORGANISM: Artificial Sequence
<220> FEATURE:
<223> OTHER INFORMATION: Oligonucleotide probe with significant homology
to D. melanogaster, HeLa cell, mouse kidney, adult zebrafish and
frog ovary miR-24

<400> SEQUENCE: 28
ctgttcctgc tgaactgagc ca                                              22

<210> SEQ ID NO 29
<211> LENGTH: 22
<212> TYPE: DNA
<213> ORGANISM: Artificial Sequence
<220> FEATURE:
<223> OTHER INFORMATION: Oligonucleotide probe with significant homology
to D. melanogaster, HeLa cell, mouse kidney, adult zebrafish and
frog ovary miR-25

<400> SEQUENCE: 29
tcagaccgag acaagtgcaa tg                                              22

<210> SEQ ID NO 30
<211> LENGTH: 22
<212> TYPE: DNA
<213> ORGANISM: Artificial Sequence
<220> FEATURE:
<223> OTHER INFORMATION: Oligonucleotide probe with significant homology
to D. melanogaster, HeLa cell, mouse kidney, adult zebrafish and
frog ovary miR-26a

<400> SEQUENCE: 30
agcctatcct ggattacttg aa                                              22

<210> SEQ ID NO 31
<211> LENGTH: 22
<212> TYPE: DNA
<213> ORGANISM: Artificial Sequence
<220> FEATURE:
<223> OTHER INFORMATION: Oligonucleotide probe with significant homology
to D. melanogaster, HeLa cell, mouse kidney, adult zebrafish and
frog ovary miR-27

<400> SEQUENCE: 31
agcggaactt agccactgtg aa                                              22

<210> SEQ ID NO 32
<211> LENGTH: 22
<212> TYPE: DNA
<213> ORGANISM: Artificial Sequence
<220> FEATURE:
<223> OTHER INFORMATION: Oligonucleotide probe with significant homology
    to D. melanogaster, HeLa cell, mouse kidney, adult zebrafish and
    frog ovary miR-28

<400> SEQUENCE: 32
ctcaatagac tgtgagctcc tt                                              22

<210> SEQ ID NO 33
<211> LENGTH: 22
<212> TYPE: DNA
<213> ORGANISM: Artificial Sequence
<220> FEATURE:
<223> OTHER INFORMATION: Oligonucleotide probe with significant homology
    to D. melanogaster, HeLa cell, mouse kidney, adult zebrafish and
    frog ovary miR-29

<400> SEQUENCE: 33
aaccgatttc agatggtgct ag                                              22

<210> SEQ ID NO 34
<211> LENGTH: 22
<212> TYPE: DNA
<213> ORGANISM: Artificial Sequence
<220> FEATURE:
<223> OTHER INFORMATION: Oligonucleotide probe with significant homology
    to D. melanogaster, HeLa cell, mouse kidney, adult zebrafish and
    frog ovary miR-30

<400> SEQUENCE: 34
gctgcaaaca tccgactgaa ag                                              22

<210> SEQ ID NO 35
<211> LENGTH: 22
<212> TYPE: DNA
<213> ORGANISM: Artificial Sequence
<220> FEATURE:
<223> OTHER INFORMATION: Oligonucleotide probe with significant homology
    to D. melanogaster, HeLa cell, mouse kidney, adult zebrafish and
    frog ovary miR-31

<400> SEQUENCE: 35
cagctatgcc agcatcttgc ct                                              22

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide probe with significant homology
    to D. melanogaster, HeLa cell, mouse kidney, adult zebrafish and
    frog ovary miR-32

<400> SEQUENCE: 36
gcaacttagt aatgtgcaat a                                               21

<210> SEQ ID NO 37
<211> LENGTH: 22
<212> TYPE: DNA
<213> ORGANISM: Artificial Sequence
<220> FEATURE:
<223> OTHER INFORMATION: Oligonucleotide probe with significant homology
    to D. melanogaster, HeLa cell, mouse kidney, adult zebrafish and
    frog ovary miR-33

```
<400> SEQUENCE: 37
tgcaatgcaa ctacaatgca cc                                          22

<210> SEQ ID NO 38
<211> LENGTH: 22
<212> TYPE: DNA
<213> ORGANISM: Artificial Sequence
<220> FEATURE:
<223> OTHER INFORMATION: Oligonucleotide probe with significant homology
      to mouse and HeLa cell miR-1a

<400> SEQUENCE: 38
ctccatactt ctttacattc ca                                          22

<210> SEQ ID NO 39
<211> LENGTH: 21
<212> TYPE: DNA
<213> ORGANISM: Artificial Sequence
<220> FEATURE:
<223> OTHER INFORMATION: Oligonucleotide probe with significant homology
      to mouse and HeLa cell miR-30b

<400> SEQUENCE: 39
gctgagtgta ggatgtttac a                                           21

<210> SEQ ID NO 40
<211> LENGTH: 23
<212> TYPE: DNA
<213> ORGANISM: Artificial Sequence
<220> FEATURE:
<223> OTHER INFORMATION: Oligonucleotide probe with significant homology
      to mouse and HeLa cell miR-30a-s

<400> SEQUENCE: 40
gcttccagtc gaggatgttt aca                                         23

<210> SEQ ID NO 41
<211> LENGTH: 22
<212> TYPE: DNA
<213> ORGANISM: Artificial Sequence
<220> FEATURE:
<223> OTHER INFORMATION: Oligonucleotide probe with significant homology
      to mouse and HeLa cell miR-99b

<400> SEQUENCE: 41
cgcaaggtcg gttctacggg tg                                          22

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide probe with significant homology
      to mouse and HeLa cell miR-101

<400> SEQUENCE: 42
tcagttatca cagtactgta                                             20

<210> SEQ ID NO 43
<211> LENGTH: 23
<212> TYPE: DNA
<213> ORGANISM: Artificial Sequence
<220> FEATURE:
<223> OTHER INFORMATION: Oligonucleotide probe with significant homology
      to mouse and HeLa cell miR-122a

<400> SEQUENCE: 43
```

-continued acaaacacca ttgtcacact cca                                          23

<210> SEQ ID NO 44
<211> LENGTH: 21
<212> TYPE: DNA
<213> ORGANISM: Artificial Sequence
<220> FEATURE:
<223> OTHER INFORMATION: Oligonucleotide probe with significant homology
      to mouse and HeLa cell miR-124a

<400> SEQUENCE: 44
tggcattcac cgcgtgcctt a                                            21

<210> SEQ ID NO 45
<211> LENGTH: 23
<212> TYPE: DNA
<213> ORGANISM: Artificial Sequence
<220> FEATURE:
<223> OTHER INFORMATION: Oligonucleotide probe with significant homology
      to mouse and HeLa cell miR-125a

<400> SEQUENCE: 45
cacaggttaa agggtctcag gga                                          23

<210> SEQ ID NO 46
<211> LENGTH: 22
<212> TYPE: DNA
<213> ORGANISM: Artificial Sequence
<220> FEATURE:
<223> OTHER INFORMATION: Oligonucleotide probe with significant homology
      to mouse and HeLa cell miR-125b

<400> SEQUENCE: 46
tcacaagtta gggtctcagg ga                                           22

<210> SEQ ID NO 47
<211> LENGTH: 22
<212> TYPE: DNA
<213> ORGANISM: Artificial Sequence
<220> FEATURE:
<223> OTHER INFORMATION: Oligonucleotide probe with significant homology
      to mouse and HeLa cell miR-127

<400> SEQUENCE: 47
agccaagctc agacggatcc ga                                           22

<210> SEQ ID NO 48
<211> LENGTH: 22
<212> TYPE: DNA
<213> ORGANISM: Artificial Sequence
<220> FEATURE:
<223> OTHER INFORMATION: Oligonucleotide probe with significant homology
      to mouse and HeLa cell miR-128

<400> SEQUENCE: 48
aaaagagacc ggttcactct ga                                           22

<210> SEQ ID NO 49
<211> LENGTH: 21
<212> TYPE: DNA
<213> ORGANISM: Artificial Sequence
<220> FEATURE:
<223> OTHER INFORMATION: Oligonucleotide probe with significant homology
      to mouse and HeLa cell miR-129

<400> SEQUENCE: 49

```
gcaagcccag accgaaaaaa g                                              21

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide probe with significant homology
      to mouse and HeLa cell miR-130

<400> SEQUENCE: 50
gcccttttaa cattgcactc                                                20

<210> SEQ ID NO 51
<211> LENGTH: 21
<212> TYPE: DNA
<213> ORGANISM: Artificial Sequence
<220> FEATURE:
<223> OTHER INFORMATION: Oligonucleotide probe with significant homology
      to mouse and HeLa cell miR-131

<400> SEQUENCE: 51
actttcggtt atctagcttt a                                              21

<210> SEQ ID NO 52
<211> LENGTH: 23
<212> TYPE: DNA
<213> ORGANISM: Artificial Sequence
<220> FEATURE:
<223> OTHER INFORMATION: Oligonucleotide probe with significant homology
      to mouse and HeLa cell miR-132

<400> SEQUENCE: 52
acgaccatgg ctgtagactg tta                                            23

<210> SEQ ID NO 53
<211> LENGTH: 22
<212> TYPE: DNA
<213> ORGANISM: Artificial Sequence
<220> FEATURE:
<223> OTHER INFORMATION: Oligonucleotide probe with significant homology
      to mouse and HeLa cell miR-143

<400> SEQUENCE: 53
tgagctacag tgcttcatct ca                                             22

<210> SEQ ID NO 54
<211> LENGTH: 18
<212> TYPE: DNA
<213> ORGANISM: Artificial Sequence
<220> FEATURE:
<223> OTHER INFORMATION: combined DNA/ RNA molecule - 3' adapter
      oligonucleotide for ligation to short mouse RNAs
<220> FEATURE:
<221> NAME/KEY: misc_feature
<222> LOCATION: (1)..(1)
<223> OTHER INFORMATION: phosphorylated
<220> FEATURE:
<221> NAME/KEY: misc_feature
<222> LOCATION: (1)..(3)
<223> OTHER INFORMATION: RNA
<220> FEATURE:
<221> NAME/KEY: misc_feature
<222> LOCATION: (4)..(18)
<223> OTHER INFORMATION: DNA
<220> FEATURE:
<221> NAME/KEY: misc_feature
<222> LOCATION: (18)..(18)
<223> OTHER INFORMATION: 3'-amino modifier C-7
```

```
<400> SEQUENCE: 54
uuuaaccgcg aattccag                                                   18

<210> SEQ ID NO 55
<211> LENGTH: 18
<212> TYPE: DNA
<213> ORGANISM: Artificial Sequence
<220> FEATURE:
<223> OTHER INFORMATION: combined DNA/ RNA molecule - 5' adapter
      oligonucleotide for ligation to short mouse RNAs
<220> FEATURE:
<221> NAME/KEY: misc_feature
<222> LOCATION: (1)..(15)
<223> OTHER INFORMATION: DNA
<220> FEATURE:
<221> NAME/KEY: misc_feature
<222> LOCATION: (16)..(18)
<223> OTHER INFORMATION: RNA

<400> SEQUENCE: 55
acggaattcc tcactaaa                                                   18

<210> SEQ ID NO 56
<211> LENGTH: 30
<212> TYPE: DNA
<213> ORGANISM: Artificial Sequence
<220> FEATURE:
<223> OTHER INFORMATION: Oligonucleotide primer with homology to
      3'-adapter oligonucleotide (SEQ ID NO: 54) and short mouse RNAs

<400> SEQUENCE: 56
gactagcttg gtgccgaatt cgcggttaaa                                      30

<210> SEQ ID NO 57
<211> LENGTH: 24
<212> TYPE: DNA
<213> ORGANISM: Artificial Sequence
<220> FEATURE:
<223> OTHER INFORMATION: Oligonucleotide primer with homology to
      5'-adapter oligonucleotide (SEQ ID NO: 55) and short mouse RNAs

<400> SEQUENCE: 57
cagccaacgg aattcctcac taaa                                            24

<210> SEQ ID NO 58
<211> LENGTH: 22
<212> TYPE: RNA
<213> ORGANISM: Drosophila melanogaster

<400> SEQUENCE: 58
uggaauguaa agaaguaugg ag                                              22

<210> SEQ ID NO 59
<211> LENGTH: 23
<212> TYPE: RNA
<213> ORGANISM: Drosophila melanogaster

<400> SEQUENCE: 59
uaucacagcc agcuuugaug agc                                             23

<210> SEQ ID NO 60
<211> LENGTH: 23
<212> TYPE: RNA
<213> ORGANISM: Drosophila melanogaster

<400> SEQUENCE: 60
```

-continued uaucacagcc agcuuugagg agc                                    23

<210> SEQ ID NO 61
<211> LENGTH: 22
<212> TYPE: RNA
<213> ORGANISM: Drosophila melanogaster

<400> SEQUENCE: 61
ucacugggca aagugugucu ca                                     22

<210> SEQ ID NO 62
<211> LENGTH: 21
<212> TYPE: RNA
<213> ORGANISM: Drosophila melanogaster

<400> SEQUENCE: 62
auaaagcuag acaaccauug a                                      21

<210> SEQ ID NO 63
<211> LENGTH: 23
<212> TYPE: RNA
<213> ORGANISM: Drosophila melanogaster

<400> SEQUENCE: 63
aaaggaacga ucguugugau aug                                    23

<210> SEQ ID NO 64
<211> LENGTH: 22
<212> TYPE: RNA
<213> ORGANISM: Drosophila melanogaster

<400> SEQUENCE: 64
uaucacagug gcuguucuuu uu                                     22

<210> SEQ ID NO 65
<211> LENGTH: 23
<212> TYPE: RNA
<213> ORGANISM: Drosophila melanogaster

<400> SEQUENCE: 65
uggaagacua gugauuuugu ugu                                    23

<210> SEQ ID NO 66
<211> LENGTH: 23
<212> TYPE: RNA
<213> ORGANISM: Drosophila melanogaster

<400> SEQUENCE: 66
uaauacuguc agguaaagau guc                                    23

<210> SEQ ID NO 67
<211> LENGTH: 23
<212> TYPE: RNA
<213> ORGANISM: Drosophila melanogaster

<400> SEQUENCE: 67
ucuuugguua ucuagcugua uga                                    23

<210> SEQ ID NO 68
<211> LENGTH: 21
<212> TYPE: RNA
<213> ORGANISM: Drosophila melanogaster

<400> SEQUENCE: 68

-continued acccuguaga uccgaauuug u                                         21

<210> SEQ ID NO 69
<211> LENGTH: 21
<212> TYPE: RNA
<213> ORGANISM: Drosophila melanogaster

<400> SEQUENCE: 69
caucacaguc ugaguucuug c                                         21

<210> SEQ ID NO 70
<211> LENGTH: 23
<212> TYPE: RNA
<213> ORGANISM: Drosophila melanogaster

<400> SEQUENCE: 70
ugaguauuac aucagguacu ggu                                       23

<210> SEQ ID NO 71
<211> LENGTH: 22
<212> TYPE: RNA
<213> ORGANISM: Drosophila melanogaster

<400> SEQUENCE: 71
uaucacagcc auuuugacga gu                                        22

<210> SEQ ID NO 72
<211> LENGTH: 22
<212> TYPE: RNA
<213> ORGANISM: Drosophila melanogaster

<400> SEQUENCE: 72
uaucacagcc auuuugauga gu                                        22

<210> SEQ ID NO 73
<211> LENGTH: 21
<212> TYPE: RNA
<213> ORGANISM: Drosophila melanogaster

<400> SEQUENCE: 73
ucagucuuuu ucucucuccu a                                         21

<210> SEQ ID NO 74
<211> LENGTH: 22
<212> TYPE: RNA
<213> ORGANISM: Drosophila melanogaster

<400> SEQUENCE: 74
ugagguagua gguuguauag uu                                        22

<210> SEQ ID NO 75
<211> LENGTH: 22
<212> TYPE: RNA
<213> ORGANISM: Homo sapiens

<400> SEQUENCE: 75
ugagguagua gguuguauag uu                                        22

<210> SEQ ID NO 76
<211> LENGTH: 22
<212> TYPE: RNA
<213> ORGANISM: Homo sapiens

```
<400> SEQUENCE: 76
ugagguagua gguugugugg uu                                              22

<210> SEQ ID NO 77
<211> LENGTH: 22
<212> TYPE: RNA
<213> ORGANISM: Homo sapiens

<400> SEQUENCE: 77
ugagguagua gguuguaugg uu                                              22

<210> SEQ ID NO 78
<211> LENGTH: 21
<212> TYPE: RNA
<213> ORGANISM: Homo sapiens

<400> SEQUENCE: 78
agagguagua gguugcauag u                                               21

<210> SEQ ID NO 79
<211> LENGTH: 21
<212> TYPE: RNA
<213> ORGANISM: Homo sapiens

<400> SEQUENCE: 79
ugagguagga gguuguauag u                                               21

<210> SEQ ID NO 80
<211> LENGTH: 22
<212> TYPE: RNA
<213> ORGANISM: Homo sapiens

<400> SEQUENCE: 80
ugagguagua gauuguauag uu                                              22

<210> SEQ ID NO 81
<211> LENGTH: 22
<212> TYPE: RNA
<213> ORGANISM: Homo sapiens

<400> SEQUENCE: 81
uagcagcaca uaaugguuug ug                                              22

<210> SEQ ID NO 82
<211> LENGTH: 22
<212> TYPE: RNA
<213> ORGANISM: Homo sapiens

<400> SEQUENCE: 82
uagcagcacg uaaauauugg cg                                              22

<210> SEQ ID NO 83
<211> LENGTH: 20
<212> TYPE: RNA
<213> ORGANISM: Homo sapiens

<400> SEQUENCE: 83
acugcaguga aggcacuugu                                                 20

<210> SEQ ID NO 84
<211> LENGTH: 22
<212> TYPE: RNA
<213> ORGANISM: Homo sapiens
```

```
<400> SEQUENCE: 84
uaaggugcau cuagugcaga ua                                              22

<210> SEQ ID NO 85
<211> LENGTH: 23
<212> TYPE: RNA
<213> ORGANISM: Homo sapiens

<400> SEQUENCE: 85
ugugcaaauc uaugcaaaac uga                                             23

<210> SEQ ID NO 86
<211> LENGTH: 23
<212> TYPE: RNA
<213> ORGANISM: Homo sapiens

<400> SEQUENCE: 86
ugugcaaauc caugcaaaac uga                                             23

<210> SEQ ID NO 87
<211> LENGTH: 22
<212> TYPE: RNA
<213> ORGANISM: Homo sapiens

<400> SEQUENCE: 87
uaaagugcuu auagugcagg ua                                              22

<210> SEQ ID NO 88
<211> LENGTH: 22
<212> TYPE: RNA
<213> ORGANISM: Homo sapiens

<400> SEQUENCE: 88
uagcuuauca gacugauguu ga                                              22

<210> SEQ ID NO 89
<211> LENGTH: 22
<212> TYPE: RNA
<213> ORGANISM: Homo sapiens

<400> SEQUENCE: 89
aagcugccag uugaagaacu gu                                              22

<210> SEQ ID NO 90
<211> LENGTH: 21
<212> TYPE: RNA
<213> ORGANISM: Homo sapiens

<400> SEQUENCE: 90
aucacauugc cagggauuuc c                                               21

<210> SEQ ID NO 91
<211> LENGTH: 22
<212> TYPE: RNA
<213> ORGANISM: Homo sapiens

<400> SEQUENCE: 91
uggcucaguu cagcaggaac ag                                              22

<210> SEQ ID NO 92
<211> LENGTH: 22
<212> TYPE: RNA
```

<213> ORGANISM: Homo sapiens

<400> SEQUENCE: 92
cauugcacuu gucucggucu ga    22

<210> SEQ ID NO 93
<211> LENGTH: 22
<212> TYPE: RNA
<213> ORGANISM: Homo sapiens

<400> SEQUENCE: 93
uucaaguaau ccaggauagg cu    22

<210> SEQ ID NO 94
<211> LENGTH: 22
<212> TYPE: RNA
<213> ORGANISM: Homo sapiens

<400> SEQUENCE: 94
uucaaguaau ucaggauagg uu    22

<210> SEQ ID NO 95
<211> LENGTH: 22
<212> TYPE: RNA
<213> ORGANISM: Homo sapiens

<400> SEQUENCE: 95
uucacagugg cuaaguuccg cu    22

<210> SEQ ID NO 96
<211> LENGTH: 22
<212> TYPE: RNA
<213> ORGANISM: Homo sapiens

<400> SEQUENCE: 96
aaggagcuca cagucuauug ag    22

<210> SEQ ID NO 97
<211> LENGTH: 22
<212> TYPE: RNA
<213> ORGANISM: Homo sapiens

<400> SEQUENCE: 97
cuagcaccau cugaaaucgg uu    22

<210> SEQ ID NO 98
<211> LENGTH: 22
<212> TYPE: RNA
<213> ORGANISM: Homo sapiens

<400> SEQUENCE: 98
cuuucagucg gauguuugca gc    22

<210> SEQ ID NO 99
<211> LENGTH: 21
<212> TYPE: RNA
<213> ORGANISM: Homo sapiens

<400> SEQUENCE: 99
ggcaagaugc uggcauagcu g    21

<210> SEQ ID NO 100
<211> LENGTH: 21

```
<212> TYPE: RNA
<213> ORGANISM: Homo sapiens

<400> SEQUENCE: 100
uauugcacau uacuaaguug c                                              21

<210> SEQ ID NO 101
<211> LENGTH: 19
<212> TYPE: RNA
<213> ORGANISM: Homo sapiens

<400> SEQUENCE: 101
gugcauugua guugcauug                                                 19

<210> SEQ ID NO 102
<211> LENGTH: 22
<212> TYPE: RNA
<213> ORGANISM: Homo sapiens

<400> SEQUENCE: 102
uggaauguaa agaaguaugg ag                                             22

<210> SEQ ID NO 103
<211> LENGTH: 23
<212> TYPE: RNA
<213> ORGANISM: Homo sapiens

<400> SEQUENCE: 103
uggaagacua gugauuuugu ugu                                            23

<210> SEQ ID NO 104
<211> LENGTH: 23
<212> TYPE: RNA
<213> ORGANISM: Homo sapiens

<400> SEQUENCE: 104
ucuuugguua ucuagcugua uga                                            23

<210> SEQ ID NO 105
<211> LENGTH: 21
<212> TYPE: RNA
<213> ORGANISM: Homo sapiens

<400> SEQUENCE: 105
acccuguaga uccgaauuug u                                              21

<210> SEQ ID NO 106
<211> LENGTH: 22
<212> TYPE: RNA
<213> ORGANISM: Mus musculus

<400> SEQUENCE: 106
ugagguagua gguuguauag uu                                             22

<210> SEQ ID NO 107
<211> LENGTH: 22
<212> TYPE: RNA
<213> ORGANISM: Mus musculus

<400> SEQUENCE: 107
ugagguagua gguugugugg uu                                             22

<210> SEQ ID NO 108
```

<210> SEQ ID NO 109
<211> LENGTH: 21
<212> TYPE: RNA
<213> ORGANISM: Mus musculus

<400> SEQUENCE: 108
ugagguagua gguuguaugg uu                                          22

<210> SEQ ID NO 109
<211> LENGTH: 21
<212> TYPE: RNA
<213> ORGANISM: Mus musculus

<400> SEQUENCE: 109
agagguagua gguugcauag u                                           21

<210> SEQ ID NO 110
<211> LENGTH: 21
<212> TYPE: RNA
<213> ORGANISM: Mus musculus

<400> SEQUENCE: 110
ugagguagga gguuguauag u                                           21

<210> SEQ ID NO 111
<211> LENGTH: 22
<212> TYPE: RNA
<213> ORGANISM: Mus musculus

<400> SEQUENCE: 111
ugagguagua gauuguauag uu                                          22

<210> SEQ ID NO 112
<211> LENGTH: 22
<212> TYPE: RNA
<213> ORGANISM: Mus musculus

<400> SEQUENCE: 112
ugagguagua guuuguacag ua                                          22

<210> SEQ ID NO 113
<211> LENGTH: 22
<212> TYPE: RNA
<213> ORGANISM: Mus musculus

<400> SEQUENCE: 113
ugagguagua guguguacag uu                                          22

<210> SEQ ID NO 114
<211> LENGTH: 19
<212> TYPE: RNA
<213> ORGANISM: Mus musculus

<400> SEQUENCE: 114
ugagguagua guuugugcu                                              19

<210> SEQ ID NO 115
<211> LENGTH: 22
<212> TYPE: RNA
<213> ORGANISM: Mus musculus

<400> SEQUENCE: 115
uggaauguaa agaaguaugu aa                                          22

```
<210> SEQ ID NO 116
<211> LENGTH: 22
<212> TYPE: RNA
<213> ORGANISM: Mus musculus

<400> SEQUENCE: 116
uggaauguaa agaaguaugu ac                                              22

<210> SEQ ID NO 117
<211> LENGTH: 23
<212> TYPE: RNA
<213> ORGANISM: Mus musculus

<400> SEQUENCE: 117
uggaauguaa agaaguaugu auu                                             23

<210> SEQ ID NO 118
<211> LENGTH: 23
<212> TYPE: RNA
<213> ORGANISM: Mus musculus

<400> SEQUENCE: 118
ucuuugguua ucuagcugua uga                                             23

<210> SEQ ID NO 119
<211> LENGTH: 22
<212> TYPE: RNA
<213> ORGANISM: Mus musculus

<400> SEQUENCE: 119
uagcagcaca uaaugguuug ug                                              22

<210> SEQ ID NO 120
<211> LENGTH: 22
<212> TYPE: RNA
<213> ORGANISM: Mus musculus

<400> SEQUENCE: 120
uagcagcaca ucaugguuua ca                                              22

<210> SEQ ID NO 121
<211> LENGTH: 22
<212> TYPE: RNA
<213> ORGANISM: Mus musculus

<400> SEQUENCE: 121
uagcagcacg uaaauauugg cg                                              22

<210> SEQ ID NO 122
<211> LENGTH: 22
<212> TYPE: RNA
<213> ORGANISM: Mus musculus

<400> SEQUENCE: 122
uaaggugcau cuagugcaga ua                                              22

<210> SEQ ID NO 123
<211> LENGTH: 23
<212> TYPE: RNA
<213> ORGANISM: Mus musculus

<400> SEQUENCE: 123
ugugcaaauc caugcaaaac uga                                             23
```

```
<210> SEQ ID NO 124
<211> LENGTH: 23
<212> TYPE: RNA
<213> ORGANISM: Mus musculus

<400> SEQUENCE: 124
uaaagugcuu auagugcagg uag                                            23

<210> SEQ ID NO 125
<211> LENGTH: 22
<212> TYPE: RNA
<213> ORGANISM: Mus musculus

<400> SEQUENCE: 125
uagcuuauca gacugauguu ga                                             22

<210> SEQ ID NO 126
<211> LENGTH: 22
<212> TYPE: RNA
<213> ORGANISM: Mus musculus

<400> SEQUENCE: 126
aagcugccag uugaagaacu gu                                             22

<210> SEQ ID NO 127
<211> LENGTH: 21
<212> TYPE: RNA
<213> ORGANISM: Mus musculus

<400> SEQUENCE: 127
aucacauugc cagggauuuc c                                              21

<210> SEQ ID NO 128
<211> LENGTH: 23
<212> TYPE: RNA
<213> ORGANISM: Mus musculus

<400> SEQUENCE: 128
aucacauugc cagggauuac cac                                            23

<210> SEQ ID NO 129
<211> LENGTH: 22
<212> TYPE: RNA
<213> ORGANISM: Mus musculus

<400> SEQUENCE: 129
uggcucaguu cagcaggaac ag                                             22

<210> SEQ ID NO 130
<211> LENGTH: 22
<212> TYPE: RNA
<213> ORGANISM: Mus musculus

<400> SEQUENCE: 130
uucaaguaau ccaggauagg cu                                             22

<210> SEQ ID NO 131
<211> LENGTH: 22
<212> TYPE: RNA
<213> ORGANISM: Mus musculus

<400> SEQUENCE: 131
uucaaguaau ucaggauagg uu                                             22
```

<210> SEQ ID NO 132
<211> LENGTH: 22
<212> TYPE: RNA
<213> ORGANISM: Mus musculus

<400> SEQUENCE: 132
uucacagugg cuaaguuccg cu                                          22

<210> SEQ ID NO 133
<211> LENGTH: 20
<212> TYPE: RNA
<213> ORGANISM: Mus musculus

<400> SEQUENCE: 133
uucacagugg cuaaguucug                                             20

<210> SEQ ID NO 134
<211> LENGTH: 22
<212> TYPE: RNA
<213> ORGANISM: Mus musculus

<400> SEQUENCE: 134
cuagcaccau cugaaaucgg uu                                          22

<210> SEQ ID NO 135
<211> LENGTH: 23
<212> TYPE: RNA
<213> ORGANISM: Mus musculus

<400> SEQUENCE: 135
uagcaccauu ugaaaucagu guu                                         23

<210> SEQ ID NO 136
<211> LENGTH: 22
<212> TYPE: RNA
<213> ORGANISM: Mus musculus

<400> SEQUENCE: 136
uagcaccauu ugaaaucggu ua                                          22

<210> SEQ ID NO 137
<211> LENGTH: 23
<212> TYPE: RNA
<213> ORGANISM: Mus musculus

<400> SEQUENCE: 137
uguaaacauc cucgacugga agc                                         23

<210> SEQ ID NO 138
<211> LENGTH: 22
<212> TYPE: RNA
<213> ORGANISM: Mus musculus

<400> SEQUENCE: 138
cuuucagucg gauguuugca gc                                          22

<210> SEQ ID NO 139
<211> LENGTH: 21
<212> TYPE: RNA
<213> ORGANISM: Mus musculus

<400> SEQUENCE: 139

-continued uguaaacauc cuacacucag c                                        21

<210> SEQ ID NO 140
<211> LENGTH: 23
<212> TYPE: RNA
<213> ORGANISM: Mus musculus

<400> SEQUENCE: 140
uguaaacauc cuacacucuc agc                                      23

<210> SEQ ID NO 141
<211> LENGTH: 22
<212> TYPE: RNA
<213> ORGANISM: Mus musculus

<400> SEQUENCE: 141
uguaaacauc cccgacugga ag                                       22

<210> SEQ ID NO 142
<211> LENGTH: 20
<212> TYPE: RNA
<213> ORGANISM: Mus musculus

<400> SEQUENCE: 142
acccguagau ccgaucuugu                                          20

<210> SEQ ID NO 143
<211> LENGTH: 22
<212> TYPE: RNA
<213> ORGANISM: Mus musculus

<400> SEQUENCE: 143
cacccguaga accgaccuug cg                                       22

<210> SEQ ID NO 144
<211> LENGTH: 20
<212> TYPE: RNA
<213> ORGANISM: Mus musculus

<400> SEQUENCE: 144
uacaguacug ugauaacuga                                          20

<210> SEQ ID NO 145
<211> LENGTH: 23
<212> TYPE: RNA
<213> ORGANISM: Mus musculus

<400> SEQUENCE: 145
uggaguguga caauggeguu ugu                                      23

<210> SEQ ID NO 146
<211> LENGTH: 23
<212> TYPE: RNA
<213> ORGANISM: Mus musculus

<400> SEQUENCE: 146
uggaguguga caauggeguu uga                                      23

<210> SEQ ID NO 147
<211> LENGTH: 22
<212> TYPE: RNA
<213> ORGANISM: Mus musculus

<400> SEQUENCE: 147

```
uggaguguga caauggug uu ug                                              22

<210> SEQ ID NO 148
<211> LENGTH: 21
<212> TYPE: RNA
<213> ORGANISM: Mus musculus

<400> SEQUENCE: 148
cauuauuacu uuugguacgc g                                                21

<210> SEQ ID NO 149
<211> LENGTH: 22
<212> TYPE: RNA
<213> ORGANISM: Mus musculus

<400> SEQUENCE: 149
uuaaggcacg cggugaaugc ca                                               22

<210> SEQ ID NO 150
<211> LENGTH: 21
<212> TYPE: RNA
<213> ORGANISM: Mus musculus

<400> SEQUENCE: 150
uuaaggcacg cgggugaaug c                                                21

<210> SEQ ID NO 151
<211> LENGTH: 23
<212> TYPE: RNA
<213> ORGANISM: Mus musculus

<400> SEQUENCE: 151
ucccugagac ccuuuaaccu gug                                              23

<210> SEQ ID NO 152
<211> LENGTH: 22
<212> TYPE: RNA
<213> ORGANISM: Mus musculus

<400> SEQUENCE: 152
ucccugagac ccuaacuugu ga                                               22

<210> SEQ ID NO 153
<211> LENGTH: 21
<212> TYPE: RNA
<213> ORGANISM: Mus musculus

<400> SEQUENCE: 153
ucguaccgug aguaauaaug c                                                21

<210> SEQ ID NO 154
<211> LENGTH: 22
<212> TYPE: RNA
<213> ORGANISM: Mus musculus

<400> SEQUENCE: 154
ucggauccgu cugagcuugg cu                                               22

<210> SEQ ID NO 155
<211> LENGTH: 22
<212> TYPE: RNA
<213> ORGANISM: Mus musculus
```

```
<400> SEQUENCE: 155
ucacagugaa ccggucucuu uu                                          22

<210> SEQ ID NO 156
<211> LENGTH: 21
<212> TYPE: RNA
<213> ORGANISM: Mus musculus

<400> SEQUENCE: 156 cuuuuucgg ucugggcuug c                                            21

<210> SEQ ID NO 157
<211> LENGTH: 20
<212> TYPE: RNA
<213> ORGANISM: Mus musculus

<400> SEQUENCE: 157
cagugcaaug uuaaaagggc                                             20

<210> SEQ ID NO 158
<211> LENGTH: 21
<212> TYPE: RNA
<213> ORGANISM: Mus musculus

<400> SEQUENCE: 158
uaaagcuaga uaaccgaaag u                                           21

<210> SEQ ID NO 159
<211> LENGTH: 23
<212> TYPE: RNA
<213> ORGANISM: Mus musculus

<400> SEQUENCE: 159
uaacagucua cagccauggu cgu                                         23

<210> SEQ ID NO 160
<211> LENGTH: 22
<212> TYPE: RNA
<213> ORGANISM: Mus musculus

<400> SEQUENCE: 160 uuggucccu ucaaccagcu gu                                           22

<210> SEQ ID NO 161
<211> LENGTH: 22
<212> TYPE: RNA
<213> ORGANISM: Mus musculus

<400> SEQUENCE: 161
ugugacuggu ugaccagagg ga                                          22

<210> SEQ ID NO 162
<211> LENGTH: 24
<212> TYPE: RNA
<213> ORGANISM: Mus musculus

<400> SEQUENCE: 162
uauggcuuuu uauuccuaug ugaa                                        24

<210> SEQ ID NO 163
<211> LENGTH: 23
<212> TYPE: RNA
<213> ORGANISM: Mus musculus
```

<400> SEQUENCE: 163
acuccauuug uuuugaugau gga								23

<210> SEQ ID NO 164
<211> LENGTH: 22
<212> TYPE: RNA
<213> ORGANISM: Mus musculus

<400> SEQUENCE: 164
uauugcuuaa gaauacgcgu ag								22

<210> SEQ ID NO 165
<211> LENGTH: 17
<212> TYPE: RNA
<213> ORGANISM: Mus musculus

<400> SEQUENCE: 165
agcugguguu gugaauc									17

<210> SEQ ID NO 166
<211> LENGTH: 18
<212> TYPE: RNA
<213> ORGANISM: Mus musculus

<400> SEQUENCE: 166
ucuacagugc acgugucu									18

<210> SEQ ID NO 167
<211> LENGTH: 21
<212> TYPE: RNA
<213> ORGANISM: Mus musculus

<400> SEQUENCE: 167
agugguuuua cccuauggua g									21

<210> SEQ ID NO 168
<211> LENGTH: 21
<212> TYPE: RNA
<213> ORGANISM: Mus musculus

<400> SEQUENCE: 168
aacacugucu gguaaagaug g									21

<210> SEQ ID NO 169
<211> LENGTH: 20
<212> TYPE: RNA
<213> ORGANISM: Mus musculus

<400> SEQUENCE: 169
cauaaaguag aaagcacuac									20

<210> SEQ ID NO 170
<211> LENGTH: 22
<212> TYPE: RNA
<213> ORGANISM: Mus musculus

<400> SEQUENCE: 170
uguaguguuu ccuacuuuau gg								22

<210> SEQ ID NO 171
<211> LENGTH: 22
<212> TYPE: RNA

<213> ORGANISM: Mus musculus

<400> SEQUENCE: 171
ugagaugaag cacuguagcu ca          22

<210> SEQ ID NO 172
<211> LENGTH: 22
<212> TYPE: RNA
<213> ORGANISM: Mus musculus

<400> SEQUENCE: 172
uacaguauag augauguacu ag          22

<210> SEQ ID NO 173
<211> LENGTH: 24
<212> TYPE: RNA
<213> ORGANISM: Mus musculus

<400> SEQUENCE: 173
guccaguuuu cccaggaauc ccuu         24

<210> SEQ ID NO 174
<211> LENGTH: 23
<212> TYPE: RNA
<213> ORGANISM: Mus musculus

<400> SEQUENCE: 174
ugagaacuga auuccauggg uuu         23

<210> SEQ ID NO 175
<211> LENGTH: 21
<212> TYPE: RNA
<213> ORGANISM: Mus musculus

<400> SEQUENCE: 175
guguguggaa augcuucugc c           21

<210> SEQ ID NO 176
<211> LENGTH: 22
<212> TYPE: RNA
<213> ORGANISM: Mus musculus

<400> SEQUENCE: 176
ucagugcacu acagaacuuu gu          22

<210> SEQ ID NO 177
<211> LENGTH: 22
<212> TYPE: RNA
<213> ORGANISM: Mus musculus

<400> SEQUENCE: 177
ucuggcuccg ugucuucacu cc          22

<210> SEQ ID NO 178
<211> LENGTH: 23
<212> TYPE: RNA
<213> ORGANISM: Mus musculus

<400> SEQUENCE: 178
ucucccaacc cuuguaccag ugu         23

<210> SEQ ID NO 179
<211> LENGTH: 22

```
<212> TYPE: RNA
<213> ORGANISM: Mus musculus

<400> SEQUENCE: 179
cuagacugag gcuccuugag gu                                              22

<210> SEQ ID NO 180
<211> LENGTH: 21
<212> TYPE: RNA
<213> ORGANISM: Mus musculus

<400> SEQUENCE: 180
ucagugcaug acagaacuug g                                               21

<210> SEQ ID NO 181
<211> LENGTH: 20
<212> TYPE: RNA
<213> ORGANISM: Mus musculus

<400> SEQUENCE: 181
uugcauaguc acaaaaguga                                                 20

<210> SEQ ID NO 182
<211> LENGTH: 22
<212> TYPE: RNA
<213> ORGANISM: Mus musculus

<400> SEQUENCE: 182
uagguuaucc guguugccuu cg                                              22

<210> SEQ ID NO 183
<211> LENGTH: 22
<212> TYPE: RNA
<213> ORGANISM: Mus musculus

<400> SEQUENCE: 183
uuaaugcuaa uugugauagg gg                                              22

<210> SEQ ID NO 184
<211> LENGTH: 23
<212> TYPE: RNA
<213> ORGANISM: Unknown
<220> FEATURE:
<223> OTHER INFORMATION: homo sapiens or mus musculus

<400> SEQUENCE: 184
aacauucaac gcugucggug agu                                             23

<210> SEQ ID NO 185
<211> LENGTH: 22
<212> TYPE: RNA
<213> ORGANISM: Unknown
<220> FEATURE:
<223> OTHER INFORMATION: homo sapiens or mus musculus

<400> SEQUENCE: 185
uuuggcaaug guagaacuca ca                                              22

<210> SEQ ID NO 186
<211> LENGTH: 23
<212> TYPE: RNA
<213> ORGANISM: Unknown
<220> FEATURE:
<223> OTHER INFORMATION: homo sapiens or mus musculus
```

```
<400> SEQUENCE: 186
uauggcacug guagaauuca cug                                    23

<210> SEQ ID NO 187
<211> LENGTH: 22
<212> TYPE: RNA
<213> ORGANISM: Unknown
<220> FEATURE:
<223> OTHER INFORMATION: homo sapiens or mus musculus

<400> SEQUENCE: 187
cuuuuugcgg ucugggcuug uu                                     22

<210> SEQ ID NO 188
<211> LENGTH: 22
<212> TYPE: RNA
<213> ORGANISM: Unknown
<220> FEATURE:
<223> OTHER INFORMATION: homo sapiens or mus musculus

<400> SEQUENCE: 188
uggacggaga acugauaagg gu                                     22

<210> SEQ ID NO 189
<211> LENGTH: 18
<212> TYPE: RNA
<213> ORGANISM: Unknown
<220> FEATURE:
<223> OTHER INFORMATION: homo sapiens or mus musculus

<400> SEQUENCE: 189
uggagagaaa ggcaguuc                                          18

<210> SEQ ID NO 190
<211> LENGTH: 23
<212> TYPE: RNA
<213> ORGANISM: Unknown
<220> FEATURE:
<223> OTHER INFORMATION: homo sapiens or mus musculus

<400> SEQUENCE: 190
caaagaauuc uccuuuuggg cuu                                    23

<210> SEQ ID NO 191
<211> LENGTH: 22
<212> TYPE: RNA
<213> ORGANISM: Unknown
<220> FEATURE:
<223> OTHER INFORMATION: homo sapiens or mus musculus

<400> SEQUENCE: 191
ucgugucuug uguugcagcc gg                                     22

<210> SEQ ID NO 192
<211> LENGTH: 21
<212> TYPE: RNA
<213> ORGANISM: Unknown
<220> FEATURE:
<223> OTHER INFORMATION: homo sapiens or mus musculus

<400> SEQUENCE: 192
uaacacuguc ugguaacgau g                                      21

<210> SEQ ID NO 193
<211> LENGTH: 22
```

```
<212> TYPE: RNA
<213> ORGANISM: Unknown
<220> FEATURE:
<223> OTHER INFORMATION: homo sapiens or mus musculus

<400> SEQUENCE: 193
caucccuugc augguggagg gu                                              22

<210> SEQ ID NO 194
<211> LENGTH: 23
<212> TYPE: RNA
<213> ORGANISM: Unknown
<220> FEATURE:
<223> OTHER INFORMATION: homo sapiens or mus musculus

<400> SEQUENCE: 194
gugccuacug agcugacauc agu                                             23

<210> SEQ ID NO 195
<211> LENGTH: 22
<212> TYPE: RNA
<213> ORGANISM: Unknown
<220> FEATURE:
<223> OTHER INFORMATION: homo sapiens or mus musculus

<400> SEQUENCE: 195
ugauauguuu gauauauuag gu                                              22

<210> SEQ ID NO 196
<211> LENGTH: 22
<212> TYPE: RNA
<213> ORGANISM: Unknown
<220> FEATURE:
<223> OTHER INFORMATION: homo sapiens or mus musculus

<400> SEQUENCE: 196
caacggaauc ccaaaagcag cu                                              22

<210> SEQ ID NO 197
<211> LENGTH: 18
<212> TYPE: RNA
<213> ORGANISM: Unknown
<220> FEATURE:
<223> OTHER INFORMATION: homo sapiens or mus musculus

<400> SEQUENCE: 197
cugaccuaug aauugaca                                                   18

<210> SEQ ID NO 198
<211> LENGTH: 22
<212> TYPE: RNA
<213> ORGANISM: Unknown
<220> FEATURE:
<223> OTHER INFORMATION: homo sapiens or mus musculus

<400> SEQUENCE: 198
uaccacaggg uagaaccacg ga                                              22

<210> SEQ ID NO 199
<211> LENGTH: 21
<212> TYPE: RNA
<213> ORGANISM: Unknown
<220> FEATURE:
<223> OTHER INFORMATION: homo sapiens or mus musculus

<400> SEQUENCE: 199
```

```
aacuggccua caaagucccca g                                            21

<210> SEQ ID NO 200
<211> LENGTH: 22
<212> TYPE: RNA
<213> ORGANISM: Unknown
<220> FEATURE:
<223> OTHER INFORMATION: homo sapiens or mus musculus

<400> SEQUENCE: 200
uguaacagca acuccaugug ga                                            22

<210> SEQ ID NO 201
<211> LENGTH: 21
<212> TYPE: RNA
<213> ORGANISM: Unknown
<220> FEATURE:
<223> OTHER INFORMATION: homo sapiens or mus musculus

<400> SEQUENCE: 201
uagcagcaca gaaauauugg c                                             21

<210> SEQ ID NO 202
<211> LENGTH: 21
<212> TYPE: RNA
<213> ORGANISM: Unknown
<220> FEATURE:
<223> OTHER INFORMATION: homo sapiens or mus musculus

<400> SEQUENCE: 202
uagguaguuu cauguuguug g                                             21

<210> SEQ ID NO 203
<211> LENGTH: 22
<212> TYPE: RNA
<213> ORGANISM: Unknown
<220> FEATURE:
<223> OTHER INFORMATION: homo sapiens or mus musculus

<400> SEQUENCE: 203
uucaccaccu ucuccaccca gc                                            22

<210> SEQ ID NO 204
<211> LENGTH: 19
<212> TYPE: RNA
<213> ORGANISM: Unknown
<220> FEATURE:
<223> OTHER INFORMATION: homo sapiens or mus musculus

<400> SEQUENCE: 204
gguccagagg ggagauagg                                                19

<210> SEQ ID NO 205
<211> LENGTH: 22
<212> TYPE: RNA
<213> ORGANISM: Unknown
<220> FEATURE:
<223> OTHER INFORMATION: homo sapiens or mus musculus

<400> SEQUENCE: 205
cccaguguuc agacuaccug uu                                            22

<210> SEQ ID NO 206
<211> LENGTH: 23
<212> TYPE: RNA
<213> ORGANISM: Unknown
```

```
<220> FEATURE:
<223> OTHER INFORMATION: homo sapiens or mus musculus

<400> SEQUENCE: 206
uaauacugcc ugguaaugau gac                                    23

<210> SEQ ID NO 207
<211> LENGTH: 21
<212> TYPE: RNA
<213> ORGANISM: Unknown
<220> FEATURE:
<223> OTHER INFORMATION: homo sapiens or mus musculus

<400> SEQUENCE: 207
uacucaguaa ggcauuguuc u                                      21

<210> SEQ ID NO 208
<211> LENGTH: 22
<212> TYPE: RNA
<213> ORGANISM: Unknown
<220> FEATURE:
<223> OTHER INFORMATION: homo sapiens or mus musculus

<400> SEQUENCE: 208
agagguauag cgcaugggaa ga                                     22

<210> SEQ ID NO 209
<211> LENGTH: 21
<212> TYPE: RNA
<213> ORGANISM: Unknown
<220> FEATURE:
<223> OTHER INFORMATION: homo sapiens or mus musculus

<400> SEQUENCE: 209
ugaaauguuu aggaccacua g                                      21

<210> SEQ ID NO 210
<211> LENGTH: 23
<212> TYPE: RNA
<213> ORGANISM: Unknown
<220> FEATURE:
<223> OTHER INFORMATION: homo sapiens or mus musculus

<400> SEQUENCE: 210
uucccuuugu cauccuaugc cug                                    23

<210> SEQ ID NO 211
<211> LENGTH: 22
<212> TYPE: RNA
<213> ORGANISM: Unknown
<220> FEATURE:
<223> OTHER INFORMATION: homo sapiens or mus musculus

<400> SEQUENCE: 211
uccuucauuc caccggaguc ug                                     22

<210> SEQ ID NO 212
<211> LENGTH: 23
<212> TYPE: RNA
<213> ORGANISM: Unknown
<220> FEATURE:
<223> OTHER INFORMATION: homo sapiens or mus musculus

<400> SEQUENCE: 212
gugaaauguu uaggaccacu aga                                    23
```

```
<210> SEQ ID NO 213
<211> LENGTH: 22
<212> TYPE: RNA
<213> ORGANISM: Unknown
<220> FEATURE:
<223> OTHER INFORMATION: homo sapiens or mus musculus

<400> SEQUENCE: 213
uggaauguaa ggaagugugu gg                                              22

<210> SEQ ID NO 214
<211> LENGTH: 22
<212> TYPE: RNA
<213> ORGANISM: Unknown
<220> FEATURE:
<223> OTHER INFORMATION: homo sapiens or mus musculus

<400> SEQUENCE: 214
uacaguaguc ugcacauugg uu                                              22

<210> SEQ ID NO 215
<211> LENGTH: 22
<212> TYPE: RNA
<213> ORGANISM: Unknown
<220> FEATURE:
<223> OTHER INFORMATION: homo sapiens or mus musculus

<400> SEQUENCE: 215
cccuguagaa ccgaauuugu gu                                              22

<210> SEQ ID NO 216
<211> LENGTH: 24
<212> TYPE: RNA
<213> ORGANISM: Unknown
<220> FEATURE:
<223> OTHER INFORMATION: homo sapiens or mus musculus

<400> SEQUENCE: 216
aacccguaga uccgaacuug ugaa                                            24

<210> SEQ ID NO 217
<211> LENGTH: 23
<212> TYPE: RNA
<213> ORGANISM: Unknown
<220> FEATURE:
<223> OTHER INFORMATION: homo sapiens or mus musculus

<400> SEQUENCE: 217
gcuucuccug gcucuccucc cuc                                             23

<210> SEQ ID NO 218
<211> LENGTH: 91
<212> TYPE: RNA
<213> ORGANISM: Drosophila melanogaster

<400> SEQUENCE: 218
uucagccuuu gagaguucca ugcuuccuug cauucaauag uuauauucaa gcauauggaa     60
uguaaagaag uauggagcga aaucuggcga g                                    91

<210> SEQ ID NO 219
<211> LENGTH: 76
<212> TYPE: RNA
<213> ORGANISM: Drosophila melanogaster

<400> SEQUENCE: 219
```
gcugggcucu caaagugguu gugaaaugca uuccgcuuu gcgcggcaua ucacagccag    60
cuuugaugag cuuagc                                                   76

<210> SEQ ID NO 220
<211> LENGTH: 72
<212> TYPE: RNA
<213> ORGANISM: Drosophila melanogaster

<400> SEQUENCE: 220
aucuaagccu caucaagugg uugugauaug gauacccaac gcauaucaca gccagcuuug    60
augagcuagg au                                                       72

<210> SEQ ID NO 221
<211> LENGTH: 77
<212> TYPE: RNA
<213> ORGANISM: Drosophila melanogaster

<400> SEQUENCE: 221
cuucaacugu cuucaaagug gcagugacau guugucaaca auauucauau cacagccagc    60
uuugaggagc guugcgg                                                  77

<210> SEQ ID NO 222
<211> LENGTH: 83
<212> TYPE: RNA
<213> ORGANISM: Drosophila melanogaster

<400> SEQUENCE: 222
uugugucauu cuucaaagug guugugaaau guuugccuuu uuaugccuau ucauaucaca    60
gccagcuuug aggagcgacg cga                                           83

<210> SEQ ID NO 223
<211> LENGTH: 69
<212> TYPE: RNA
<213> ORGANISM: Drosophila melanogaster

<400> SEQUENCE: 223
gauccuggga ugcaucuugu gcaguuaugu uucaaucuca caucacuggg caaagugugu    60
cucaagauc                                                           69

<210> SEQ ID NO 224
<211> LENGTH: 82
<212> TYPE: RNA
<213> ORGANISM: Drosophila melanogaster

<400> SEQUENCE: 224
uugcaauuag uuucuuuggu cguccagccu uagggugauu uuccgguca uaaagcuaga    60 caaccauuga aguucguugu gg                                            82

<210> SEQ ID NO 225
<211> LENGTH: 69
<212> TYPE: RNA
<213> ORGANISM: Drosophila melanogaster

<400> SEQUENCE: 225
gcuaaaagga acgaucguug ugauaugagu uguuccuaa cauaucacag ugauuuuccu    60
uuauaacgc                                                           69

<210> SEQ ID NO 226

```
<211> LENGTH: 81
<212> TYPE: RNA
<213> ORGANISM: Drosophila melanogaster

<400> SEQUENCE: 226
uuuaauguag agggaauagu ugcugugcug uaaguuaaua uaccauaucu auaucacagg      60
gcuguucuuu uuguaccuaa a                                               81

<210> SEQ ID NO 227
<211> LENGTH: 74
<212> TYPE: RNA
<213> ORGANISM: Drosophila melanogaster

<400> SEQUENCE: 227
uaacccaagg gaacuucugc ugcugauaua uuauugaaaa acuacuauau cacaguggcu     60
guucuuuuug guug                                                       74

<210> SEQ ID NO 228
<211> LENGTH: 79
<212> TYPE: RNA
<213> ORGANISM: Drosophila melanogaster

<400> SEQUENCE: 228 caaaagaag ggaacgguug cugaugaugu aguugaaac ucucacaauu uauaucacag       60
uggcuguucu uuuguuug                                                   79

<210> SEQ ID NO 229
<211> LENGTH: 88
<212> TYPE: RNA
<213> ORGANISM: Drosophila melanogaster

<400> SEQUENCE: 229
gagugcauuc cguauggaag acuagugauu uuguuguuug gucuuuggua auaacaauaa     60
aucccuuguc uucuuacggc gugcauuu                                        88

<210> SEQ ID NO 230
<211> LENGTH: 87
<212> TYPE: RNA
<213> ORGANISM: Drosophila melanogaster

<400> SEQUENCE: 230
aaggacaucu guucacaucu uaccgggcag cauuagaucc uuuuuauaac ucuaauacug     60
ucagguaaag augucguccg uguccuu                                         87

<210> SEQ ID NO 231
<211> LENGTH: 78
<212> TYPE: RNA
<213> ORGANISM: Drosophila melanogaster

<400> SEQUENCE: 231
gcuauguugu cuuggguuau cuagcuguau gagugauaaa uaacgucaua aagcuagcuu     60
accgaaguua auauuagc                                                   78

<210> SEQ ID NO 232
<211> LENGTH: 77
<212> TYPE: RNA
<213> ORGANISM: Drosophila melanogaster

<400> SEQUENCE: 232
ccacgucuac ccuguagauc cgaauuuguu uuauacuagc uuuaaggaca aauucgguuc     60
```

```
uagagagguu ugugugg                                                    77

<210> SEQ ID NO 233
<211> LENGTH: 75
<212> TYPE: RNA
<213> ORGANISM: Drosophila melanogaster

<400> SEQUENCE: 233
gcacuuguca agaacuuucu cugugacccg cguguacuua aaagccgcau cacagucuga     60
guucuugcug agugc                                                      75

<210> SEQ ID NO 234
<211> LENGTH: 74
<212> TYPE: RNA
<213> ORGANISM: Drosophila melanogaster

<400> SEQUENCE: 234
uacgguugag uauuacauca gguacggug ugccuuaaau ccaacaacca guacuuaugu      60
cauacuacgc cgug                                                       74

<210> SEQ ID NO 235
<211> LENGTH: 75
<212> TYPE: RNA
<213> ORGANISM: Drosophila melanogaster

<400> SEQUENCE: 235
uacguaacuc cucaaagggu ugugaaaugu cgacuauuau cuacucauau cacagccauu     60
uugaugaguu ucgug                                                      75

<210> SEQ ID NO 236
<211> LENGTH: 68
<212> TYPE: RNA
<213> ORGANISM: Drosophila melanogaster

<400> SEQUENCE: 236
ccaugucguu aaaauguuug ugaacuuaug uauucacaau cauaucacag ccauuuugac     60
gaguuugg                                                              68

<210> SEQ ID NO 237
<211> LENGTH: 70
<212> TYPE: RNA
<213> ORGANISM: Drosophila melanogaster

<400> SEQUENCE: 237
uauuaacgcg ucaaaaugac ugugagcuau guggauuuga cuucauauca cagccauuuu     60
gacgaguuug                                                            70

<210> SEQ ID NO 238
<211> LENGTH: 65
<212> TYPE: RNA
<213> ORGANISM: Drosophila melanogaster

<400> SEQUENCE: 238
ugugggagcg agacguggga cucacugugc uuauuaaaua gucagucuug uuucucucuc     60
cuaua                                                                 65

<210> SEQ ID NO 239
<211> LENGTH: 80
<212> TYPE: RNA
```

<213> ORGANISM: Homo sapiens

<400> SEQUENCE: 239
ugggaugagg uaguagguug uauaguuuua gggucacacc caccacuggg agauaacuau    60
acaaucuacu gucuuccua                                                80

<210> SEQ ID NO 240
<211> LENGTH: 72
<212> TYPE: RNA
<213> ORGANISM: Homo sapiens

<400> SEQUENCE: 240
agguugaggu aguagguugu auaguuuaga auuacaucaa gggagauaac uguacagccu    60
ccuagcuuuc cu                                                       72

<210> SEQ ID NO 241
<211> LENGTH: 74
<212> TYPE: RNA
<213> ORGANISM: Homo sapiens

<400> SEQUENCE: 241
gggugaggua guagguugua uaguuugggg cucugcccug cuaugggaua acuauacaau    60
cuacugucuu uccu                                                     74

<210> SEQ ID NO 242
<211> LENGTH: 83
<212> TYPE: RNA
<213> ORGANISM: Homo sapiens

<400> SEQUENCE: 242
cggggugagg uaguagguug ugugguuuca gggcagugau guugcccuc ggaagauaac     60 uauacaaccu acugccuucc cug                                           83

<210> SEQ ID NO 243
<211> LENGTH: 85
<212> TYPE: RNA
<213> ORGANISM: Homo sapiens

<400> SEQUENCE: 243
gcauccgggu ugagguagua gguuguaugg uuuagaguua cacccugggg aguuaacugu    60
acaaccuucu agcuuuccuu ggagc                                         85

<210> SEQ ID NO 244
<211> LENGTH: 87
<212> TYPE: RNA
<213> ORGANISM: Homo sapiens

<400> SEQUENCE: 244
ccuaggaaga gguaguaggu ugcauaguuu uagggcaggg auuuugccca caaggaggua    60
acuauacgac cugcugccuu ucuuagg                                       87

<210> SEQ ID NO 245
<211> LENGTH: 79
<212> TYPE: RNA
<213> ORGANISM: Homo sapiens

<400> SEQUENCE: 245
cccgggcuga gguaggaggu uguauaguug aggaggacac ccaaggagau cacuauacgg    60
ccuccuagcu uucccagg                                                 79

<210> SEQ ID NO 246
<211> LENGTH: 87
<212> TYPE: RNA
<213> ORGANISM: Homo sapiens

<400> SEQUENCE: 246
ucagagugag guaguagauu guauaguugu gggguaguga uuuuacccug uucaggagau        60
aacuauacaa ucuauugccu uccuga                                            87

<210> SEQ ID NO 247
<211> LENGTH: 85
<212> TYPE: RNA
<213> ORGANISM: Homo sapiens

<400> SEQUENCE: 247
cugugggaug agguaguaga uuguauaguu uuagggucau accccaucuu ggagauaacu        60
auacagucua cugucuuucc cacgg                                             85

<210> SEQ ID NO 248
<211> LENGTH: 83
<212> TYPE: RNA
<213> ORGANISM: Homo sapiens

<400> SEQUENCE: 248
ccuuggagua aaguagcagc acauaauggu uuguggauuu ugaaaaggug caggccauau        60
ugugcugccu caaaaauaca agg                                               83

<210> SEQ ID NO 249
<211> LENGTH: 89
<212> TYPE: RNA
<213> ORGANISM: Homo sapiens

<400> SEQUENCE: 249
gucagcagug ccuuagcagc acguaaauau uggcguuaag auucuaaaau uaucuccagu        60
auuaacugug cugcugaagu aagguugac                                         89

<210> SEQ ID NO 250
<211> LENGTH: 84
<212> TYPE: RNA
<213> ORGANISM: Homo sapiens

<400> SEQUENCE: 250
gucagaauaa ugucaaagug cuuacagugc agguagugau augugcaucu acugcaguga        60
aggcacuugu agcauuaugg ugac                                              84

<210> SEQ ID NO 251
<211> LENGTH: 71
<212> TYPE: RNA
<213> ORGANISM: Homo sapiens

<400> SEQUENCE: 251
uguucuaagg ugcaucuagu gcagauagug aaguagauua gcaucuacug cccuaagugc        60
uccuucuggc a                                                            71

<210> SEQ ID NO 252
<211> LENGTH: 82
<212> TYPE: RNA
<213> ORGANISM: Homo sapiens

```
<400> SEQUENCE: 252
gcaguccucu guuaguuug cauaguugca cuacaagaag aauguaguug ugcaaaucua    60
ugcaaaacug augguggccu gc                                            82

<210> SEQ ID NO 253
<211> LENGTH: 87
<212> TYPE: RNA
<213> ORGANISM: Homo sapiens

<400> SEQUENCE: 253
cacuguucua ugguuaguuu ugcagguuug cauccagcug ugugauauuc ugcugugcaa    60
auccaugcaa aacugacugu gguagug                                       87

<210> SEQ ID NO 254
<211> LENGTH: 96
<212> TYPE: RNA
<213> ORGANISM: Homo sapiens

<400> SEQUENCE: 254
acauugcuac uuacaauuag uuuugcaggu uugcauuuca gcguauauau guauaugugg    60
cugugcaaau ccaugcaaaa cugauuguga uaaugu                             96

<210> SEQ ID NO 255
<211> LENGTH: 71
<212> TYPE: RNA
<213> ORGANISM: Homo sapiens

<400> SEQUENCE: 255
guagcacuaa agugcuuaua gugcagguag uguuuaguua cuacugcau uaugagcacu    60 uaaaguacug c                                                        71

<210> SEQ ID NO 256
<211> LENGTH: 72
<212> TYPE: RNA
<213> ORGANISM: Homo sapiens

<400> SEQUENCE: 256 ugucgggua g cuuaucagac ugauguugac uguugaaucu cauggcaaca ccagucgaug    60
ggcugucuga ca                                                       72

<210> SEQ ID NO 257
<211> LENGTH: 85
<212> TYPE: RNA
<213> ORGANISM: Homo sapiens

<400> SEQUENCE: 257
ggcugagccg caguaguucu ucaguggcaa gcuuuaugac cugacccagc uaaagcugcc    60
aguugaagaa cuguugcccu cugcc                                         85

<210> SEQ ID NO 258
<211> LENGTH: 73
<212> TYPE: RNA
<213> ORGANISM: Homo sapiens

<400> SEQUENCE: 258
ggccggcugg gguuccuggg gaugggauuu gcuuccuguc acaaaucaca uugccaggga    60
uuuccaaccg acc                                                      73
```

<210> SEQ ID NO 259
<211> LENGTH: 68
<212> TYPE: RNA
<213> ORGANISM: Homo sapiens

<400> SEQUENCE: 259
cuccggugcc uacugagcug auaucaguuc ucauuuuaca cacuggcuca guucagcagg    60
aacaggag                                                            68

<210> SEQ ID NO 260
<211> LENGTH: 73
<212> TYPE: RNA
<213> ORGANISM: Homo sapiens

<400> SEQUENCE: 260
cucugccucc cgugccuacu gagcugaaac acaguugguu uguguacacu ggcucaguuc    60
agcaggaaca ggg                                                      73

<210> SEQ ID NO 261
<211> LENGTH: 84
<212> TYPE: RNA
<213> ORGANISM: Homo sapiens

<400> SEQUENCE: 261 ggccagyguguu gagaggcgga gacuugggca auugcuggac gcugcccugg gcauugcacu    60
ugucucgguc ugacagugcc ggcc                                          84

<210> SEQ ID NO 262
<211> LENGTH: 75
<212> TYPE: RNA
<213> ORGANISM: Homo sapiens

<400> SEQUENCE: 262
guggccucgu ucaaguaauc caggauaggc ugugcagguc ccaauggccu aucuugguua    60
cuugcacggg gacgc                                                    75

<210> SEQ ID NO 263
<211> LENGTH: 77
<212> TYPE: RNA
<213> ORGANISM: Homo sapiens

<400> SEQUENCE: 263
ccgggaccca guucaaguaa uucaggauag guugugugcu guccagccug uucuccauua    60
cuuggcucgg ggaccgg                                                  77

<210> SEQ ID NO 264
<211> LENGTH: 78
<212> TYPE: RNA
<213> ORGANISM: Homo sapiens

<400> SEQUENCE: 264
cugaggagca gggcuuagcu gcuugugagc agguccaca ccaagucgug uucacagugg    60
cuaaguuccg cccccccag                                                78

<210> SEQ ID NO 265
<211> LENGTH: 86
<212> TYPE: RNA
<213> ORGANISM: Homo sapiens

<400> SEQUENCE: 265

-continued gguccuugcc cucaaggagc ucacagucua uugaguuacc uuucugacuu ucccacuaga    60
uugugagcuc cuggagggca ggcacu                                        86

<210> SEQ ID NO 266
<211> LENGTH: 64
<212> TYPE: RNA
<213> ORGANISM: Homo sapiens

<400> SEQUENCE: 266
augacugauu ucuuuggug uucagaguca auauaauuuu cuagcaccau cugaaaucgg     60
uuau                                                                64

<210> SEQ ID NO 267
<211> LENGTH: 71
<212> TYPE: RNA
<213> ORGANISM: Homo sapiens

<400> SEQUENCE: 267
gcgacuguaa acauccucga cuggaagcug ugaagccaca gaugggcuuu cagucggaug    60
uuugcagcug c                                                        71

<210> SEQ ID NO 268
<211> LENGTH: 71
<212> TYPE: RNA
<213> ORGANISM: Homo sapiens

<400> SEQUENCE: 268
ggagaggagg caagaugcug gcauagcugu ugaacuggga accugcuaug ccaacauauu    60
gccaucuuuc c                                                        71

<210> SEQ ID NO 269
<211> LENGTH: 70
<212> TYPE: RNA
<213> ORGANISM: Homo sapiens

<400> SEQUENCE: 269
ggagauauug cacauuacua aguugcaugu ugucacggcc ucaaugcaau uuagugugug    60
ugauauuuuc                                                          70

<210> SEQ ID NO 270
<211> LENGTH: 69
<212> TYPE: RNA
<213> ORGANISM: Homo sapiens

<400> SEQUENCE: 270
cuguggugca uuguaguugc auugcauguu cuggugguac ccaugcaaug uuccacagu     60 gcaucacag                                                           69

<210> SEQ ID NO 271
<211> LENGTH: 90
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 271
cacuguggga ugagguagua gguuguauag uuuuagdgguc acacccacca cuggagaua    60 acuauacaau cuacugucuu uccuaacgug                                    90

```
<210> SEQ ID NO 272
<211> LENGTH: 72
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 272
agguugaggu aguagguugu auaguuuaga auuacaucaa gggagauaac uguacagccu    60
ccuagcuuuc cu                                                       72

<210> SEQ ID NO 273
<211> LENGTH: 74
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 273
gggugaggua guagguugua uaguuugggg cucugcccug cuaugggaua acuauacaau    60
cuacugucuu uccu                                                     74

<210> SEQ ID NO 274
<211> LENGTH: 85
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 274 ggcggggluga gguaguaggu ugugugguuu cagggcagug auguugcccc ucggaagaua    60
acuauacaac cuacugccuu cccug                                         85

<210> SEQ ID NO 275
<211> LENGTH: 84
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 275
gcauccgggu ugagguagua gguuguaugg uuuagaguua cacccugggg auuaacugua    60
caaccuucua gcuuuccuug gagc                                          84

<210> SEQ ID NO 276
<211> LENGTH: 87
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 276
ccuaggaaga gguaguaggu ugcauaguuu uagggcaggg auuuugccca caaggaggua    60
acuauacgac cugcugccuu ucuuagg                                       87

<210> SEQ ID NO 277
<211> LENGTH: 79
<212> TYPE: RNA
```

```
<213> ORGANISM: Unknown
<220> FEATURE:
<223> OTHER INFORMATION: D. melanogaster or H. sapiens or M. musculus
      or C. elegans or HeLa cells

<400> SEQUENCE: 277
cccgggcuga gguaggaggu uguauaguug aggaggacac ccaaggagau cacuauacgg      60
ccuccuagcu uucccagg                                                   79

<210> SEQ ID NO 278
<211> LENGTH: 87
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 278
ucagagugag guaguagauu guauaguugu ggguaguga uuuuacccug uucaggagau       60
aacuauacaa ucuauugccu ucccuga                                         87

<210> SEQ ID NO 279
<211> LENGTH: 85
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 279
cugugggaug agguaguaga uuguauaguu uuagggucau accccaucuu ggagauaacu      60
auacagucua cugucuuucc cacgg                                           85

<210> SEQ ID NO 280
<211> LENGTH: 88
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 280
ccaggcugag guaguaguuu gugcaguuug agggucuaug auaccacccg guacaggaga     60
uaacuguaca ggccacugcc uugccagg                                        88

<210> SEQ ID NO 281
<211> LENGTH: 85
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 281
cuggcugagg uaguaguuug ugcuguuggu cggguuguga cauugcccgc uguggagaua     60
acugcgcaag cuacugccuu gcuag                                           85

<210> SEQ ID NO 282
<211> LENGTH: 91
<212> TYPE: RNA
<213> ORGANISM: Unknown
<220> FEATURE:
<223> OTHER INFORMATION: D. melanogaster or H. sapiens or M. musculus
      or C. elegans or HeLa cells
```

```
<400> SEQUENCE: 282
uucagccuuu gagaguucca ugcuuccuug cauucaauag uuauauucaa gcauauggaa    60
uguaaagaag uauggagcga aaucggcga g                                   91

<210> SEQ ID NO 283
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 283
ugggaaacau acuucuuuau augcccauau ggaccugcua agcuauggaa uguaaagaag    60
uauguaucuc a                                                        71

<210> SEQ ID NO 284
<211> LENGTH: 77
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 284
gcuugggaca cauacuucuu uauaugccca uaugaaccug cuaagcuaug gaauguaaag    60
aaguauguau uucaggc                                                  77

<210> SEQ ID NO 285
<211> LENGTH: 76
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 285
gcugggcucu caaagugguu gugaaaugca uuccgcuuu gcgcggcaua ucacagccag     60
cuuugaugag cuuagc                                                   76

<210> SEQ ID NO 286
<211> LENGTH: 72
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 286
aucuaagccu caucaagugg uugugauaug gauacccaac gcauaucaca gccagcuuug    60
augagcuagg au                                                       72

<210> SEQ ID NO 287
<211> LENGTH: 77
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 287
cuucaacugu cuucaaagug gcagugacau guugucaaca auauucauau cacagccagc    60
```

```
uuugaggagc guugcgg                                                    77

<210> SEQ ID NO 288
<211> LENGTH: 83
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 288
uugugucauu cuucaaagug guugugaaau guuugccuuu uuaugccuau ucauaucaca      60
gccagcuuug aggagcgacg cga                                             83

<210> SEQ ID NO 289
<211> LENGTH: 69
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 289
gauccuggga ugcaucuugu gcaguuaugu uucaaucuca caucacuggg caaagugugu      60
cucaagauc                                                             69

<210> SEQ ID NO 290
<211> LENGTH: 82
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 290
uugcaauuag uuucuuuggu cguccagccu uagggugauu uuuccgguca uaaagcuaga      60
caaccauuga aguucguugu gg                                              82

<210> SEQ ID NO 291
<211> LENGTH: 69
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 291
gcuaaaagga acgaucguug ugauaugagu uguuccuaa cauaucacag ugauuuuccu       60
uuauaacgc                                                             69

<210> SEQ ID NO 292
<211> LENGTH: 81
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 292
uuuaauguag agggaauagu ugcugugcug uaaguuaaua uaccauaucu auaucacagg      60
gcuguucuuu uuguaccuaa a                                               81
```

<210> SEQ ID NO 293
<211> LENGTH: 74
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 293
uaacccaagg gaacuucugc ugcugauaua uuauugaaaa acuacuauau cacaguggcu    60
guucuuuuug guug                                                    74

<210> SEQ ID NO 294
<211> LENGTH: 79
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 294
caaaaagaag ggaacgguug cugaugaugu aguugaaac ucucacaauu uauaucacag    60
uggcuguucu uuuuguuug                                               79

<210> SEQ ID NO 295
<211> LENGTH: 88
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 295
gagugcauuc cguauggaag acuagugauu uuguuguuug gucuuuggua auaacaauaa    60
aucccuuguc uucuuacggc gugcauuu                                     88

<210> SEQ ID NO 296
<211> LENGTH: 87
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 296
aaggacaucu guucacaucu uaccgggcag cauuagaucc uuuuuauaac ucuaauacug    60
ucagguaaag augucguccg uguccuu                                      87

<210> SEQ ID NO 297
<211> LENGTH: 78
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 297
gcuauguugu cuuugguuau cuagcuguau gagugauaaa uaacgucaua aagcuagcuu    60
accgaaguua auauuagc                                                78

<210> SEQ ID NO 298
<211> LENGTH: 77
<212> TYPE: RNA
<213> ORGANISM: Unknown

```
<220> FEATURE:
<223> OTHER INFORMATION: D. melanogaster or H. sapiens or M. musculus
      or C. elegans or HeLa cells

<400> SEQUENCE: 298
ccacgucuac ccguagauc cgaauuuguu uuauacuagc uuuaaggaca aaucgguuc        60 uagagagguu ugugugg                                                    77

<210> SEQ ID NO 299
<211> LENGTH: 75
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 299
gcacuuguca agaacuuucu cugugacccg cguguacuua aaagccgcau cacagucuga     60
guucuugcug agugc                                                     75

<210> SEQ ID NO 300
<211> LENGTH: 74
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 300
uacgguugag uauuacauca gguacuggug ugccuuaaau ccaacaacca guacuuaugu     60
cauacuacgc cgug                                                      74

<210> SEQ ID NO 301
<211> LENGTH: 75
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 301
uacguaacuc cucaaagggu ugugaaaugu cgacuauuau cuacucauau cacagccauu     60
uugaugaguu ucgug                                                     75

<210> SEQ ID NO 302
<211> LENGTH: 68
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 302
ccaugucguu aaaauguuug ugaacuuaug uauucacaau cauaucacag ccauuuugac     60
gaguuugg                                                             68

<210> SEQ ID NO 303
<211> LENGTH: 70
<212> TYPE: RNA
<213> ORGANISM: Unknown
<220> FEATURE:
<223> OTHER INFORMATION: D. melanogaster or H. sapiens or M. musculus
      or C. elegans or HeLa cells
```

-continued

```
<400> SEQUENCE: 303
uauuaacgcg ucaaaaugac ugugagcuau guggauuuga cuucauauca cagccauuuu    60
gacgaguuug                                                            70

<210> SEQ ID NO 304
<211> LENGTH: 65
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 304
ugugggagcg agacguggga cucacugugc uuauuaaaua gucagucuug uuucucucuc    60
cuaua                                                                 65

<210> SEQ ID NO 305
<211> LENGTH: 83
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 305
ccuuggagua aaguagcagc acauaauggu uuguggauuu ugaaaaggug caggccauau    60
ugugcugccu caaaaauaca agg                                             83

<210> SEQ ID NO 306
<211> LENGTH: 64
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 306
cuguagcagc acaucauggu uuacauacua cagucaagau gcgaaucauu auuugcugcu    60
cuag                                                                  64

<210> SEQ ID NO 307
<211> LENGTH: 89
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 307
gucagcagug ccuuagcagc acguaaauau uggcguuaag auucuaaaau uaucuccagu    60
auuaacugug cugcugaagu aagguugac                                       89

<210> SEQ ID NO 308
<211> LENGTH: 81
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 308
guuccacucu agcagcacgu aaauauuggc guagugaaau auauauuaaa caccaauauu    60
```

```
acugugcugc uuuaguguga c                                              81

<210> SEQ ID NO 309
<211> LENGTH: 84
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 309
gucagaauaa ugucaaagug cuuacagugc agguagugau augugcaucu acugcaguga   60
aggcacuugu agcauuaugg ugac                                          84

<210> SEQ ID NO 310
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 310
uguucuaagg ugcaucuagu gcagauagug aaguagauua gcaucuacug cccuaagugc   60
uccuucuggc a                                                        71

<210> SEQ ID NO 311
<211> LENGTH: 82
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 311
gcagcccucu guuaguuuug cauaguugca cuacaagaag aauguaguug ugcaaaucua   60
ugcaaaacug augguggccu gc                                            82

<210> SEQ ID NO 312
<211> LENGTH: 87
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 312
cacuguucua ugguuaguuu ugcagguuug cauccagcug ugugauauuc ugcugugcaa   60
auccaugcaa aacugacugu gguagug                                       87

<210> SEQ ID NO 313
<211> LENGTH: 96
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 313
acauugcuac uuacaauuag uuuugcaggu uugcauuuca gcguauauau guauaugugg   60
cugugcaaau ccaugcaaaa cugauuguga uaaugu                             96

<210> SEQ ID NO 314
```

```
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 314
guagcacuaa agugcuuaua gugcagguag uguuuaguua ucuacugcau uaugagcacu    60
uaaaguacug c                                                        71

<210> SEQ ID NO 315
<211> LENGTH: 72
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 315 ugucgguag cuuaucagac ugauguugac uguugaaucu cauggcaaca ccagucgaug     60
ggcugucuga ca                                                       72

<210> SEQ ID NO 316
<211> LENGTH: 85
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 316
ggcugagccg caguaguucu ucagguggcaa gcuuuauguc cugacccagc uaaagcugcc   60
aguugaagaa cuguugcccu cugcc                                         85

<210> SEQ ID NO 317
<211> LENGTH: 73
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 317
ggccggcugg gguuccuggg gaugggauuu gcuuccuguc acaaaucaca uugccaggga    60
uuuccaaccg acc                                                      73

<210> SEQ ID NO 318
<211> LENGTH: 74
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 318
ggcugcuugg guuccuggca ugcugauuug ugacuugaga uuaaaaucac auugccaggg    60
auuaccacgc aacc                                                     74

<210> SEQ ID NO 319
<211> LENGTH: 68
<212> TYPE: RNA
<213> ORGANISM: Unknown
<220> FEATURE:
```

<223> OTHER INFORMATION: D. melanogaster or H. sapiens or M. musculus
or C. elegans or HeLa cells

<400> SEQUENCE: 319
cuccggugcc uacugagcug auaucaguuc ucauuuuaca cacuggcuca guucagcagg    60
aacaggag                                                            68

<210> SEQ ID NO 320
<211> LENGTH: 73
<212> TYPE: RNA
<213> ORGANISM: Unknown
<220> FEATURE:
<223> OTHER INFORMATION: D. melanogaster or H. sapiens or M. musculus
or C. elegans or HeLa cells

<400> SEQUENCE: 320
cucugccucc cgugccuacu gagcugaaac acaguugguu uguguacacu ggcucaguuc    60
agcaggaaca ggg                                                      73

<210> SEQ ID NO 321
<211> LENGTH: 84
<212> TYPE: RNA
<213> ORGANISM: Unknown
<220> FEATURE:
<223> OTHER INFORMATION: D. melanogaster or H. sapiens or M. musculus
or C. elegans or HeLa cells

<400> SEQUENCE: 321
ggccaguguu gagaggcgga dacuugggca auugcuggac gcugcccugg gcauugcacu    60
ugucucgguc ugacagugcc ggcc                                          84

<210> SEQ ID NO 322
<211> LENGTH: 86
<212> TYPE: RNA
<213> ORGANISM: Unknown
<220> FEATURE:
<223> OTHER INFORMATION: D. melanogaster or H. sapiens or M. musculus
or C. elegans or HeLa cells

<400> SEQUENCE: 322 aggccgugge cucguucaag uaauccagga uaggcugugc aggucccaau ggccuaucuu    60
gguuacuugc acgggacgc gggccu                                         86

<210> SEQ ID NO 323
<211> LENGTH: 77
<212> TYPE: RNA
<213> ORGANISM: Unknown
<220> FEATURE:
<223> OTHER INFORMATION: D. melanogaster or H. sapiens or M. musculus
or C. elegans or HeLa cells

<400> SEQUENCE: 323
ccgggaccca guucaaguaa uucaggauag guugugugcu guccagccug uucuccauua    60
cuuggcucgg ggaccgg                                                  77

<210> SEQ ID NO 324
<211> LENGTH: 78
<212> TYPE: RNA
<213> ORGANISM: Unknown
<220> FEATURE:
<223> OTHER INFORMATION: D. melanogaster or H. sapiens or M. musculus
or C. elegans or HeLa cells

<400> SEQUENCE: 324
cugaggagca gggcuuagcu gcuugugagc aggguccaca ccaagucgug uucacagugg    60
cuaaguuccg cccccccag                                                78

<210> SEQ ID NO 325
<211> LENGTH: 73
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 325
aggugcagag cuuagcugau uggugaacag ugauuggauu ccgcuuuguu cacaguggcu    60
aaguucugca ccu                                                      73

<210> SEQ ID NO 326
<211> LENGTH: 86
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 326
gguccuugcc cucaaggagc ucacagucua uugaguuacc uuucugacuu ucccacuaga    60
uugugagcuc cuggagggca ggcacu                                        86

<210> SEQ ID NO 327
<211> LENGTH: 64
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 327
augacugauu ucuuuggug uucagaguca auauaauuuu cuagcaccau cugaaaucgg     60
uuau                                                                64

<210> SEQ ID NO 328
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 328
aggaagcugg uuucauaugg ugguuuagau uuaaauagug auugcuagc accauuugaa     60 aucaguguuc u                                                        71

<210> SEQ ID NO 329
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 329
gcgacuguaa acauccucga cuggaagcug ugaagccaca aaugggcuuu cagucggaug    60
uuugcagcug c                                                        71

<210> SEQ ID NO 330
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 330
gcgacuguaa acauccucga cuggaagcug ugaagccaca aaugggcuuu cagucggaug    60
uuugcagcug c                                                        71

<210> SEQ ID NO 331
<211> LENGTH: 60
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 331
auguaaacau ccuacacuca gcugucauac augcguuggc ugggaugugg auguuuacgu    60

<210> SEQ ID NO 332
<211> LENGTH: 72
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 332
agauacugua aacauccuac acucucagcu guggaaagua agaaagcugg gagaaggcug    60
uuuacucuuu cu                                                       72

<210> SEQ ID NO 333
<211> LENGTH: 70
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 333
guuguuguaa acaucccga cuggaagcug uaagacacag cuaagcuuuc agucagaugu    60
uugcugcuac                                                          70

<210> SEQ ID NO 334
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 334
ggagaggagg caagaugcug gcauagcugu ugaacuggga accugcuaug ccaacauauu    60
gccaucuuuc c                                                        71

<210> SEQ ID NO 335
<211> LENGTH: 70
<212> TYPE: RNA
<213> ORGANISM: Unknown

```
<220> FEATURE:
<223> OTHER INFORMATION: D. melanogaster or H. sapiens or M. musculus
      or C. elegans or HeLa cells

<400> SEQUENCE: 335
ggagauauug cacauuacua aguugcaugu ugucacggcc ucaaugcaau uuagugugug    60
ugauauuuc                                                           70

<210> SEQ ID NO 336
<211> LENGTH: 69
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 336
cuguggugca uuguaguugc auugcauguu cuggugguac ccaugcaaug uuccacagu     60 gcaucacag                                                           69

<210> SEQ ID NO 337
<211> LENGTH: 65
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 337
cauaaacccg uagauccgau cuugugguga aguggaccgc gcaagcucgu uucuaugggu    60
cugug                                                               65

<210> SEQ ID NO 338
<211> LENGTH: 70
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 338
ggcacccacc cguagaaccg accuugcggg gccuucgccg cacacaagcu cgucucugug    60
gguccguguc                                                          70

<210> SEQ ID NO 339
<211> LENGTH: 57
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 339
ucaguuauca cagugcugau gcuguccauu cuaaagguac aguacuguga uaacuga       57

<210> SEQ ID NO 340
<211> LENGTH: 66
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 340
```

```
agcuguggag ugugacaaug guguuugugu ccaaaccauc aaacgccauu aucacacuaa    60
auagcu                                                              66

<210> SEQ ID NO 341
<211> LENGTH: 73
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 341
ugacagcaca uuauuacuuu ugguacgcgc ugugacacuu caaacucgua ccgugaguaa    60
uaaugcgcgg uca                                                      73

<210> SEQ ID NO 342
<211> LENGTH: 68
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 342
cucugcgugu ucacagcgga ccuugauuua augucuauac aauuaaggca cgcggugaau    60
gccaagag                                                            68

<210> SEQ ID NO 343
<211> LENGTH: 67
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 343
cucuccgugu ucacagcgga ccuugauuua augucauaca auuaaggcac gcggugaaug    60
ccaagag                                                             67

<210> SEQ ID NO 344
<211> LENGTH: 68
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 344
cugggucccu gagacccuuu aaccugugag gacguccagg gucacaggug agguucuugg    60
gagccugg                                                            68

<210> SEQ ID NO 345
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 345
gccuaguccc ugagacccua acuugugagg uauuuuagua acaucacaag ucagguucuu    60
gggaccuagg c                                                        71
```

```
<210> SEQ ID NO 346
<211> LENGTH: 63
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 346
gcacauuauu acuuugguga cgcgcuguga cacuucaaac ucguaccgug aguaauaaug      60
cgc                                                                   63

<210> SEQ ID NO 347
<211> LENGTH: 70
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 347
ccagccugcu gaagcucaga gggcucugau ucagaaagau caucggaucc gucugagcuu      60
ggcuggucgg                                                            70

<210> SEQ ID NO 348
<211> LENGTH: 70
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 348
guuggauucg gggccguagc acugucugag agguuuacau uucucacagu gaaccggucu      60
cuuuuucagc                                                            70

<210> SEQ ID NO 349
<211> LENGTH: 72
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 349
ggaucuuuuu gcggucuggg cuugcuguuc cucucaacag uagucaggaa gcccuuaccc      60
caaaaaguau cu                                                         72

<210> SEQ ID NO 350
<211> LENGTH: 64
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 350
gagcucuuuu cacauugugc uacugucuaa cguguaccga gcagugcaau guuaaaggg       60 cauc                                                                  64

<210> SEQ ID NO 351
<211> LENGTH: 72
<212> TYPE: RNA
```

-continued

```
<213> ORGANISM: Unknown
<220> FEATURE:
<223> OTHER INFORMATION: D. melanogaster or H. sapiens or M. musculus
      or C. elegans or HeLa cells

<400> SEQUENCE: 351
guuguuaucu uugguuaucu agcuguauga guguauuggu cuucauaaag cuagauaacc    60
gaaaguaaaa ac                                                       72

<210> SEQ ID NO 352
<211> LENGTH: 66
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 352
gggcaaccgu ggcuuucgau uguuacugug ggaaccggag guaacagucu acagccaugg    60
ucgccc                                                              66

<210> SEQ ID NO 353
<211> LENGTH: 68
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 353
gcuaaagcug guaaaaugga accaaaucgc cucuucaaug gauuuggucc ccuucaacca    60
gcuguagc                                                            68

<210> SEQ ID NO 354
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 354
aggguguguu acugguugac cagaggggcg ugcacucugu cacccugug ggccaccag     60 ucaccaaccc u                                                        71

<210> SEQ ID NO 355
<211> LENGTH: 60
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 355
cuauggcuuu uuauuccuau gugauucuau ugcucgcuca uauagggauu ggagccgugg    60

<210> SEQ ID NO 356
<211> LENGTH: 62
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 356
```

```
gaggacucca uuuguuuga ugauggauuc uuaagcucca ucaucgucuc aaaugagucu    60
uc                                                                 62

<210> SEQ ID NO 357
<211> LENGTH: 73
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 357
cuucggugac ggguauucuu ggguggauaa uacggauuac guuguuauug cuuaagaaua    60
cgcguagucg agg                                                       73

<210> SEQ ID NO 358
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 358
cagcuggugu ugugaaucag gccgacgagc agcgcauccu cuuacccggc uauuucacga    60
caccaggguu g                                                         71

<210> SEQ ID NO 359
<211> LENGTH: 68
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 359
guguauucua cagugcacgu gucuccagug uggcucggag gcuggagacg cggcccuguu    60
ggaguaac                                                             68

<210> SEQ ID NO 360
<211> LENGTH: 70
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 360
ccugccagug guuuuacccu augguagguu acgucaugcu guucuaccac aggguagaac    60
cacggacagg                                                           70

<210> SEQ ID NO 361
<211> LENGTH: 72
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 361
ggguccaucu uccagugcag uguuggaugg uugaaguaug aagcuccuaa cacugucugg    60
uaaagauggc cc                                                        72
```

<210> SEQ ID NO 362
<211> LENGTH: 64
<212> TYPE: RNA
<213> ORGANISM: Unknown
<220> FEATURE:
<223> OTHER INFORMATION: D. melanogaster or H. sapiens or M. musculus
    or C. elegans or HeLa cells

<400> SEQUENCE: 362
acccauaaag uagaaagcac uacuaacagc acuggagggu guaguguuuc cuacuuuaug    60
gaug                                                                64

<210> SEQ ID NO 363
<211> LENGTH: 64
<212> TYPE: RNA
<213> ORGANISM: Unknown
<220> FEATURE:
<223> OTHER INFORMATION: D. melanogaster or H. sapiens or M. musculus
    or C. elegans or HeLa cells

<400> SEQUENCE: 363
acccauaaag uagaaagcac uacuaacagc acuggagggu guaguguuuc cuacuuuaug    60
gaug                                                                64

<210> SEQ ID NO 364
<211> LENGTH: 71
<212> TYPE: RNA
<213> ORGANISM: Unknown
<220> FEATURE:
<223> OTHER INFORMATION: D. melanogaster or H. sapiens or M. musculus
    or C. elegans or HeLa cells

<400> SEQUENCE: 364
ugacgggcga gcuuuuggcc cggguuauac cugaugcuca cguauaagac gagcaaaaag    60
cuuguugguc a                                                        71

<210> SEQ ID NO 365
<211> LENGTH: 63
<212> TYPE: RNA
<213> ORGANISM: Unknown
<220> FEATURE:
<223> OTHER INFORMATION: D. melanogaster or H. sapiens or M. musculus
    or C. elegans or HeLa cells

<400> SEQUENCE: 365
ccugaggugc agugcugcau cucuggucag uugggagucu gagaugaagc acuguagcuc    60
agg                                                                 63

<210> SEQ ID NO 366
<211> LENGTH: 66
<212> TYPE: RNA
<213> ORGANISM: Unknown
<220> FEATURE:
<223> OTHER INFORMATION: D. melanogaster or H. sapiens or M. musculus
    or C. elegans or HeLa cells

<400> SEQUENCE: 366
ggcugggaua ucaucauaua cuguaaguuu gugaugagac acuacaguau agaugaugua    60
cuaguc                                                              66

<210> SEQ ID NO 367
<211> LENGTH: 70

<210> SEQ ID NO 367
<211> LENGTH: 70
<212> TYPE: RNA
<213> ORGANISM: Unknown
<220> FEATURE:
<223> OTHER INFORMATION: D. melanogaster or H. sapiens or M. musculus
or C. elegans or HeLa cells

<400> SEQUENCE: 367
cucacggucc aguuucccca ggaaucccuu ggaugcuaag auggggauuc cuggaaauac    60
uguucuugag                                                          70

<210> SEQ ID NO 368
<211> LENGTH: 65
<212> TYPE: RNA
<213> ORGANISM: Unknown
<220> FEATURE:
<223> OTHER INFORMATION: D. melanogaster or H. sapiens or M. musculus
or C. elegans or HeLa cells

<400> SEQUENCE: 368
agcucugaga acugaauucc auggguuaua ucaaugucag accugugaaa uucaguucuu    60
cagcu                                                               65

<210> SEQ ID NO 369
<211> LENGTH: 72
<212> TYPE: RNA
<213> ORGANISM: Unknown
<220> FEATURE:
<223> OTHER INFORMATION: D. melanogaster or H. sapiens or M. musculus
or C. elegans or HeLa cells

<400> SEQUENCE: 369
aaucuaaaga caacauuucu gcacacacac cagacuaugg aagccagugu guggaaaugc    60
uucugcuaga uu                                                       72

<210> SEQ ID NO 370
<211> LENGTH: 68
<212> TYPE: RNA
<213> ORGANISM: Unknown
<220> FEATURE:
<223> OTHER INFORMATION: D. melanogaster or H. sapiens or M. musculus
or C. elegans or HeLa cells

<400> SEQUENCE: 370
gaggcaaagu ucugagacac uccgacucug aguaugauag aagucagugc acuacagaac    60
uuugucuc                                                            68

<210> SEQ ID NO 371
<211> LENGTH: 66
<212> TYPE: RNA
<213> ORGANISM: Unknown
<220> FEATURE:
<223> OTHER INFORMATION: D. melanogaster or H. sapiens or M. musculus
or C. elegans or HeLa cells

<400> SEQUENCE: 371
ggcucuggcu ccgugucuuc acucccgugu uuguccgagg agggagggag ggacagaggc    60
ggggcu                                                              66

<210> SEQ ID NO 372
<211> LENGTH: 65
<212> TYPE: RNA
<213> ORGANISM: Unknown
<220> FEATURE:
<223> OTHER INFORMATION: D. melanogaster or H. sapiens or M. musculus -continued or C. elegans or HeLa cells

<400> SEQUENCE: 372
cccugucucc caacccuugu accagugcug ugccucagac ccugguacag gccuggggga    60
uaggg                                                               65

<210> SEQ ID NO 373
<211> LENGTH: 68
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 373
ccugcccucg aggagcucac agucaguau gucuccuccc uacuagacug aggcccuug      60 aggacagg                                                            68

<210> SEQ ID NO 374
<211> LENGTH: 73
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 374
ccgggccuag guucugugau acacuccgac ucgggcucug gagcagucag ugcaugacag    60
aacuugggcc cgg                                                      73

<210> SEQ ID NO 375
<211> LENGTH: 69
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 375
cagugucauu uuugugaugu ugcagcuagu aauaugagcc caguugcaua gucacaaaag    60
ugaucauug                                                           69

<210> SEQ ID NO 376
<211> LENGTH: 66
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 376
gaagauaggu uauccguguu gccuucgcuu uauuugugac gaaucauaca cgguugaccu    60
auuuuu                                                              66

<210> SEQ ID NO 377
<211> LENGTH: 65
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 377

| cguuaaugc uaauugugau aggguuuug gccucugacu gacuccuacc uguuagcauu | 60 |
| aacag | 65 |

<210> SEQ ID NO 378
<211> LENGTH: 76
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 378

| ccauggaaca uucaacgcug ucggugaguu ugggauucaa aaacaaaaaa accaccgacc | 60 |
| guugacugua ccuugg | 76 |

<210> SEQ ID NO 379
<211> LENGTH: 75
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 379

| accauuuuug gcaauggag aacucacacc gguaagguaa ugggaccccgg gguucuaga | 60 |
| cuugccaacu auggu | 75 |

<210> SEQ ID NO 380
<211> LENGTH: 70
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 380

| cuguguaugg cacgguaga auucacugug aacagucuca gucagugaau uaccgaaggg | 60 |
| ccauaaacag | 70 |

<210> SEQ ID NO 381
<211> LENGTH: 73
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 381

| uggaucuuuu ugcggucugg gcuugcuguu uucucgacag uagucaggaa gcccuuaccc | 60 |
| caaaaaguau cua | 73 |

<210> SEQ ID NO 382
<211> LENGTH: 69
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 382

| ccuuccuua ucacuuuucc agccagcuuu gugacucuaa guguuggacg gagaacugau | 60 |
| aaggguagg | 69 |

```
<210> SEQ ID NO 383
<211> LENGTH: 65
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 383
agggauugga gagaaaggca guuccugaug gucccculccc aggggcuggc uuuccucugg    60
uccuu                                                                65

<210> SEQ ID NO 384
<211> LENGTH: 71
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 384
acuuuccaaa gaauucuccu uuugggcuuu cucauuuuau uuuaagcccu aaggugaauu    60
uuuugggaag u                                                         71

<210> SEQ ID NO 385
<211> LENGTH: 61
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 385
ucaggcuaca acacaggacc cgggcgcugc ucgaccccu cgucuugu guugcagccg       60 g                                                                    61

<210> SEQ ID NO 386
<211> LENGTH: 65
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 386
gggcaucuua ccggacagug cuggauuucu uggcuugacu cuaacacugu cugguaacga    60
uguuc                                                                65

<210> SEQ ID NO 387
<211> LENGTH: 68
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 387
ucucacaucc cuugcauggu ggagggugag cucucugaaa accccucccca caugcagggu    60 uugcagga                                                             68

<210> SEQ ID NO 388
<211> LENGTH: 68
<212> TYPE: RNA
```

```
<213> ORGANISM: Unknown
<220> FEATURE:
<223> OTHER INFORMATION: D. melanogaster or H. sapiens or M. musculus
      or C. elegans or HeLa cells

<400> SEQUENCE: 388
cuccggugcc uacugagcug auaucaguuc ucauuucaca cacuggcuca guucagcagg      60
aacaggag                                                              68

<210> SEQ ID NO 389
<211> LENGTH: 67
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 389
cugugugaua uguuugauau auuagguugu uauuuaaucc aacuauauau caagcauauu      60
ccuacag                                                               67

<210> SEQ ID NO 390
<211> LENGTH: 74
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 390
agcgggcaac ggaaucccaa aagcagcugu ugucuccaga gcauuccagc ugcacuugga      60
uuucguuccc ugcu                                                       74

<210> SEQ ID NO 391
<211> LENGTH: 62
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 391
cugaccuaug aauugacagc cagugcucuc gucuccccuc uggcugccaa uuccauaggu      60
ca                                                                    62

<210> SEQ ID NO 392
<211> LENGTH: 72
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 392
uccugccggu gguuuuaccc uaugguaggu uacgucaugc uguucuacca caggguagaa      60
ccacggacag ga                                                         72

<210> SEQ ID NO 393
<211> LENGTH: 66
<212> TYPE: RNA
<213> ORGANISM: Unknown
<220> FEATURE:
<223> OTHER INFORMATION: D. melanogaster or H. sapiens or M. musculus
      or C. elegans or HeLa cells
```

<400> SEQUENCE: 393
gagagcuggg ucuuugcggg caagaugaga gugucaguuc aacuggccua caaaguccca    60
guccuc    66

<210> SEQ ID NO 394
<211> LENGTH: 67
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 394 aucggguguaa acagcaacuc caugggacu gugcucggau uccaguggag cugcuguuac    60
uucugau    67

<210> SEQ ID NO 395
<211> LENGTH: 58
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 395
uagcagcaca gaaauauugg caugggggaag ugagucugcc aauauuggcu gugcugcu    58

<210> SEQ ID NO 396
<211> LENGTH: 70
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 396
gugaauuagg uaguuucaug uuguugggcc ugggguuucug aacacaacaa cauuaaacca    60
cccgauucac    70

<210> SEQ ID NO 397
<211> LENGTH: 75
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 397
ggcugugccg gguagagagg gcagugggag guaagagcuc uucacccuuc accaccuucu    60
ccacccagca uggcc    75

<210> SEQ ID NO 398
<211> LENGTH: 62
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 398
ucauuggucc agaggggaga uagguuccug ugauuuuucc uucuucucua uagaauaaau    60
ga    62

```
<210> SEQ ID NO 399
<211> LENGTH: 70
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 399
gccaacccag uguucagacu accuguucag gaggcuggga cauguacagu agucugcaca    60
uugguuaggc                                                          70

<210> SEQ ID NO 400
<211> LENGTH: 70
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 400
gccguggcca ucuuacuggg cagcauugga uagugucuga ucucuaauac ugccugguaa    60
ugaugacggc                                                          70

<210> SEQ ID NO 401
<211> LENGTH: 66
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 401
uaccuuacuc aguaaggcau uguucuucua uauuaauaaa ugaacagugc cuuucugugu    60
agggua                                                              66

<210> SEQ ID NO 402
<211> LENGTH: 72
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 402
guuccuuuuu ccuaugcaua uacuucuuug uggaucuggu cuaaagaggu auagcgcaug    60
ggaagaugga gc                                                       72

<210> SEQ ID NO 403
<211> LENGTH: 68
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 403
gguccagugg uucuugacag uucaacaguu cuguagcaca auugugaaau guuuaggacc    60
acuagacc                                                            68

<210> SEQ ID NO 404
<211> LENGTH: 68
```

<212> TYPE: RNA
<213> ORGANISM: Unknown
<220> FEATURE:
<223> OTHER INFORMATION: D. melanogaster or H. sapiens or M. musculus
    or C. elegans or HeLa cells

<400> SEQUENCE: 404
uggacuuccc uuugucaucc uaugccugag aauauaugaa ggaggcuggg aaggcaaagg    60
gacguuca                                                            68

<210> SEQ ID NO 405
<211> LENGTH: 68
<212> TYPE: RNA
<213> ORGANISM: Unknown
<220> FEATURE:
<223> OTHER INFORMATION: D. melanogaster or H. sapiens or M. musculus
    or C. elegans or HeLa cells

<400> SEQUENCE: 405
cucuuguccu ucauuccacc ggagucuguc uuaugccaac cagauuucag uggagugaag    60
cucaggag                                                            68

<210> SEQ ID NO 406
<211> LENGTH: 76
<212> TYPE: RNA
<213> ORGANISM: Unknown
<220> FEATURE:
<223> OTHER INFORMATION: D. melanogaster or H. sapiens or M. musculus
    or C. elegans or HeLa cells

<400> SEQUENCE: 406
gccuggucca gugguucuug acaguucaac aguucuguag cacaauugug aaauguuuag    60
gaccacuaga cccggc                                                   76

<210> SEQ ID NO 407
<211> LENGTH: 73
<212> TYPE: RNA
<213> ORGANISM: Unknown
<220> FEATURE:
<223> OTHER INFORMATION: D. melanogaster or H. sapiens or M. musculus
    or C. elegans or HeLa cells

<400> SEQUENCE: 407
ccaggccaca ugcuucuuua uauccucaua gauaucucag cacuauggaa uguaaggaag    60 uguugguuu ugg                                                       73

<210> SEQ ID NO 408
<211> LENGTH: 70
<212> TYPE: RNA
<213> ORGANISM: Unknown
<220> FEATURE:
<223> OTHER INFORMATION: D. melanogaster or H. sapiens or M. musculus
    or C. elegans or HeLa cells

<400> SEQUENCE: 408
gccaucccag uguucagacu accuguucag gaggcuggga cauguacagu agucugcaca    60
uugguuaggc                                                          70

<210> SEQ ID NO 409
<211> LENGTH: 68
<212> TYPE: RNA
<213> ORGANISM: Unknown
<220> FEATURE:
<223> OTHER INFORMATION: D. melanogaster or H. sapiens or M. musculus or C. elegans or HeLa cells

<400> SEQUENCE: 409
uauauacccu guagaaccga auuugugugg uacccacaua gucacagauu cgauucuagg    60
ggaauaua                                                             68

<210> SEQ ID NO 410
<211> LENGTH: 63
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 410
cacaaacccg uagauccgaa cuugugcuga uucugcacac aagcuugugu cuauagguau    60
gug                                                                  63

<210> SEQ ID NO 411
<211> LENGTH: 79
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 411
aaggcagggg ugagggguug cgggaggagc cgggcggagg cugcggcuug cgcuucuccu    60
ggcucuccuc ccucuccuu                                                 79

<210> SEQ ID NO 412
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 412
ugagguagua gguuguauag uu                                             22

<210> SEQ ID NO 413
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 413
ugagguagua gguuguauag uu                                             22

<210> SEQ ID NO 414
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 414
ugagguagua gguuguauag uu                                             22

<210> SEQ ID NO 415

```
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 415
ugagguagua gguugugugg uu                                              22

<210> SEQ ID NO 416
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 416
ugagguagua gguuguaugg uu                                              22

<210> SEQ ID NO 417
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 417
agagguagua gguugcauag u                                               21

<210> SEQ ID NO 418
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 418
ugagguagga gguuguauag u                                               21

<210> SEQ ID NO 419
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 419
ugagguagua gauuguauag uu                                              22

<210> SEQ ID NO 420
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 420
ugagguagua gauuguauag uu                                              22

<210> SEQ ID NO 421
<211> LENGTH: 22
```

```
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 421
ugagguagua guuuguacag ua                                              22

<210> SEQ ID NO 422
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 422
ugagguagua guguguacag uu                                              22

<210> SEQ ID NO 423
<211> LENGTH: 19
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 423
ugagguagua guuugugcu                                                  19

<210> SEQ ID NO 424
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 424
uggaauguaa agaaguaugg ag                                              22

<210> SEQ ID NO 425
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 425
uggaauguaa agaaguaugu aa                                              22

<210> SEQ ID NO 426
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 426
uggaauguaa agaaguaugu ac                                              22

<210> SEQ ID NO 427
<211> LENGTH: 23
<212> TYPE: RNA
```

```
<213> ORGANISM: Unknown
<220> FEATURE:
<223> OTHER INFORMATION: D. melanogaster or H. sapiens or M. musculus
      or C. elegans or HeLa cells

<400> SEQUENCE: 427
uggaauguaa agaaguaugu auu                                              23

<210> SEQ ID NO 428
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 428
uaucacagcc agcuuugaug agc                                              23

<210> SEQ ID NO 429
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 429
uaucacagcc agcuuugaug agc                                              23

<210> SEQ ID NO 430
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 430
uaucacagcc agcuuugagg agc                                              23

<210> SEQ ID NO 431
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 431
uaucacagcc agcuuugagg agc                                              23

<210> SEQ ID NO 432
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 432
ucacugggca aagugugucu ca                                               22

<210> SEQ ID NO 433
<211> LENGTH: 21
<212> TYPE: RNA
<213> ORGANISM: Unknown
```

```
<220> FEATURE:
<223> OTHER INFORMATION: D. melanogaster or H. sapiens or M. musculus
      or C. elegans or HeLa cells

<400> SEQUENCE: 433
auaaagcuag acaaccauug a                                                   21

<210> SEQ ID NO 434
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 434
aaaggaacga ucguugugau aug                                                 23

<210> SEQ ID NO 435
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 435
uaucacagug gcuguucuuu uu                                                  22

<210> SEQ ID NO 436
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 436
uaucacagug gcuguucuuu uu                                                  22

<210> SEQ ID NO 437
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 437
uaucacagug gcuguucuuu uu                                                  22

<210> SEQ ID NO 438
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 438
uggaagacua gugauuuugu ugu                                                 23

<210> SEQ ID NO 439
<211> LENGTH: 23
<212> TYPE: RNA
<213> ORGANISM: Unknown
<220> FEATURE:
```

-continued

<223> OTHER INFORMATION: D. melanogaster or H. sapiens or M. musculus
     or C. elegans or HeLa cells

<400> SEQUENCE: 439
uaauacuguc agguaaagau guc                                              23

<210> SEQ ID NO 440
<211> LENGTH: 23
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 440
ucuuugguua ucuagcugua uga                                              23

<210> SEQ ID NO 441
<211> LENGTH: 21
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 441
acccuguaga uccgaauuug u                                                21

<210> SEQ ID NO 442
<211> LENGTH: 21
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 442
caucacaguc ugaguucuug c                                                21

<210> SEQ ID NO 443
<211> LENGTH: 23
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 443
ugaguauuac aucagguacu ggu                                              23

<210> SEQ ID NO 444
<211> LENGTH: 22
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 444
uaucacagcc auuugauga gu                                                22

<210> SEQ ID NO 445
<211> LENGTH: 22
<212> TYPE: RNA
<213> ORGANISM: Unknown
<220> FEATURE:
<223> OTHER INFORMATION: D. melanogaster or H. sapiens or M. musculus or C. elegans or HeLa cells

<400> SEQUENCE: 445
uaucacagcc auuugacga gu                                            22

<210> SEQ ID NO 446
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 446
uaucacagcc auuugacga gu                                            22

<210> SEQ ID NO 447
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 447
ucagucuuuu ucucucuccu a                                            21

<210> SEQ ID NO 448
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 448
uagcagcaca uaaugguuug ug                                           22

<210> SEQ ID NO 449
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 449
uagcagcaca ucaugguuua ca                                           22

<210> SEQ ID NO 450
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 450
uagcagcacg uaaauauugg cg                                           22

<210> SEQ ID NO 451
<211> LENGTH: 20
<212> TYPE: RNA
<213> ORGANISM: Unknown
<220> FEATURE:
<223> OTHER INFORMATION: D. melanogaster or H. sapiens or M. musculus
      or C. elegans or HeLa cells

```
<400> SEQUENCE: 451
acugcaguga aggcacuugu                                              20

<210> SEQ ID NO 452
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 452
uaaggugcau cuagugcaga ua                                           22

<210> SEQ ID NO 453
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 453
ugugcaaauc uaugcaaaac uga                                          23

<210> SEQ ID NO 454
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 454
ugugcaaauc caugcaaaac uga                                          23

<210> SEQ ID NO 455
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 455
ugugcaaauc caugcaaaac uga                                          23

<210> SEQ ID NO 456
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 456
uaaagugcuu auagugcagg ua                                           22

<210> SEQ ID NO 457
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells
```

-continued

```
<400> SEQUENCE: 457
uagcuuauca gacugauguu ga                                              22

<210> SEQ ID NO 458
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 458
aagcugccag uugaagaacu gu                                              22

<210> SEQ ID NO 459
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 459
aucacauugc caggauuuc c                                                21

<210> SEQ ID NO 460
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 460
aucacauugc caggauuac cac                                              23

<210> SEQ ID NO 461
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 461
uggcucaguu cagcaggaac ag                                              22

<210> SEQ ID NO 462
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 462
uggcucaguu cagcaggaac ag                                              22

<210> SEQ ID NO 463
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 463
```
cauugcacuu gucucggucu ga                                             22

<210> SEQ ID NO 464
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 464
uucaaguaau ccaggauagg cu                                             22

<210> SEQ ID NO 465
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 465
uucaaguaau ucaggauagg uu                                             22

<210> SEQ ID NO 466
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 466
uucacagugg cuaaguuccg cu                                             22

<210> SEQ ID NO 467
<211> LENGTH: 20
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 467
uucacagugg cuaaguucug                                                20

<210> SEQ ID NO 468
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 468
aaggagcuca cagucuauug ag                                             22

<210> SEQ ID NO 469
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 469

```
cuagcaccau cugaaaucgg uu                                          22
```

<210> SEQ ID NO 470
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 470

```
uagcaccauu ugaaaucagu guu                                         23
```

<210> SEQ ID NO 471
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 471

```
uagcaccauu ugaaaucggu ua                                          22
```

<210> SEQ ID NO 472
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 472

```
uguaaacauc cucgacugga agc                                         23
```

<210> SEQ ID NO 473
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 473

```
cuuucagucg gauguuugca gc                                          22
```

<210> SEQ ID NO 474
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 474

```
uguaaacauc cuacacucag c                                           21
```

<210> SEQ ID NO 475
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 475

```
uguaaacauc cuacacucuc agc                                         23
```

<210> SEQ ID NO 476
<211> LENGTH: 22
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 476
uguaaacauc cccgacugga ag                                           22

<210> SEQ ID NO 477
<211> LENGTH: 21
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 477
ggcaagaugc uggcauagcu g                                            21

<210> SEQ ID NO 478
<211> LENGTH: 21
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 478
uauugcacau uacuaaguug c                                            21

<210> SEQ ID NO 479
<211> LENGTH: 19
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 479
gugcauugua guugcauug                                               19

<210> SEQ ID NO 480
<211> LENGTH: 20
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 480
acccguagau ccgaucuugu                                              20

<210> SEQ ID NO 481
<211> LENGTH: 22
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 481
cacccguaga accgaccuug cg                                           22

```
<210> SEQ ID NO 482
<211> LENGTH: 20
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 482
uacaguacug ugauaacuga                                                  20

<210> SEQ ID NO 483
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 483
uggaguguga caauguguu ugu                                               23

<210> SEQ ID NO 484
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 484
uggaguguga caauguguu uga                                               23

<210> SEQ ID NO 485
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 485
uggaguguga caauguguu ug                                                22

<210> SEQ ID NO 486
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 486
cauuauuacu uuugguacgc g                                                21

<210> SEQ ID NO 487
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 487
uuaaggcacg cggugaaugc ca                                               22
```

```
<210> SEQ ID NO 488
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 488
uuaaggcacg cgggugaaug c                                                  21

<210> SEQ ID NO 489
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 489
ucccugagac ccuuuaaccu gug                                                23

<210> SEQ ID NO 490
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 490
ucccugagac ccuaacuugu ga                                                 22

<210> SEQ ID NO 491
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 491
ucguaccgug aguaauaaug c                                                  21

<210> SEQ ID NO 492
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 492
ucggauccgu cugagcuugg cu                                                 22

<210> SEQ ID NO 493
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 493
ucacagugaa ccggucucuu uu                                                 22

<210> SEQ ID NO 494
```

```
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 494 cuuuuucgg ucugggcuug c                                              21

<210> SEQ ID NO 495
<211> LENGTH: 20
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 495
cagugcaaug uuaaaagggc                                               20

<210> SEQ ID NO 496
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 496
uaaagcuaga uaaccgaaag u                                             21

<210> SEQ ID NO 497
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 497
uaacagucua cagccauggu cgu                                           23

<210> SEQ ID NO 498
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 498 uuggucccu ucaaccagcu gu                                             22

<210> SEQ ID NO 499
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 499
ugugacuggu ugaccagagg ga                                            22

<210> SEQ ID NO 500
<211> LENGTH: 24
```

```
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 500
uauggcuuuu uauuccuaug ugaa                                          24

<210> SEQ ID NO 501
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 501
acuccauuug uuuugaugau gga                                           23

<210> SEQ ID NO 502
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 502
uauugcuuaa gaauacgcgu ag                                            22

<210> SEQ ID NO 503
<211> LENGTH: 17
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 503
agcugguguu gugaauc                                                  17

<210> SEQ ID NO 504
<211> LENGTH: 18
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 504
ucuacagugc acgugucu                                                 18

<210> SEQ ID NO 505
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 505
agugguuuua cccuauggua g                                             21

<210> SEQ ID NO 506
<211> LENGTH: 21
<212> TYPE: RNA
```

```
<213> ORGANISM: Unknown
<220> FEATURE:
<223> OTHER INFORMATION: D. melanogaster or H. sapiens or M. musculus
      or C. elegans or HeLa cells

<400> SEQUENCE: 506
aacacugucu gguaaagaug g                                              21

<210> SEQ ID NO 507
<211> LENGTH: 20
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 507
cauaaaguag aaagcacuac                                                20

<210> SEQ ID NO 508
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 508
uguaguguuu ccuacuuuau gg                                             22

<210> SEQ ID NO 509
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 509
auaagacgag caaaaagcuu gu                                             22

<210> SEQ ID NO 510
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 510
ugagaugaag cacuguagcu ca                                             22

<210> SEQ ID NO 511
<211> LENGTH: 18
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 511
uuagaugaag cacuguag                                                  18

<210> SEQ ID NO 512
<211> LENGTH: 22
<212> TYPE: RNA
<213> ORGANISM: Unknown
```

```
<220> FEATURE:
<223> OTHER INFORMATION: D. melanogaster or H. sapiens or M. musculus
      or C. elegans or HeLa cells

<400> SEQUENCE: 512
uacaguauag augauguacu ag                                              22

<210> SEQ ID NO 513
<211> LENGTH: 24
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 513
guccaguuuu cccaggaauc ccuu                                            24

<210> SEQ ID NO 514
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 514
ugagaacuga auuccauggg uuu                                             23

<210> SEQ ID NO 515
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 515
guguguggaa augcuucugc c                                               21

<210> SEQ ID NO 516
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 516
ucagugcacu acagaacuuu gu                                              22

<210> SEQ ID NO 517
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 517
ucuggcuccg ugucuucacu cc                                              22

<210> SEQ ID NO 518
<211> LENGTH: 23
<212> TYPE: RNA
<213> ORGANISM: Unknown
<220> FEATURE:
```

<223> OTHER INFORMATION: D. melanogaster or H. sapiens or M. musculus
     or C. elegans or HeLa cells

<400> SEQUENCE: 518
ucucccaacc cuuguaccag ugu                                     23

<210> SEQ ID NO 519
<211> LENGTH: 22
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 519
cuagacugag gcuccuugag gu                                      22

<210> SEQ ID NO 520
<211> LENGTH: 21
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 520
ucagugcaug acagaacuug g                                       21

<210> SEQ ID NO 521
<211> LENGTH: 20
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 521
uugcauaguc acaaaaguga                                         20

<210> SEQ ID NO 522
<211> LENGTH: 22
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 522
uagguuaucc guguugccuu cg                                      22

<210> SEQ ID NO 523
<211> LENGTH: 22
<212> TYPE: RNA
<213> ORGANISM: Unknown
<220> FEATURE:
<223> OTHER INFORMATION: D. melanogaster or H. sapiens or M. musculus
     or C. elegans or HeLa cells

<400> SEQUENCE: 523
uuaaugcuaa uugugauagg gg                                      22

<210> SEQ ID NO 524
<211> LENGTH: 23
<212> TYPE: RNA
<213> ORGANISM: Unknown
<220> FEATURE:
<223> OTHER INFORMATION: D. melanogaster or H. sapiens or M. musculus -continued or C. elegans or HeLa cells

<400> SEQUENCE: 524
aacauucaac gcugucggug agu                                          23

<210> SEQ ID NO 525
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 525
uuuggcaaug guagaacuca ca                                           22

<210> SEQ ID NO 526
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 526
uauggcacug guagaauuca cug                                          23

<210> SEQ ID NO 527
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 527
cuuuuugcgg ucugggcuug uu                                           22

<210> SEQ ID NO 528
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 528
uggacggaga acugauaagg gu                                           22

<210> SEQ ID NO 529
<211> LENGTH: 18
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 529
uggagagaaa ggcaguuc                                                18

<210> SEQ ID NO 530
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

```
<400> SEQUENCE: 530
caaagaauuc uccuuuggg cuu                                        23

<210> SEQ ID NO 531
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 531
ucgugucuug uguugcagcc gg                                        22

<210> SEQ ID NO 532
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 532
uaacacuguc ugguaacgau g                                         21

<210> SEQ ID NO 533
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 533
caucccuugc augguggagg gu                                        22

<210> SEQ ID NO 534
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 534
gugccuacug agcugacauc agu                                       23

<210> SEQ ID NO 535
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 535
ugauauguuu gauauauuag gu                                        22

<210> SEQ ID NO 536
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells
```

```
<400> SEQUENCE: 536
caacggaauc ccaaaagcag cu                                              22

<210> SEQ ID NO 537
<211> LENGTH: 18
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 537
cugaccuaug aauugaca                                                   18

<210> SEQ ID NO 538
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 538
uaccacaggg uagaaccacg ga                                              22

<210> SEQ ID NO 539
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 539
aacuggccua caaaguccca g                                               21

<210> SEQ ID NO 540
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 540
uguaacagca acuccaugug ga                                              22

<210> SEQ ID NO 541
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 541
uagcagcaca gaaauauugg c                                               21

<210> SEQ ID NO 542
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 542
```

-continued uagguaguuu cauguuguug g                          21

<210> SEQ ID NO 543
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 543
uucaccaccu ucuccaccca gc                         22

<210> SEQ ID NO 544
<211> LENGTH: 19
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 544
gguccagagg ggagauagg                             19

<210> SEQ ID NO 545
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 545
cccaguguuc agacuaccug uu                         22

<210> SEQ ID NO 546
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 546
uaauacugcc ugguaaugau gac                        23

<210> SEQ ID NO 547
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 547
uacucaguaa ggcauuguuc u                          21

<210> SEQ ID NO 548
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 548

```
uacucaguaa ggcauuguuc u                                              21

<210> SEQ ID NO 549
<211> LENGTH: 21
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 549
ugaaauguuu aggaccacua g                                              21

<210> SEQ ID NO 550
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 550
uucccuuugu cauccuaugc cug                                            23

<210> SEQ ID NO 551
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 551
uccuucauuc caccggaguc ug                                             22

<210> SEQ ID NO 552
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 552
gugaaauguu uaggaccacu aga                                            23

<210> SEQ ID NO 553
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 553
gugaaauguu uaggaccacu aga                                            23

<210> SEQ ID NO 554
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 554
uacaguaguc ugcacauugg uu                                             22
```

<210> SEQ ID NO 555
<211> LENGTH: 22
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 555
cccuguagaa ccgaauuugu gu                                              22

<210> SEQ ID NO 556
<211> LENGTH: 24
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 556
aacccguaga uccgaacuug ugaa                                            24

<210> SEQ ID NO 557
<211> LENGTH: 23
<212> TYPE: RNA
<213> ORGANISM: Unknown
<220> FEATURE:
<223> OTHER INFORMATION: D. melanogaster or H. sapiens or M. musculus
      or C. elegans or HeLa cells

<400> SEQUENCE: 557
gcuucuccug gcucuccucc cuc                                             23

<210> SEQ ID NO 558
<211> LENGTH: 24
<212> TYPE: DNA
<213> ORGANISM: Artificial Sequence
<220> FEATURE:
<223> OTHER INFORMATION: Oligonucleotide primer including Ban I
      restriction site with homology to 5'-adapter oligonucleotide
      (SEQ ID NO: 54) and short mouse RNAs

<400> SEQUENCE: 558
gactagctgg aattcgcggt taaa                                            24

<210> SEQ ID NO 559
<211> LENGTH: 30
<212> TYPE: DNA
<213> ORGANISM: Artificial Sequence
<220> FEATURE:
<223> OTHER INFORMATION: Oligonucleotide primer including Ban I
      restriction site with homology to 3'-adapter oligonucleotide
      (SEQ ID NO: 55) and short mouse RNAs

<400> SEQUENCE: 559
cagccaacag gcaccgaatt cctcactaaa                                      30

<210> SEQ ID NO 560
<211> LENGTH: 21
<212> TYPE: RNA
<213> ORGANISM: Caenorhabditis elegans

<400> SEQUENCE: 560
ucccugagac cucaagugug a                                               21

```
<210> SEQ ID NO 561
<211> LENGTH: 22
<212> TYPE: RNA
<213> ORGANISM: Drosophila melanogaster

<400> SEQUENCE: 561
ucccugagac ccuaacuugu ga                                            22

<210> SEQ ID NO 562
<211> LENGTH: 24
<212> TYPE: RNA
<213> ORGANISM: Mus musculus

<400> SEQUENCE: 562
ucccugagac ccuuuaaccu guga                                          24
```

The invention claimed is:

1. An isolated nucleic acid molecule selected from the group consisting of:
   (a) a nucleotide sequence as shown in SEQ ID NO: 487 or SEQ ID NO: 342;
   (b) a nucleotide sequence which is the complement of (a);
   (c) a nucleotide sequence consisting of 18 to 25 nucleotides which has an identity of at least 80% to the nucleotide sequence as shown in SEQ ID NO: 487 or the complement thereof; and
   (d) a nucleotide sequence consisting of 60 to 80 nucleotides which has an identity of at least 80% to the nucleotide sequence as shown in SEQ ID NO: 342 or the complement thereof.

2. The nucleic acid molecule of claim 1, wherein the identity of sequence (c) is at least 90%.

3. The nucleic acid molecule of claim 1, wherein the identity of sequence (c) is at least 95%.

4. The nucleic acid molecule of claim 1, a miRNA precursor molecule having the nucleobase sequence as shown in SEQ ID NO: 342, or a DNA molecule coding therefor.

5. The nucleic acid molecule of claim 1, which is single-stranded.

6. The nucleic acid molecule of claim 1, which is at least partially double-stranded.

7. The nucleic acid molecule of claim 1, which is selected from RNA, DNA or nucleic acid analog molecules.

8. The nucleic acid molecule of claim 7, which is a molecule containing at least one modified nucleotide analog.

9. A composition comprising at least one nucleic acid molecule of claim 1 and a pharmaceutically acceptable carrier.

10. The composition of claim 9 wherein said pharmaceutically acceptable carrier is suitable for diagnostic applications.

11. The composition of claim 9 wherein said pharmaceutically acceptable carrier is suitable for therapeutic applications.

12. The composition of claim 9 as a marker or modulator of developmental disorders.

13. The composition of claim 9 as a marker or modulator of gene expression.

14. The nucleic acid molecule of claim 1, wherein the identity of sequence (c) is 100%.

15. The nucleic acid molecule of claim 8, wherein said modified nucleotide analog is a 2' modified nucleotide.

16. The nucleic acid molecule of claim 8, wherein said modified nucleotide analog is a backbone-modified nucleotide.

17. The nucleic acid molecule of claim 8, wherein said molecule has at least one locked nucleic acid.

18. The nucleic acid molecule of claim 1 having a length of 21, 22 or 23 nucleotides.

19. A recombinant expression vector comprising at least one nucleic acid molecule of claim 1.

* * * * *